United States Patent [19]

Murata et al.

[11] Patent Number: 5,061,804

[45] Date of Patent: Oct. 29, 1991

[54] 3-PYRROLIDINYLTHIO-1-AZABICYCLO-(3.2.0)HEPT-2-ENE-2-CARBOXYLIC ACID DERIVATIVES AND PROCESSES FOR THE PREPARATION THEREOF

[75] Inventors: Masayoshi Murata, Osaka; Hideo Tsutsumi, Toyonaka; Keiji Matsuda, Takatsuki; Hohji Hattori, Sakai; Takashi Nakajima, Toyonaka, all of Japan

[73] Assignee: Fujisawa Pharmaceutical Co., Ltd., Osaka, Japan

[21] Appl. No.: 489,263

[22] Filed: Mar. 6, 1990

Related U.S. Application Data

[62] Division of Ser. No. 121,881, Nov. 17, 1987, Pat. No. 4,963,543.

[30] Foreign Application Priority Data

Nov. 24, 1986 [GB] United Kingdom ............... 8628063
Dec. 31, 1986 [GB] United Kingdom ............... 8631081
Apr. 21, 1987 [GB] United Kingdom ............... 8709399
Jul. 17, 1987 [GB] United Kingdom ............... 8716937

[51] Int. Cl.$^5$ ............................................ C07D 403/12
[52] U.S. Cl. .................................... 546/281; 548/136; 548/251; 548/518; 548/550; 548/551; 548/266.6; 548/110 M
[58] Field of Search ............... 548/550, 551, 518, 251, 548/136, 269; 546/281

*Primary Examiner*—Robert Gerstl
*Attorney, Agent, or Firm*—Oblon, Spivak, McClelland, Maier & Neustadt

[57] ABSTRACT

3-thio pyrrolidines are intermediates for carbapenams.

4 Claims, No Drawings

3-PYRROLIDINYLTHIO-1-AZABICYCLO-(3.2.0)HEPT-2-ENE-2-CARBOXYLIC ACID DERIVATIVES AND PROCESSES FOR THE PREPARATION THEREOF

This is a division of application Ser. No. 07/121,881, filed on Nov. 17, 1987 now U.S. Pat. No. 4,963,543.

The present invention relates to novel 3-pyrrolidinylthio-1-azabicyclo[3.2.0]hept-2-ene-2-carboxylic acid derivatives and pharmaceutically acceptable salts thereof.

More particularly, it relates to novel 3-pyrrolidinylthio-1-azabicyclo[3.2.0]hept-2-ene-2-carboxylic acid derivatives and pharmaceutically acceptable salts thereof, which have antimicrobial activity, to processes for the preparation thereof, to a pharmaceutical composition comprising the same, and to a use of the same as a medicament and in treatment of infectious diseases in human being or animal.

Accordingly, one object of the present invention is to provide novel 3-pyrrolidinylthio-1-azabicyclo[3.2.0]hept-2-ene-2-carboxylic acid derivatives and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid derivatives and salts thereof.

A further object of the present invention is to provide a pharmaceutical composition comprising, as an active ingredient, said 3-pyrrolidinylthio-1-azabicyclo[3.2.0]hept-2-ene-2-carboxylic acid derivatives and pharmaceutically acceptable salts thereof.

Still further object of the present invention is to provide a use of said 3-pyrrolidinylthio-1-azabicyclo[3.2.0]hept-2-ene-2-carboxylic acid derivatives and pharmaceutically acceptable salts thereof as a medicament and in the treatment of infectious diseases by pathogenic microorganisms in human being or animals.

The object 3-pyrrolidinylthio-1-azabicyclo[3.2.0]hept-2-ene-2-carboxylic acid derivatives are novel and can be represented by the following general formula:

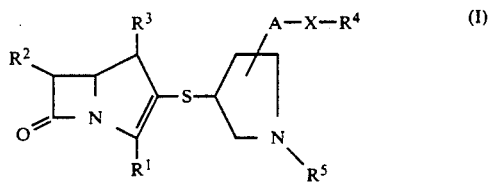

om which $R^1$ is carboxy or protected carboxy, $R^2$ is hydroxy(lower)alkyl or protected hydroxy(lower)alkyl, $R^3$ is hydrogen or lower alkyl, $R^4$ is lower alkyl having suitable substituent(s), heterocyclic group optionally substituted by suitable substituent(s), or lower alkylsulfonyl, $R^5$ is hydrogen, lower alkanimidoyl or iminoprotective group, A is lower alkylene, and X is sulfur, oxygen, imino or protected imino, provided that when X is oxygen, then $R^4$ is not "protected or unprotected ureido(lower)alkyl", and pharmaceutically acceptable salts thereof.

In the object derivatives (I) and the intermediary compounds mentioned below, it is to be understood that there may be one or more stereo-isomeric pair(s) such as optical isomers due to asymmetric carbon atom(s), and such isomers are also included within the scope of the present invention.

Suitable pharmaceutically acceptable salts of the object derivatives (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, dibenzylamine salt, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.); an intermolecular quaternary salt, and the like.

According to the present invention, the object derivatives (I) and pharmaceutically acceptable salts thereof can be prepared by the processes as illustrated by the following reaction schemes.

Process 1:

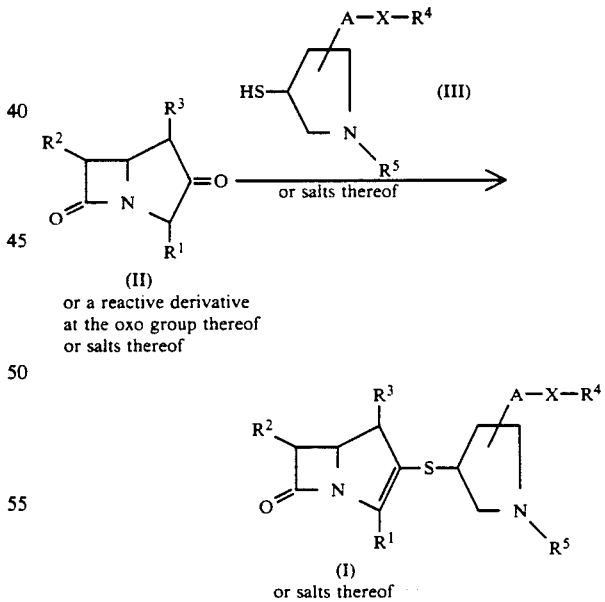

(II)
or a reactive derivative
at the oxo group thereof
or salts thereof (I)
or salts thereof Process 2:

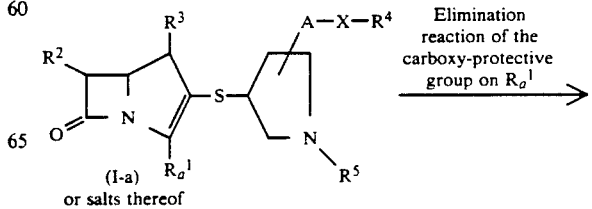

(I-a)
or salts thereof

Elimination reaction of the carboxy-protective group on $R_a^1$

-continued

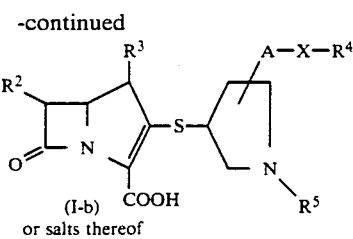
(I-b) or salts thereof

Process 3:

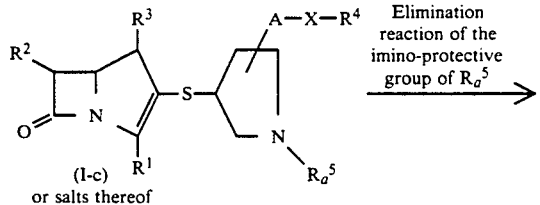
(I-c) or salts thereof

Elimination reaction of the imino-protective group of $R_a^5$

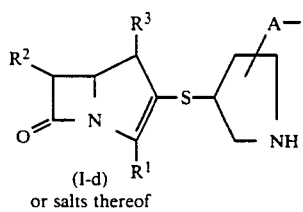
(I-d) or salts thereof

Process 4:

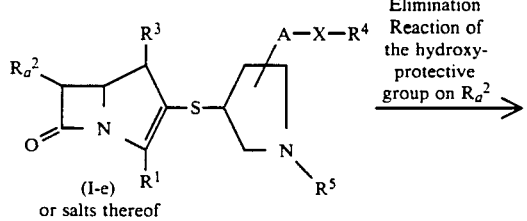
(I-e) or salts thereof

Elimination Reaction of the hydroxy-protective group on $R_a^2$

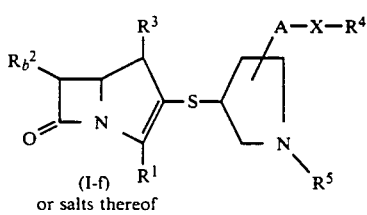
(I-f) or salts thereof

Process 5:

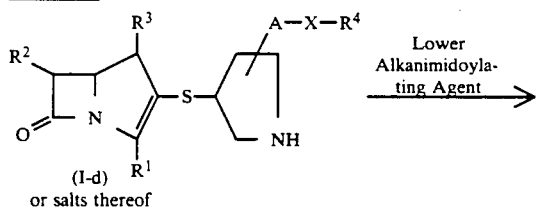
(I-d) or salts thereof

Lower Alkanimidoylating Agent

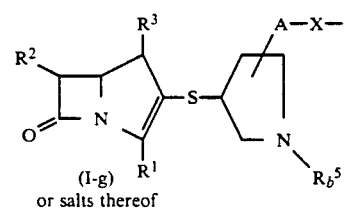
(I-g) or salts thereof in which
$R^1$, $R^2$, $R^3$, $R^4$, $R^5$, A and X are each as defined above,
$R_a^1$ is protected carboxy,
$R_a^2$ is protected hydroxy(lower)alkyl,
$R_b^2$ is hydroxy(lower)alkyl,
$R_a^5$ is imino-protective group, and
$R_b^5$ is lower alkanimidoyl.

The compound (III) used in the Process 1 is new and can be prepared, for example, by the following methods or a conventional manner.

Method A:

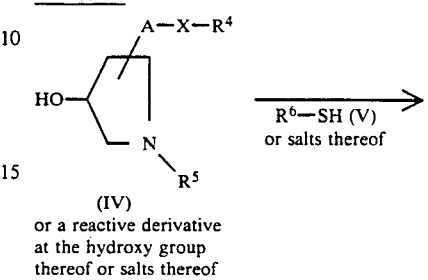
(IV) or a reactive derivative at the hydroxy group thereof or salts thereof $R^6$—SH (V) or salts thereof

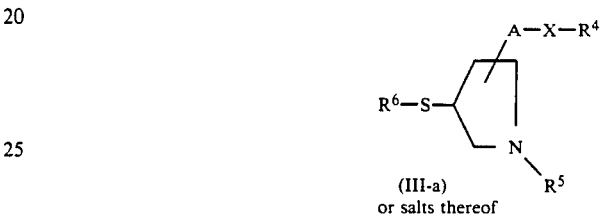
(III-a) or salts thereof

Method B:

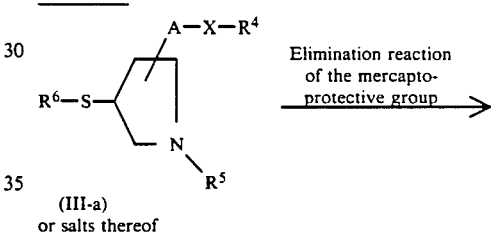
(III-a) or salts thereof

Elimination reaction of the mercapto-protective group

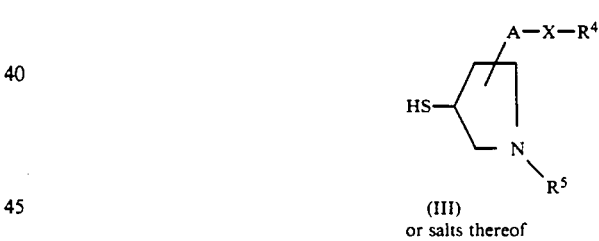
(III) or salts thereof in which
$R^4$, $R^5$, A and X are each as defined above, and
$R^6$ is mercapto-protective group.

In the above and subsequent descriptions of the present specification, suitable examples and illustrations of the various definitions which the present invention includes within the scope thereof are explained in detail as follows.

The term "lower" is intended to mean 1 to 6 carbon atoms, unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri )halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, propoxycarbonyloxymethyl ester, t-butoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.];

lower alkenyl ester (e.g. vinyl ester, allyl ester, etc.);

lower alkynyl ester (e.g. ethynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have at least one suitable substituent(s) (e.g. phenyl ester, 4-chlorophenyl ester, tolyl ester, t-butylphenyl ester, xylyl ester, mesityl ester, cumenyl ester, etc.);

phthalidyl ester; and the like.

More preferable example of the protected carboxy thus defined may be phenyl($C_1$–$C_4$)alkoxycarbonyl which may have a nitro group and ($C_2$–$C_4$)alkenyloxycarbonyl, and the most preferable one may be 4-nitrobenzyloxycarbonyl and allyloxycarbonyl.

Suitable "hydroxy(lower)alkyl" and hydroxy(lower)alkyl in the embodiment of "lower alkyl having suitable substituent(s)" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$–$C_4$)alkyl and the most preferable one may be 1-hydroxyethyl for $R^2$ and 2-hydroxyethyl for $R^4$.

Suitable "protected hydroxy(lower)alkyl" and protected hydroxy(lower)alkyl in the embodiment of "lower alkyl having suitable substituent(s)" means aforementioned hydroxy(lower)alkyl, in which the hydroxy group is protected by a conventional hydroxy-protective group such as those mentioned in the explanation of imino-protective group as mentioned below; and further ar(lower)alkyl such as mono- or di- or triphenyl(lower)alkyl (e.g. benzyl, benzhydryl, trityl, etc.), etc.;

trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.) etc.; and the like.

More preferable example of "protected hydroxy(lower)alkyl" thus defined may be carbamoyloxy($C_1$–$C_4$)alkyl, [phenyl (or nitrophenyl)($C_1$–$C_4$)alkoxy]carbonyloxy($C_1$–$C_4$)alkyl, [triphenyl($C_1$–$C_4$)alkoxy](-$C_1$–$C_4$)alkyl and [tri($C_1$–$C_4$)alkylsilyl]oxy($C_1$–$C_4$)alkyl, and the most preferable one may be 1(4-nitrobenzyloxycarbonyloxy)ethyl for $R^2$ and 2-carbamoyloxyethyl for $R^4$.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl and the most preferable one may be methyl.

Suitable "lower alkyl having suitable substituents(s)" may include protected or unprotected hydroxy(lower)alkyl; protected or unprotected hydroxy(lower)alkyl having protected or unprotected amino; halo(lower)alkyl; protected or unprotected carbamoyl(lower)alkyl; protected or unprotected amino(lower)alkyl; protected or unprotected ureido(lower)alkyl; protected or unprotected ureidocarbonyl(lower)alkyl; tiazolyl(lower)alkyl; and the like.

Suitable protected or unprotected hydroxy(lower)alkyl having protected or unprotected amino means aforementioned hydroxy(lower)alkyl having amino group such as 1-amino-1-hydroxymethyl, 2-amino-1-hydroxyethyl, 1-amino-2-hydroxyethyl, 3-amino-2-hydroxypropyl, 2-amino-3-hydroxypropyl, 4-amino-3-hydroxybutyl, 5-amino-4-hydroxypentyl, 6-amino-5-hydroxyhexyl, and the like, in which the amino and/or hydroxy group(s) may be protected by a conventional amino- and/or hydroxy-protective group(s) as mentioned below or above.

More preferable example of protected or unprotected hydroxy(lower)alkyl which has protected or unprotected amino thus defined may be hydroxy($C_1$–$C_4$)alkyl having amino or phenyl (or nitrophenyl)($C_1$–$C_4$)alkoxycarbonylamino, and the most preferable one may be 3-amino-2-hydroxypropyl and 2-hydroxy-3-(4-nitrobenzyloxycarbonyl)aminopropyl.

Suitable "halo(lower)alkyl" may include straight or branched lower alkyl having at least one (preferably one to three) halogen (e.g. chlorine, bromine, iodine, fluorine) such as chloromethyl, fluoromethyl, dichloromethyl, dibromomethyl, diiodomethyl, difluoromethyl, trifluoromethyl, chloroethyl, chlorofluoroethyl, difluoroethyl, trifluoroethyl, chloropropyl, difluorcpropyl, trichlorobutyl, chloropentyl, chlorohexyl, and the like, in which more preferable example may be dihalo($C_1$–$C_4$)alkyl and the most preferable one may be difluoromethyl.

Suitable "carbamoyl(lower)alkyl" may include straight or branched lower alkyl having carbamoyl group such as carbamoylmethyl, carbamoylethyl, carbamoylpropyl, 1-(carbamoylmethyl)ethyl, 1-carbamoyl-1-methylethyl, carbamoylbutyl, carbamoylpentyl, carbamoylhexyl, and the like, in which more preferable example may be carbamoyl($C_1$–$C_4$)alkyl and the most preferable one may be carbamoylmethyl and 1-carbamoyl-1-methylethyl.

Suitable "protected carbamoyl(lower)alkyl" means aforementioned carbamoyl(lower)alkyl, in which the carbamoyl group is protected by a conventional carbamoyl-protective group such as mono(or di or tri)halo(lower)alkanoyl (e.g. trichloroacetyl, etc.), ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.), bis(lower alkoxyphenyl)(lower)alkyl [e.g. bis(4-methoxyphenyl)methyl, etc.], halosulfonyl (e.g. chlorosulfonyl, etc.), and the like, in which more preferable one may be trihalo($C_1$-$C_4$)alkanoyl, bis[($C_1$-$C_4$)alkoxyphenyl]($C_1$-$C_4$)alkyl and halosulfonyl.

More preferable example of "protected carbamoyl(lower)alkyl" thus defined may be trihalo($C_1$-$C_4$)alkanoylcarbamoyl($C_1$-$C_4$)alkyl, N-[bis{($C_1$-$C_4$)alkoxyphenyl}($C_1$-$C_4$)alkyl]carbamoyl($C_1$-$C_4$)alkyl and halosulfonylcarbamoyl($C_1$-$C_4$)alkyl.

Suitable "amino(lower)alkyl" may include straight or branched lower alkyl having amino group such as aminomethyl, 1-(or 2-)aminoethyl, aminopropyl, aminobutyl, 2-amino-1,1-dimethylethyl, 1-(or 2- or 3-)amino-1-(or 2-)methylpropyl, aminopentyl, aminohexyl, and the like, in which more preferable example may be amino($C_1$-$C_4$)alkyl, and the most preferable one may be 2-aminoethyl and 2-amino-1,1-dimethylethyl.

Suitable "protected amino(lower)alkyl" means aforementioned amino(lower)alkyl, in which the amino group is protected by a conventional amino-protective group such as those mentioned in the explanation of protected hydroxy(lower)alkyl as mentioned above, in which more preferable example may be phenyl(or nitrophenyl)($C_1$-$C_4$)alkoxycarbonyl and $C_1$-$C_4$ alkylsulfonyl, and the most preferable one may be 4-nitrobenzyloxycarbonyl and methylsulfonyl.

More preferable example of "protected amino(lower)alkyl" thus defined may be N-[phenyl(or nitrophenyl)-$C_1$-$C_4$)alkoxycarbonyl]amino($C_1$-$C_4$)alkyl, and ($C_1$-$C_4$)alkylsulfonylamino($C_1$-$C_4$(alkyl, and the most preferable one may be 2-(4-nitrobenzyloxycarbonylamino)ethyl, 1,1-dimethyl-2-(4-nitrobenzyloxycarbonylamino)ethyl and 2-(methylsulfonylamino)ethyl.

Suitable "ureido(lower)alkyl" may include straight or branched lower alkyl having ureido group, such as ureidomethyl, ureidoethyl, ureidopropyl, 1-(ureidomethyl)ethyl, 1-ureido-1-methylethyl, ureidooutyl, 1,1-dimethyl-2-ureidoethyl, ureidopentyl, ureidohexyl, and the like, in which more preferable example may be ureido($C_1$-$C_4$)alkyl and the most preferable one may be 2-ureidoethyl and 1,1-dimethyl-2-ureidoethyl.

Suitable "protected ureido(lower)alkyl" means aforementioned ureido(lower)alkyl, in which the ureido group is protected by a conventional ureido-protective group such as ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.) bis(lower alkoxyphenyl)(lower)alkyl[e.g. bis[4-methoxyphenyl)methyl, etc.], and the like, in which more preferable one may be phenyl($C_1$-$C_4$)alkyl.

Suitable "ureidocarbonyl(lower)alkyl" may include straight or branched lower alkyl having ureidocarbonyl group, such as ureidocarbonylmethyl, ureidocarbonylethyl, ureidocarbonylpropyl, 1-(ureidocarbonylmethyl)ethyl, 1-ureidocarbonyl-1-methylethyl, ureidocarbonylbutyl, 1,1-dimethyl-2-ureidocarbonylethyl, ureidocarbonylpentyl, ureidocarbonylhexyl, and the like, in which more preferable one may be ureidocarbonylmethyl.

Suitable "protected ureidocarbonyl(lower)alkyl" means aforementioned ureidocarbonyl(lower)alkyl, in which the ureido group is protected by a conventional ureido-protective group such as ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.), bis(lower alkoxyphenyl) (lower)alkyl [e.g. bis(4-methoxyphenyl)methyl, etc.], and the like, in which more preferable one may be phenyl($C_1$-$C_4$)alkyl.

Suitable "triazolyl(lower)alkyl" may include straight or branched lower alkyl having triazolyl group as mentioned below such as triazolylmethyl, triazolylethyl, triazolylpropyl, 1-(triazolylmethyl)ethyl, 1-triazolyl-1-methylethyl, triazolylbutyl, triazolylpentyl, triazolylhexyl, and the like, in which more preferable example may be triazolyl($C_1$-$C_4$)alkyl and the most preferable one may be 1,2,4-triazolylmethyl.

Suitable "heterocyclic group" may include saturated or unsaturated, monocyclic or polycyclic heterocyclic group containing at least one hetero-atom such as oxygen, sulfur and nitrogen atom.

Preferable heterocyclic group may be unsaturated, 3 to 8-membered, more preferably 5 or 6-membered, heteromonocyclic group containing 1 to 4 nitrogen atom(s), for example, pyrrolyl, pyrrolinyl, imidazolyl, imidazolinyl, pyrazolyl, pyrazolinyl, pyridyl, pyridyl N-oxide, pyridinio, dihydropyridyl, tetrahydropyridyl [e.g. 1,2,3,6-tetrahydropyridyl, etc.], pyrimidinyl, pyrimidinio, pyrazinyl, pyrazinio, pyridazinyl, pyridazinio, triazinyl [e.g. 1,3,5-triazinyl, 1,2,4-triazinyl and 1,2,3-triazinyl], tetrahydrotriazinyl [e.g. 1,2,5,6-tetrahydro-1,2,4-triazinyl, 1,4,5,6-tetrahydro-1,2,4-triazinyl, etc.], triazinio, triazolyl [e.g. 1H-1,2,4-triazolyl, 1H-1,2,3-triazolyl, 2H-1,2,3-triazolyl, etc.], triazolio, tetrazinyl, tetrazinio, tetrazolyl [e.g. 1H-tetrazolyl and 2H-tetrazolyl], tetrazolio, etc.;

saturated, 3 to 8-membered, more preferably 5 or 6-membered heteromonocyclic group containing 1 to 4 nitrogen atom(s), for example, pyrrolidinyl, imidazolidinyl, piperidino, piperazinyl, etc.;

unsaturated, 3 to 8-membered, more preferably 5 or 6-membered, heteromonocyclic group containing 1 to 2 sulfur atom(s) and 1 to 3 nitrogen atom(s), for example, thiazolyl, thiazolio, isothiazolyl, thiadiazolyl [e.g. 1,2,3-thiadiazolyl, 1,2,4-thiadiazolyl, 1,3,4-thiadiazolyl, 1,2,5-thiadiazolyl], thiadiazolio, thiazolinyl, dihydrothiazinyl, etc.; or the like, wherein said heterocyclic group may be substituted by suitable substituent(s) such as lower alkyl (e.g. methyl, ethyl, propyl, isopropyl, butyl, isobutyl, pentyl, hexyl, etc.); amino or amino(lower)alkyl [e.g. aminomethyl, 1-(or 2-)aminoethyl, aminopropyl, aminobutyl, 1-(or 2- or 3-)amino-1-(or 2-)methylpropyl, aminopentyl, aminohexyl, etc.], in which said amino moiety may be substituted by one or two lower alkyl group(s) as mentioned above; and the like, and further, in case that said heterocyclic group is pyrrolidinyl, the iminomoiety of pyrrolidine ring may be protected by a conventional imino-protective group as mentioned below.

More preferable example of "heterocyclic group optionally substituted by suitable substituent(s) " thus defined may be saturated or unsaturated 5 or 6-membered heteromonocyclic group containing 1 to 4 nitrogen atom(s), or containing 1 to 2 sulfur atom(s) and 1 to 3 nitrogen atom(s), which may have $C_1$-$C_4$ alkyl, N,N-di($C_1$-$C_4$)alkylamino($C_1C_4$)alkyl or phenyl(or nitrophenyl)($C_1$-$C_4$)alkoxycarbonyl, and the most preferable one may be pyridyl, tetrazolyl, pyrrolidinyl, 1-(4-nitrobenzyloxycarbonyl)pyrrolidinyl, thiadiazolyl, 1- methyl-1H-tetrazolyl and 1-{2-(N,N-dimethylamino)e-thyl}-1H-tetrazolyl.

Furthermore, when the heterocyclic group as stated above is, for example, 1,2,4-triazolyl group, there are tautomeric isomers as shown by the following equilibrium:

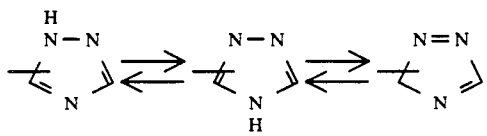

All of the above tautomeric isomers are included within the scope of the present invention and in the present specification, however, the object and intermediary compounds including the group of such tautomeric isomers are represented by using one of the expressions therefor, i.e. 2H— (or 1H—)1,2,4-triazolyl and the formula:

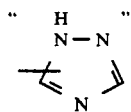

only for the convenient sake.

Suitable "lower alkanimidoyl" may be straight or branched one such as formimidoyl, acetimidoyl, propionimidoyl, butyrimidoyl, isovalerimidoyl, pentanimidoyl, hexanimidoyl, and the like, in which more preferable one may be $(C_1-C_4)$alkanimidoyl and the most preferable one may be acetimidoyl.

Suitable "lower alkylsulfonyl" may include methylsulfonyl, ethylsulfonyl, propylsulfonyl, butylsulfonyl, pentylsulfonyl, hexylsulfonyl, and the like, in which more preferable example may be $(C_1-C_4)$alkylsulfonyl and the most preferable one may be methylsulfonyl.

Suitable imino-protective group in "protected imino" may be the same as those for the "imino-protective group" as mentioned below.

Suitable "imino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include aroyl (e.g. benzoyl, toluoyl, xyloyl, etc.), N-arylcarbamoyl (e.g. N-phenylcarbamoyl, N-tolylcarbamoyl, N-naphthylcarbamoyl, etc.), arenesulfonyl (e.g. benzenesulfonyl, tosyl, etc.), and the like.

The heterocyclic acyl may include heterocyclic-carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include aralkanoyl such as phenyl(lower)alkanoyl (e.g. phenylacetyl, phenylpropionyl, phenylhexanoyl, etc.), aralkoxycarbonyl such as phenyl(lower)alkoxycarbonyl (e.g. benzyloxycarbonyl, phenethyloxycarbonyl, etc.), aryloxyalkanoyl such as phenoxy(lower)alkanoyl (e.g. phenoxyacetyl, phenoxypropionyl, etc.), and the like.

The aliphatic acyl substituted with heterocyclic group(s) may include heterocyclic-alkanoyl such as heterocyclic-(lower)alkanoyl (e.g. thienylacetyl, imidazolylacetyl, furylacetyl, tetrazolylacetyl, thiazolylacetyl, thiadiazolylacetyl, thienylpropionyl, thiadiazolylpropionyl, etc.), and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, and the like, and preferable acyl having such substituent(s) may be mono(or di or tri)haloalkanoyl (e.g. chloroacetyl, bromoacetyl, dichloroacetyl, trifluoroacetyl, etc.), mono(or di or tri)haloalkoxycarbonyl (e.g. chloromethoxycarbonyl, dichloromethoxycarbonyl, 2,2,2-trichloroethoxycarbonyl, etc.), nitro(or halo or lower alkoxy)aralkoxycarbonyl (e.g. nitrobenzyloxycarbonyl, chlorobenzyloxycarbonyl, methoxybenzyloxycarbonyl, etc.), mono(or di or tri)halo(lower)alkylsulfonyl (e.g. fluoromethylsulfonyl, difluoromethylsulfonyl, trifluoromethylsulfonyl, trichloromethylsulfonyl, etc.), and the like.

More preferable example of "imino-protective group" thus defined may be $(C_2-C_4)$alkenyloxycarbonyl and phenyl$(C_1-C_4)$alkoxycarbonyl which may have a nitro group, and the most preferable one may be allyloxycarbonyl and 4-nitrobenzyloxycarbonyl.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1-C_4$ alkylene and the most preferable one may be methylene.

Suitable "mercapto-protective group" may include acyl as mentioned above, ar(lower)alkyl such as mono- or di- or triphenyl(lower)alkyl (e.g. benzyl, phenethyl, benzhydryl, trityl, etc.), and the like, in which more preferable example may be $C_1-C_4$ alkanoyl, aroyl and triphenyl$(C_1-C_4)$alkyl, and the most preferable one may be benzoyl.

The processes for the preparation of the object derivatives (I) of the present invention are explained in detail in the following.

(1) Process 1

The derivatives (I) or salts thereof can be prepared by reacting the compound (II) or a reactive derivative at the oxo group thereof or salts thereof with the compound (III) or salts thereof.

Suitable salts of the compound (II) may be salts with bases such as those given for the derivatives (I).

The reactive derivative at the oxo group of the compound (II) can be represented by the following formula (II'), which is preferably used in this reaction and can be prepared by reacting the compound (II) or salts thereof with an acylating agent.

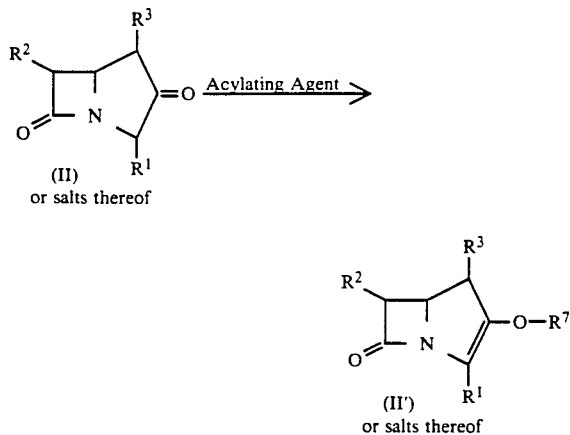

in which

R$^1$, R$^2$ and R$^3$ are each as defined above, and

R$^7$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compounds (e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaninocyclohexyl)carbodiimide, N-ethyl-N'-(3-dimethylaminopropyl)carbodiimide, etc.); N,N'-carbonyldiimidazole, N,N'-carbonylbis(2methylimidazole); keteneimine compounds (e.g. pentamethyleneketene-N-cyclohexylimine, diphenylketene-N-cyclohexylimine); ethoxyacetylene; 1-alkoxy-1-chloroethylene; ethyl polyphosphate; isopropyl polyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like. This acylation reaction may also be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds [e.g. pyridine, picoline, lutidine, N,N-di(lower)alkylaminopyridine such as N,N-dimethylaminopyridine, etc.], quinoline, N-lower alkylmorphorine (e.g. N-methylmorphorine, etc.), N,N-di(lower)alkylbenzylamine (e.g. N,N-dimethylbenzylamine, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie in tautomeric relation with the 3-hydroxy-7-oxo-1-azabicyclo[3.2.0]hept-2-ene ring system of the following formula (IIB), and accordingly, it is to be understood that both of these ring systems are substantially the same.

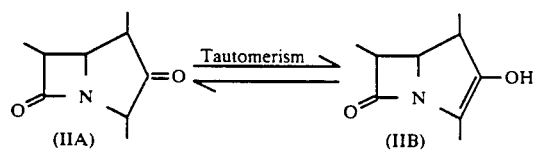

The compound (II') or salts thereof can be used with or without isolation for the subsequent reaction with the compound (III) or salts thereof.

Suitable salts of the compound (III) may be the same as those for the derivatives (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming. ( 2) Process 2

The derivative (I-b) or salts thereof can be prepared by subjecting the derivative (I-a) or salts thereof to elimination reaction of the carboxy-protective group on R$_a^1$.

Suitable salts of the derivative (I-b) may be the same as those for the derivatives (I), and those of the derivative (I-a) may be salts with bases such as those given for the derivatives (I).

The present reaction is usually carried out by a conventional method such as hydrolysis, reduction, and the like.

(i) Hydrolysis

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl, the hydrolysis can be carried out in the presence of tri(lower)alkylammonium fluoride (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction

The reduction method applicable for this elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, palladium hydroxide on carbon, colloidal palladium, palladium on barium sulfate, palladium on barium carbonate, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenyl phosphino)ethane]palladium(0), tetrakis(triphenyl. phosphite)palladium(0), tetrakis(triethyl phosphite)palladium(0), and the like.

This reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The reaction temperature is not critical and the reaction is usually carried out under from cooling to warming.

The elimination reaction can be selected according to the kind of carboxy-protective group to be eliminated The present process includes within the scope thereof a case that the hydroxy- and/or amino- and/or imino-protective group(s) for $R^2$, $R^4$, $R^5$ and X are removed at the same time during the reaction.

(3) Process 3

The derivative (I-d) or salts thereof can be prepared by subjecting the derivative (I-c) or salts thereof to elimination reaction of the imino-protective group of $R_a^5$.

Suitable salts of the derivative (I-c) may be salts with bases such as those given for the derivatives (I), and those of the derivative (I-d) may be the same salts with bases and acids for the derivatives (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the derivative (I-a) in Process 2, and therefore are to be referred to said explanation.

The present process includes within the scope thereof a case that the carboxy- and/or hydroxy- and/or aminoand/or imino-protective group(s) for $R^1$, $R^2$, $R^4$ and X are removed at the same time during the reaction (4) Process 4

The derivative (I-f) or salts thereof can be prepared by subjecting the derivative (I-e) or salts thereof to elimination reaction of the hydroxy-protective group on $R_a{}^2$.

Suitable salts of the derivatives (I-e) and (I-f) may be the same as those for the derivatives (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the derivative (I-a) in process 2, and therefore are to be referred to said explanation.

The present process includes within the scope thereof a case that the carboxy- and/or amino- and/or imino-protective group(s) for $R^1$, $R^4$, $R^5$ and X are removed at the same time during the reaction.

(5) Process 5

The derivative (I-g) or salts thereof can be prepared by reacting the derivative (I-d) or salts thereof with lower alkanimidoylating agent.

Suitable salts of the derivative (I-g) may be the same salts with bases for the derivatives (I).

Suitable lower alkanimidoylating agent may be conventional ones which can introduce the lower alkanimidoyl group as mentioned above into the derivative (I-d), and said preferable agent may be lower alkyl(lower)alkanimidate (e.g. methyl formimidate, ethyl formimidate, methyl acetimidate, ethyl acetimidate, ethyl propionimidate, ethyl butyrimidate, ethyl isovalerimidate, ethyl pentanimidate, ethyl hexanimidate, etc.), (lower)alkanimidoyl halide (e.g. formimidoyl chloride, formimidoyl bromide, acetimidoyl chloride, acetimidoyl bromide, propionimidoyl chloride, butyrimidoyl chloride, isovalerimidoyl chloride, pentanimidoyl chloride, hexanimidoyl chloride, etc.), and the like, or an acid addition salt thereof.

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

The reaction temperature is not critical, and the reaction is usually carried out under from cooling to warming.

Methods A and B for preparing the new starting compound (III) or salts thereof are explained in detail in the following.

(A) Method A

The compound (III-a) or salts thereof can be prepared by reacting the compound (IV) or a reactive derivative at the hydroxy group thereof or salts thereof with the compound (V) or salts thereof.

Suitable salts of the compounds (III-a), (IV) and (V) may be the same as those for the compound (III).

Suitable reactive derivative at the hydroxy group of the compound (IV) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate.

The starting compound (IV) or a reactive derivative at the hydroxy group thereof of this method is new and can be prepared by the methods described in the Preparations mentioned below, or by a conventional process.

Preferable example of the compound (V) may be ar(lower)alkanethiol such as mono- or di- or triphenyl(lower)alkanethiol (e.g. phenylmethanethiol, diphenylmethanethiol, triphenylmethanethiol, etc.), thio(lower)alkanoic S-acid (e.g. thioacetic S-acid, etc.), thioarenoic S-acid (e.g. thiobenzoic S-acid, etc.), and the like, in which more preferable example may be triphenyl($C_1$–$C_4$)alkanethiol, thio($C_1$–$C_4$)alkanoic S-acid and thio($C_6$–$C_{10}$)arenoic S-acid, and the most preferable one may be thiobenzoic S-acid.

In case that the compound (V) may be ar(lower)alkanethiol, the starting compound (IV) of the present reaction is preferably used in a form of its reactive derivative at the hydroxy group, and in such a case, this reaction is usually carried out in the presence of an organic or inorganic base such as those exemplified in the explanation of Process 1.

In case that suitable example of compound (V) may be thio(lower)alkanoic S-acid or thioarenoic S-acid, this reaction is preferably carried out in the presence of a conventional condensing agent such as combination of triarylphosphine (e.g. triphenylphosphine, etc.) and di(lower)alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, tetrahydrofuran, etc., or a mixture thereof.

The reaction temperature is not critical and the reaction is usually carried out under from cooling to warming.

In this method, the configuration on the carbon atom substituted with the hydroxy group of the compound (IV) is inverted in the compound (III-a).

(B) Method B

The compound (III) or salts thereof can be prepared by subjecting the compound (III-a) or salts thereof to elimination reaction of the mercapto-protective group.

This elimination reaction can be carried out by a conventional method as described below, which can be selected according to the kind of mercaptoprotective group to be eliminated.

In case that the protective groups may be ar(lower)alkyl group, it can generally be eliminated by treating, for example, with a silver compound (e.g. silver nitrate, silver carbonate, etc.).

The reaction with the silver compound as stated above is preferably carried out in the presence of an organic base (e.g. pyridine, etc.).

The resultant silver salt of compound (III) can be transformed into its alkali metal salt, if necessary, by reacting with alkali metal halide (e.g. sodium iodide, potassium iodide, etc.).

Further, in case that the protective groups may be acyl group, it can generally be eliminated by solvolysis such as hydrolysis using an acid or base, alcoholysis using a base, and the like.

Suitable acid or base used in these reactions may be the same such as those given in the explanation of hydrolysis of the Process 2.

The hydrolysis is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

The object derivatives (I), and the compounds (III) and (III-a) obtained according to the Processes 1 to 5, and Methods A and B as explained above can be isolated and purified in a conventional manner, for example, extraction, precipitation, fractional crystallization, recrystallization, chromatography, and the like.

The object derivatives (I) and the pharmaceutically acceptable salts thereof of the present invention are novel and exhibit high antimicrobial activity, inhibiting the growth of a wide variety of pathogenic microorganisms, and further, are very stable against Dehydropeptidase and show high urinary excretion, therefore have high potential for the treatment of various infectious diseases.

In the present invention, the object derivatives (I) possessing more potent antimicrobial activity can be represented by the following formula:

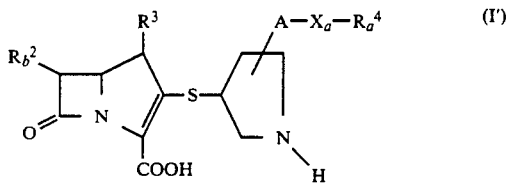

in which
$R_b^2$, $R^3$ and A are each as defined above,
$R_a^4$ is lower alkyl having suitable substituent(s), heterocyclic group optionally substituted by suitable substituent(s), or lower alkylsulfonyls and
$X_a$ is sulfur, oxygen or imino, provided that when X is oxygen, then $R^4$ is not "protected or unprotected ureido(lower)alkyl",
and pharmaceutically acceptable salts thereof.

Particularly, the compounds (I) possessing the most potent antimicrobial activity can be represented by the following formula:

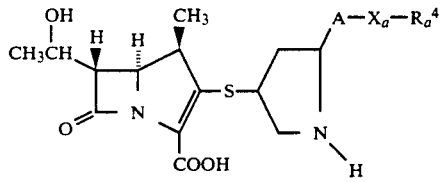

in which $R_a^4$, A and $X_a$ are each as defined above, and pharmaceutically acceptable salts thereof.

Now, in order to show the utility of the object derivatives (I), the test data on antimicrobial activity of the representative compound of the object derivatives (I) of this invention is shown in the following.

in vitro Antimicrobial Activity Test Method in vitro Antimicrobial Activity was determined by the two-fold agar-plate dilution method as described below.

One loopful of an overnight culture of a test strain in Trypticase-soy broth ($10^6$ visible cells per ml) was streaked on heart infusion agar (HI-agar) containing graded concentrations of the test compound, and the minimal inhibitory concentration (MIC) was expressed in terms of μg/ml after incubation at 37° C. for 20 hours.

Test Compound(1)
(4R,5S,6S)-3-[(2S,4S)-2-(Difluoromethyl)thiomethyl-pyrrolidin-4-ylthio]-6-[(1R)-1-hydroxyethyl]-4-methyl-7-oxo-1-azabicyclo[3.2.0]hept-2-ene-2-carboxylic acid.

| Test Result (1): | |
|---|---|
| Test Strain | MIC (μg/ml) |
| Staphylococcus aureus 3004 | 0.39 |

Test Compound (2)
(4R,5S,6S)-6-[(1R)-1-Hydroxyethyl]-3-[(2S,4S)-2-(2-hydroxyethyloxymethyl)pyrrolidin-4-yl]thio-4-methyl-7-oxo-1-azabicyclo[3.2.0]hept-2-ene-2-carboxylic acid.

| Test Result (2): | |
|---|---|
| Test Strain | MIC (μg/ml) |
| Pseudomonas aeruginosa 26 | 0.39 |

For therapeutic administration, the object compounds (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compounds (I) may vary from and also depend upon the age, conditions of the patient, a kind of diseases, a kind of the compounds (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compounds (I) of the present invention may be used in treating diseases infected by pathogenic microorganisms.

The following Preparations and Examples are given for the purpose of illustrating this invention in more detail.

PREPARATION 1

To a solution of (2S,4R)-4-t-butyldimethylsilyloxy-2-methanesulfonyloxymethyl-1-(4-nitrobenzyloxycarbonyl)pyrrolidine (5.21 g) in N,N-dimethylformamide (52 ml) was added potassium thioacetate (1.83 g) and the mixture was stirred at 50°-60° C. for 1 hour. The reaction mixture was poured into ice-water (150 ml) and extracted 3 times with ethyl acetate (50 ml). The extracts were combined, washed with saturated aqueous sodium chloride, dried over anhydrous magnesium sulfate, and concentrated under reduced pressure to give a residue. The residue was subjected to a column chromatography on silica gel (150 g) and eluted with a mixture of n-hexane and ethyl acetate (3:1, V/V). The fractions containing the desired compound were collected and evaporated in vacuo to give (2S,4R)-2-acetylthiomethyl-4-t-butyldimethylsilyloxy-1-(4nitrobenzyloxycarbonyl)pyrrolidine (4.70 g).

IR (Neat): 1710–1700, 1610, 1530, 1405, 1350,1260, cm$^{-1}$

NMR (CDCl$_3$, δ): 0.06 (6H, s), 1.84 (9H, s), 2.35 (3H, s), 5.26 (2H, s), 7.54 (2H, d, J=8 Hz), 8.22 (2H, d, J=8 Hz)

PREPARATION 2-1

To a solution of (2S,4R)-2-acetylthiomethyl-4-t-butyldimethylsilyloxy-1-(4-nitrobenzyloxycarbonyl)-pyrrolidine (2 g) in methanol (20 ml) was added 28% sodium methoxide-methanol solution (0.98 ml) with stirring at 2°–5° C. for 10 minutes. Chlorodifluoromethane was bubbled into the reaction mixture at 40° C. for 4 hours and under refluxing for 2 hours. After neutralizing the solution with glacial acetic acid (0.6 ml), the solution was concentrated under reduced pressure. To the residue were added ethyl acetate (60 ml) and saturated aqueous sodium hydrogen carbonate (30 ml). The separated organic layer was washed in turn with saturated aqueous sodium hydrogen carbonate and saturated aqueous sodium chloride, dried over anhydrous magnesium sulfate, and evaporated in vacuo. The resulting residue was subjected to a column chromatography on silica gel (100 g) and eluted with a mixture of n-hexane and ethyl acetate (5:1, V/V). The fractions containing the desired compound were collected and evaporated in vacuo to give (2S,4R)-4-t-butyldimethylsilyloxy-2-(difluoromethyl)thiomethyl-1-(4-nitrobenzyloxycarbonyl)pyrrolidine (1.38 g).

IR (Neat): 1710–1690, 1610, 1530, 1400 cm$^{-1}$

NMR (CDCl$_3$, δ): 0.05 (6H, s), 0.86 (9H, s), 1.80–2.15 (2H, m), 5.25 (2H, s), 7.25 (1H, t, J=28 Hz), 7.51 (2H, d, J=8 Hz), 8.21 (2H, d, J=8 Hz)

PREPARATION 2-2

To a solution of (2S,4R)-2-acetylthiomethyl-4-t-butyldimethylsilyloxy-1-(4-nitrobenzyloxycarbonyl)-pyrrolidine (2.0 g) in methanol (20 ml) was added 28% sodium methoxide-methanol solution (0.98 ml) under an atmosphere of nitrogen at 0° C. After stirring at the same temperature for 10 minutes, to this reaction mixture was added 2-iodoacetamide (1.02 g) under the same condition. The mixture was stirred at ambient temperature for 3 hours The reaction mixture was concentrated under reduced pressure. The resulting residue was dissolved in ethyl acetate (100 ml). The solution was washed with saturated aqueous sodium hydrogen carbonate and saturated sodium chloride successively, dried over anhydrous magnesium sulfate, and evaporated in vacuo to give (2S,4R)-4-t-butyldimethylsilyloxy-2-(carbamoylmethyl)thiomethyl-1-(4nitrobenzyloxycarbonyl)pyrrolidine (2.11 g).

IR (Neat): 1705 (sh), 1690–1675, 1610, 1525, 1350, 1260 cm$^{-1}$

NMR (CDCl$_3$, δ): 0.06 (6H, s), 0.86 (9H, s), 1.88–2.22 (2H, m), 3.22 (2H, s), 5.25 (2H, s), 7.53 (2H, d, J=8 Hz), 8.25 (2H, d, J=8 Hz)

PREPARATION 3-1

To a solution of (2S,4R)-4-t-butyldimethylsilyloxy-2-(difluoromethyl)thiomethyl-1-(4-nitrobenzyloxycarbonyl)pyrrolidine (1.36 g) in methanol (30 ml) was added conc. hydrochloric acid (0.47 ml) at ambient temperature and the mixture was stirred at the same temperature for 1 hour. The reaction mixture was concentrated under reduced pressure. The resulting residue was dissolved in ethyl acetate (50 ml). The solution was washed in turn with saturated aqueous sodium hydrogen carbonate and saturated aqueous sodium chloride dried over anhydrous magnesium sulfate, and concentrated under reduced pressure to give (2S,4R)-2-(difluoromethyl)thiomethyl-4-hydroxy-1-(4-nitrobenzyloxycarbonyl)pyrrolidine (1.03 g).

IR (Neat): 3450–3400, 1710–1690, 1610, 1525, 1410 cm$^{-1}$

NMR (CDCl$_3$, δ): 1.52–1.95 (2H, m), 2.75–3.50 (2H, m), 4.05–4.70 (2H, m), 5.23 (2H, s), 6 80 (1H, t, J=56 Hz), 7.53 (2H, d, J=8 Hz), 8.22 (2H, d, J=8 Hz)

EI Mass: 278 (M+ −84), 265 (M+ −97)

PREPARATION 3-2

To a solution of (2S,4R)-4-t-butyldimethylsilyloxy-2-(carbamoylmethyl)thiomethyl-1-(4-nitrobenzyloxycarbonyl)pyrrolidine (2.10 g) in methanol (40 ml) was added conc. hydrochloric acid (0.72 ml) at ambient temperature After stirring at the same temperature for 1 hour, this reaction mixture was concentrated under reduced pressure to give a residue. The residue was dissolved in ethyl acetate (60 ml). The solution was washed with saturated aqueous sodium hydrogen carbonate and saturated aqueous sodium chloride successively, dried over anhydrous magnesium sulfate, and evaporated in vacuo to give a residue. The residue was washed with a mixture of ethyl acetate (30 ml) and diisopropyl ether (15 ml). The resulting precipitates were collected by filtration and air-dried to give (2S,4R)-2-(carbamoylmethyl)thiomethyl-4-hydroxy-1-(4-nitrobenzyloxycarbonyl)pyrrolidine (1.08 g).

mp: 118°–119° C.

IR (Neat): 1710, 1610, 1525, 1405, 1350, 1210 cm$^{-1}$

NMR (DMSO-d$_6$, δ): 1.80–2.15 (2H, m), 2.65–3.05 (2H, m), 3.09 (2H, s), 3.30–3.55 (2H, m), 3.85–4.50 (2H, m), 4.96 (1H, d, J=4 Hz), 5.24 (2H, s), 7.66 (2H, d, J=8 Hz), 8.26 (2H, d, J=8 Hz)

Mass: 369 (M+), 278 (M+ −91)

PREPARATION 4

To a solution of (2S,4R)-2-(difluoromethyl)thiomethyl-4-hydroxy-1-(4-nitrobenzyloxycarbonyl)pyrrolidine (1.01 g) and triphenylphosphine (1.1 g) in tetrahydrofuran (20 ml) was added dropwise a solution of diethyl azodicarboxylate (0.66 ml) in tetrahydrofuran (3 ml) at −10° C. to −5° C. with stirring. The mixture was stirred at the same temperature for 30 minutes. To the solution was added thiobenzoic S-acid (0.49 ml) at the same temperature and the mixture was stirred under ice-cooling for 2 hours. The reaction mixture was concentrated under reduced pressure. The resulting residue was dissolved in ethyl acetate (60 ml). The solution was washed with saturated aqueous sodium hydrogen carbonate and saturated aqueous sodium chloride successively, dried over anhydrous magnesium sulfate, and evaporated in vacuo. The resulting residue was chromatographed on silica gel (100 g) eluting with a mixture of n-hexane and ethyl acetate (3.1 , V/V). The fractions containing the desired compound were collected and evaporated in vacuo to give (2S,4S)-4-benzoylthio-2-(difluoromethyl)thiomethyl-1-(4-nitrobenzyloxycarbonyl)pyrrolidine (1.01 g).

IR (Neat): 1710, 1665, 1610, 1525, 1405, 1350, 1210 cm$^{-1}$

NMR (CDCl$_3$, δ): 1.45–1.75 (2H, m), 3.20–3.75 (3H, m), 3.85–4.45 (5H, m), 5.25 (2H, s), 6.68 (1H, t, J=56 Hz), 7.40–7.65 (4H, m), 7.80–8.05 (2H, m), 8.23 (2H, d, J=8 Hz)

PREPARATION 5

To a solution of (2S,4R)-2-(carbamoylmethyl)thiomethyl-4-hydroxy-1-(4-nitrobenzyloxycarbonyl)pyrrolidine (1.06 g) and triethylamine (0.92 ml) in a mixture of tetrahydrofuran (40 ml) and N,N-dimethylformamide (5 ml) was added dropwise methanesulfonyl chloride (0.44 ml) under ice-cooling. The mixture was stirred at 2° C. for 1 hour and then allowed to stand at ambient temperature for 1 hour. To the reaction mixture was added ethyl acetate (50 ml). The solution was washed with saturated aqueous sodium hydrogen carbonate and saturated aqueous sodium chloride successively, dried over anhydrous magnesium sulfate, and evaporated in vacuo to give (2S,4R)-2-(carbamoylmethyl)thiomethyl-4-methanesulfonyloxy-1-(4-nitrobenzyloxycarbonyl)pyrrolidine (1.70 g).

IR (Neat): 1710–1660, 1610, 1525, 1350, 1175 cm$^{-1}$

NMR (CDCl$_3$, δ): 2.05–2.60 (3H, m), 3.03 (3H, s), 5.25 (2H, s), 7.53 (2H, d, J=8 Hz), 8.25 (2H, d, J=8 Hz)

PREPARATION 6

To a suspension of sodium hydride (62.8% in oil) (0.22 g) in N,N-dimethylformamide (5 ml) was added dropwise thiobenzoic S-acid (0.66 ml) under ice-cooling. After stirring under the same condition for 30 minutes, this solution was added to a solution of (2S,4R)-2-(carbamoylmethyl)thiomethyl-4-methanesulfonyloxy-1-(4-nitrobenzyloxycarbonyl)pyrrolidine (1.68 g) in N,N-dimethylformamide (20 ml) at ambient temperature. The mixture was stirred at 70°–80° C. for 1 hour. The reaction mixture was poured into ice-water (50 ml) and extracted twice with ethyl acetate (50 ml). The organic layer was washed with saturated aqueous sodium chloride, dried over anhydrous magnesium sulfate and evaporated in vacuo t.o give a residue. The residue was chromatographed on silica gel (100 g) eluting with a mixture of dichloromethane and acetone (5:1, V/V). The fractions containing the desired compound were collected and evaporated in vacuo to give (2S,4S)-4-benzoylthio-2-(carbamoylmethyl)thiomethyl-1-(4-nitrobenzyloxycarbonyl)pyrrolidine (0.87 g).

IR (Neat): 1710 (sh), 1690–1660, 1610, 1525, 1350, 1210 cm$^{-1}$

NMR (CDCl$_3$, δ): 2.40–3.15 (4H, m), 3.21 (2H, s), 3.75–4 50 (3H, m), 5.23 (2H, s), 7.20–7.75 (5H, m), 7.93 (2H, d, J=8 Hz), 8.23 (2H, d, J=8 Hz)

PREPARATION 7-1

To a solution of (2S,4S)-4-benzoylthio-2-(difluoromethyl)thiomethyl-1-(4-nitrobenzyloxycarbonyl)pyrrolidine (1.0 g) in a mixture of methanol (10 ml) and tetrahydrofuran (10 ml) was added 28% sodium methoxide-methanol solution (0.52 ml) under an atmosphere of nitrogen at 2°–5° C. The mixture was stirred at the same temperature for 30 minutes. To the reaction mixture was added glacial acetic acid (1 ml) and the mixture was concentrated under reduced pressure. The resulting residue was dissolved in ethyl acetate (50 ml). The solution was washed twice with saturated aqueous sodium chloride, dried over anhydrous magnesium sulfate and evaporated in vacuo. The resulting residue was chromatographed on silica gel (80 g) eluting with a mixture of n-hexane and ethyl acetate (2:1, V/V). The fractions containing the desired compound were collected and concentrated under reduced pressure to give (2S,4S)-2-(difluoromethyl)thiomethyl-4-mercapto-1-(4-nitrobenzyloxycarbonyl)pyrrolidine (0.58 g).

IR (Neat): 1710–1700, 1610, 1525, 1410, 1350, 1205 cm$^{-1}$

NMR (CDCl$_3$, δ): 1.40–2.05 (5H, m), 2.35–2.75 (1H, m), 3.05–3.50 (4H, m), 3.85–4.40 (2H, m), 5.25 (2H, s), 6.80 (1H, t, J=56 Hz), 7.53 (2H, d, J=8 Hz), 8.25 (2H, d, J=8 Hz)

EI Mass: 281 (M$^+$ −97)

PREPARATION 7-2

To a solution of (2S,4S)-4-benzoylthio-2-(carbamoylmethyl)thiomethyl-1-(4-nitrobenzyloxycarbonyl)pyrrolidine (0.86 g) in methanol (20 ml) was added 28% sodium methoxide-methanol solution (0.44 ml) at 0°–2° C. under an atmosphere of nitrogen. The mixture was stirred under the same condition for 30 minutes. To the reaction mixture was added glacial acetic acid (0.8 ml) and the mixture was concentrated under reduced pressure to give a residue. The residue was dissolved in ethyl acetate (50 ml). The solution was washed with saturated aqueous sodium chloride, dried over anhydrous magnesium sulfate and evaporated in vacuo. The resulting residue was chromatographed on silica gel (100 g) eluting with a mixture of dichloromethane and acetone (5:1, V/V). The fractions containing the desired compound were collected and evaporated in vacuo to give (2S,4S)-2-(carbamoylmethyl)thimethyl-4-mercapto-1-(4-nitrobenzyloxycarbonyl)pyrrolidine (0.47 g).

IR (Neat): 1710, 1630, 1520, 1350, 1205 cm$^{-1}$

NMR (CDCl$_3$, δ): 1.75–1.95 (3H, m), 2.45–2.85 (1H, m), 2.90–3.15 (2H, m), 3.21 (2H, s), 3.25–3.50 (2H, m), 3.85–4.30 (2H, m), 5.24 (2H, s), 7.55 (2H, d, J=8 Hz), 8.27 (2H, d, J=8 Hz)

PREPARATION 8

To a solution of (3S)-3-mercapto-1-(4-nitrobenzyloxycarbonyl)pyrrolidine (1.36 g) in methanol (5 ml) was added 28% sodium methoxide-methanol solution (0.97 ml) under ice-cooling and the mixture was stirred at the same temperature for 10 minutes. This solution was added to a solution of (2S,4R)-4-t-butyldimethylsilyloxy-2-methanesulfonyloxymethyl-1-(4-nitrobenzyloxycarbonyl)pyrrolidine (2 g) in methanol (20 ml). The mixture was stirred at ambient temperature for 3 hours and then at 50°–60° C. for 5 hours. The reaction mixture was evaporated in vacuo to give a residue. The residue was dissolved in ethyl acetate (50 ml). The solution was washed with saturated aqueous sodium chloride, dried over magnesium sulfate and evaporated in vacuo. The resulting residue was chromatographed on silica gel (100 g) eluting with a mixture of n-hexane and ethyl acetate (2:1 v/v). The fractions containing the desired compound were collected and evaporated in vacuo to give (2S,4R)-4-t-butyldimethylsilyloxy-1-(4-nitrobenzyloxycarbonyl)-2-[{(3S)-1-(4-nitrobenzyloxycarbonyl)pyrrolidin-3-ylthio}methyl]pyrrolidine (1.95 g).

IR (Neat): 1715–1700, 1610, 1525, 1350, 1255 cm$^{-1}$

PREPARATION 9

To a solution of (2S,4R)-4-t-butyldimethylsilyloxy-1-(4-nitrobenzyloxycarbonyl)-2-[{(3S)-1-(4-nitrobenzyloxycarbonyl)pyrrolidin-3-ylthio}methyl]pyrrolidine (1.94 g) in a mixture of methanol (20 ml) and tetrahydrofuran (20 ml) was added conc. hydrochloric acid (0.48 ml) at ambient temperature and the mixture was stirred at ambient temperature for 1 hour. The reaction mixture was evaporated in vacuo to give a residue. The residue was dissolved in ethyl acetate (50 ml) and the solution was washed three times with saturated aqueous sodium hydrogen carbonate (50 ml) and saturated aqueous sodium chloride (20 ml) successively, dried over magnesium sulfate, and evaporated in vacuo. The resulting residue was chromatographed on silica gel (100 g) eluting with a mixture of dichloromethane and acetone (5:1 v/v) to give (2S,4R)-4-hydroxy-1-(4-nitrobenzyloxycarbonyl)-2-[{(3S)-1-(4-nitrobenzyloxycarbonyl)pyrrolidin-3-ylthio}-methyl]pyrrolidine (1.10 g).

IR (Neat): 1710–1685, 1610, 1525, 1345 cm$^{-1}$

NMR (CDCl$_3$, δ): 1.65–2.40 (4H, m), 2.70–3.15 (2H, m), 3.15–3.90 (7H, m), 4.10–4.40 (1H, m), 4.40–5.60 (1H, m), 5.22 (4H, s), 7.56 (4H, d, J=8 Hz), 8.23 (4H, d, J=8 Hz)

PREPARATION 10

To a suspension of sodium borohydride (0.20 g) in tetrahydrofuran (10 ml) was added dropwise boron trifluoride etherate (2.25 ml) under ice-cooling. The mixture was stirred at the same temperature for 10 minutes. To the solution obtained above was added (2S,4R)-2-(carbamoylmethylthio)methyl-4-hydroxy-1-(4-nitrobenzyloxycarbonyl)pyrrolidine (0.92 g) under ice-cooling. The mixture was stirred at ambient temperature for 3 hours. To the reaction mixture was added methanol (5 ml) and the mixture was evaporated in vacuo. The resulting residue was dissolved in a mixture of methanol (10 ml) and conc. hydrochloric acid (1 ml). The solution was allowed to stand overnight at ambient temperature The reaction mixture was evaporated in vacuo to give (2S,4R)-2-(2-aminoethylthio)methyl-4-hydroxy-1-(4-nitrobenzyloxycarbonyl)pyrrolidine hydrochloride. The compound obtained above was dissolved in a mixture of ethyl acetate (40 ml) and saturated aqueous sodium hydrogen carbonate (80 ml) The separated aqueous layer was washed with ethyl acetate (40 ml). To the aqueous layer was added ethyl acetate (40 ml) and the mixture was cooled in ice-bath. To the mixture obtained above was added dropwise a solution of 4-nitrobenzyloxycarbonyl chloride (0.54 g) in tetrahydrofuran (10 ml) with stirring under ice-cooling, while the pH was kept between 8 and 9 with 1N aqueous sodium hydroxide. The solution was stirred under the same condition for additional 1 hour. The organic layer of the reaction mixture was separated, washed with saturated aqueous sodium chloride, dried over magnesium sulfate and evaporated in vacuo. The resulting residue was chromatographed on silica gel (50 g) eluting with a mixture of chloroform and methanol (9:1 v/v). The fractions containing the desired compound were collected and concentrated under reduced pressure to give (2S,4R)-4-hydroxy-1-(4-nitorbenzyloxycarbonyl)-2-[{2-(4-nitrobenzyloxycarbonylamino)ethylthio}methyl]pyrrolidine (1.01 g).

IR (Neat): 1710–1700, 1690, 1610, 1530–1515, 1350 cm$^{-1}$

NMR (CDCl$_3$, δ): 2.50–2.95 (3H, m), 3.20–3.70 (4H, m), 5.15–5.28 (4H, m), 7.53 (4H, br d, J=8 Hz), 8.23 (4H, d, J=8 Hz)

PREPARATION 11-1

(2S,4S)-4-Benzoylthio-1-(4-nitorbenzyloxycarbonyl)-2-[{(3S)-1-(4-nitrobenzyloxycarbonyl)pyrrolidin-3-ylthio}methyl]pyrrolidine (0.75 g) was obtained by reacting (2S,4R)-4-hydroxy-1-(4-nitrobenzyloxycarbonyl)-2-[{(3S)-1-(4-nitrobenzyloxycarbonyl)pyrrolidin-3-ylthio}methyl]pyrrolidine (1.08 g) with thiobenzoic S-acid (0.34 ml) in substantially the same manner as that of Preparation 4.

NMR (CDCl$_3$, δ): 1.75–2.40 (2H, m), 3.20–4.55 (9H, m), 5.27 (4H, s), 7.40–7.70 (7H, m), 7.85–8.10 (2H, m), 8.25 (4H, d, J=8 Hz)

PREPARATION 11-2

(2S,4S)-4-Benzoylthio-1-(4-nitrobenzyloxycarbonyl)-2-[{2-(4-nitrobenzyloxycarbonylamino)ethylthio}methylpyrrolidine (0.89 g) was obtained by reacting (2S,4R)-4-hydroxy-1-(4-nitrobenzyloxycarbonyl)-2-[{2-(4-nitrobenzyloxycarbonylamino)ethylthio}methyl]pyrrolidine (1.0 g) with thiobenzoic S-acid (0.33 ml) in substantially the same manner as that of Preparation 4.

IR (Neat): 1725–1705, 1680–1660, 1610, 1530–1510 cm$^{-1}$

NMR (CDCl$_3$), δ): 2.40–3.10 (5H, m), 3.15–3.60 (2H, m), 5.15–5.35 (4H, m), 7.35–7.70 (7H, m), 7.75–8.05 (2H, m), 8.22 (4H, br d, J=8 Hz)

PREPARATION 12-1

(2S,4S)-4-Mercapto-1-(4-nitrobenzyloxycarbonyl)-2-[{(3S)-1-(4-nitrobenzyloxycarbonyl)pyrrolidin-3-ylthio}methyl]pyrrolidine (0.42 g) was obtained by reacting (2S,4S)-4-benzoylthio-1-(4-nitrobenzyloxycarbonyl)-2-[{(3S)-1-(4-nitrobenzyloxycarbonyl)pyrrolidin-3-ylthio}methyl]pyrrolidine (0.73 g) with 28% sodium methoxide-methanol solution (0.27 ml) in substantially the same manner as that of Preparation 7-1).

IR (Neat): 1720–1690, 1605, 1530–1515 cm$^{-1}$

NMR (CDCl$_3$, δ): 3.90–4.20 (2H, m), 5.25 (4H, s), 7.55 (4H, d, J=8 Hz), 8.26 (4H, d, J=8 Hz)

PREPARATION 12-2

(2S,4S)-4-Mercapto-1-(4-nitrobenzyloxycarbonyl)-2-[{2-(4-nitrobenzyloxycarbonylamino)ethylthio}methyl]pyrrolidine (0.48 g) was obtained by reacting (2S,4S)-4-benzoylthio-1-(4-nitrobenzyloxycarbonyl)-2-[{2-(4-nitrobenzyloxycarbonylamino)ethylthio}methyl]pyrrolidine (0.88 g) with 28% sodium methoxide-methanol solution (0.34 ml) in substantially the same manner of Preparation 7-1).

IR (Neat): 1710–1700, 1610, 1530–1520, 1350 cm$^{-1}$

NMR (CDCl$_3$, δ): 1.60–2.00 (2H, m), 2.30–3.65 (8H, m), 3.80–4.35 (2H, m), 5.20 (4H, s), 7.50 (4H, d, J=8 Hz), 8.21 (4H, d, J=8 Hz)

SI Mass: 551 (M+), 369 (M+−182)

PREPARATION 13

To a solution of sodium borohydride (0.78 g) in tetrahydrofuran (25 ml) was added dropwise boron trifluoride dimethyl etherate (8.78 ml) with stirring under ice-cooling and the solution was stirred at the same temperature for 10 minutes. To this solution was added (2S,4R)-2-(carbamoylmethyl)thiomethyl-4-hydroxy-1-(4-nitrobenzyloxycarbonyl)pyrrolidine (2.53 g) and the mixture was stirred at ambient temperature for 4 hours. To the reaction mixture was added methanol (5 ml) and the mixture was filtered. The filtrate was evaporated in vacuo to give a residue. The residue was dissolved in methanol (30 ml). To the solution was added 10% hydrogen chloride-methanol solution (10 ml) and the mixture was allowed to stand overnight at ambient temperature. The reaction mixture was evaporated in vacuo to give a residue. The residue was dissolved in a mixture of tetrahydrofuran (30 ml) and water (15 ml). To the solution was added a solution of potassium cyanate (3.83 g) in water (10 ml) and the mixture was stirred at 50°-60° C. for 30 minutes. The reaction mixture was evaporated in vacuo. The resulting residue was chromatographed on silica gel (100 g) eluting with a mixture of chloroform and methanol (9:1, v/v). The fractions containing the desired compound were collected and evaporated in vacuo to give (2S,4R)-2-(2-ureidoethyl)thiomethyl-4-hydroxy-1-(4-nitrobenzyloxycarbonyl)pyrrolidine (1.73 g).

IR (Neat): 1690–1660, 1610, 1530, 1350 cm$^{-1}$

NMR (CDCl$_3$, δ): 1.80–2.38 (2H, m), 2.46–3.78 (8H, m), 4.00–4.60 (3H, m), 5.00 (2H, s), 5.23 (2H, s), 5.94 (1H, t, J=6 Hz), 7.56 (2H, d, J=8 Hz), 8.23 (2H, d, J=8 Hz)

PREPARATION 14

To a solution of (2S,4R)-2-aminomethyl-4-t-butyldimethylsilyloxy-1-(4-nitrobenzyloxycarbonyl)pyrrolidine (5 g) and triethylamine (1.87 ml) in N,N-dimethylformamide (50 ml) was dropwise added ethyl bromoacetate (1.49 ml) at ambient temperature with stirring. The mixture was stirred at 40° C. for 30 minutes and then allowed to stand at ambient temperature for 6 hours. The reaction mixture was poured into saturated aqueous sodium chloride (100 ml) and extracted twice with ethyl acetate (100 ml). The extract was washed with saturated aqueous sodium chloride, dried over magnesium sulfate and evaporated in vacuo. The resulting residue was subjected to a column chromatography on silica gel (100 g) eluting with a mixture of dichloromethane and acetone (20:1 v/v). The fractions containing the desired compound were collected and evaporated in vacuo to give (2S,4R)-4-t-butyldimethylsilyloxy-2-[(ethoxycarbonylmethyl)aminomethyl]-1-(4-nitrobenzyloxycarbonyl)pyrrolidine (3.52 g).

IR (Neat): 1740, 1710, 1610, 1530, 1350, 1260 cm$^{-1}$

NMR (CDCl$_3$, δ): 0.06 (6H, s), 0.83 (9H, s), 1.24 (3H, t, J=7 Hz), 1.88–2.20 (2H, m), 5.24 (2H, s) 7.40–7.65 (2H, m), 8.23 (2H, d, J=8 Hz)

PREPARATION 15

To a solution of (2S,4R)-4-t-butyldimethylsilyloxy-2-[(ethoxycarbonylmethyl)aminomethyl]-1-(4-nitrobenzyloxycarbonyl)pyrrolidine (3.51 g) and triethylamine (1.28 ml) in tetrahydrofuran (35 ml) was dropwise added a solution of 4-nitrobenzyloxycarbonyl chloride (1.60 g) in tetrahydrofuran (5 ml) under ice-cooling. The mixture was stirred at the same temperature for 1 hour. The reaction mixture was concentrated under reduced pressure. The resulting residue was dissolved in ethyl acetate (100 ml) and the solution was washed with saturated aqueous sodium chloride, dried over magnesium sulfate, and evaporated in vacuo. The resulting residue was subjected to a column chromatography on silica gel (100 g) eluting with a mixture of dichloromethane and acetone (40:1 v/v). The fractions containing the desired compound were collected and evaporated in vacuo to give (2S,4R)-4-t-butyldimethylsilyloxy-2-[N-ethoxycarbonylmethyl-N-(4-nitrobenzyloxycarbonyl)]aminomethyl-1-(4-nitrobenzyloxycarbonyl)pyrrolidine (3.32 g).

IR (Neat): 1750, 1710–1700, 1610, 1525, 1350, 1255 cm$^{-1}$

NMR (CDCl$_3$, δ): 0.03 (6H, s), 0.83 (9H, s), 1.10–1.35 (3H, m), 1.80–2.20 (2H, m), 3.35–3.75 (4H, m), 8.22 (4H, d, J=8 Hz)

PREPARATION 16

To a solution of (2S,4R)-4-t-butyldimethylsilyloxy-2-[N-ethoxycarbonylmethyl-N-(4-nitrobenzyloxycarbonyl)]-aminomethyl-1-(4-nitrobenzyloxycarbonyl)pyrrolidine (3.31 g) in methanol (20 ml) was added 3N ammonia in mathanol solution (16.4 ml) at ambient temperature. The mixture was allowed to stand overnight at the same temperature. The reaction mixture was evaporated in vacuo. The resulting residue was dissolved in ethyl acetate (60 ml) and the solution was washed with saturated aqueous sodium chloride, dried over magnesium sulfate and evaporated in vacuo to give (2S,4R)-4-t-butyldimethylsilyloxy-2-[N-carbamoylmethyl-N-(4-nitrobenzyloxycarbonyl)-]aminomethyl-1-(4-nitrobenzyloxycarbonyl)pyrrolidine (3.32 g).

IR (Neat): 1710–1700, 1610, 1530, 1350, 1250 cm$^{-1}$

NMR (CDCl$_3$, δ): 0.03 (6H, s), 0.83 (9H, s), 1.80–2.10 (2H, m), 5.22 (4H, s), 7.36–7.60 (4H, m), 8.22 (4H, d, J=8 Hz)

PREPARATION 17

(2S,4R)-2-[N-Carbamoylmethyl-N-(4-nitrobenzyloxycarbonyl)]aminomethyl-4-hydroxy-1-(4-nitrobenzyloxycarbonyl)pyrrolidine (2.30 g) was obtained by reacting (2S,4R)-4-t-butyldimethylsilyloxy-2-[N-carbamoylmethyl-N-(4-nitrobenzyloxycarbonyl)-]aminomethyl-1-(4-nitrobenzyloxycarbonyl)pyrrolidine (3.31 g) with conc. hydrochloric acid (0.85 ml) in substantially the same manner as that of Preparation 9.

IR (Neat): 1710–1690, 1610, 1530–1520, 1350 cm$^{-1}$

NMR (CDCl$_3$, δ): 1.90–2.28 (2H, m), 3.35–4.60 (10H, m) 5.20 (4H, s), 7.43 (2H, d, J=8 Hz), 7.51 (2H, d, J=8 Hz), 8.21 (4H, d, J=8 Hz)

PREPARATION 18-1

(2S,4S)-4-Benzoylthio-2-[N-carbamoylmethyl-N-(4-nitrobenzyloxycarbonyl)]aminomethyl-1-(4-nitrobenzyloxycarbonyl)pyrrolidine (2.43 g) was obtained by reacting (2S,4R)-2-[N-carbamoylmethyl-N-(4-nitrobenzyloxycarbonyl)]aminomethyl-4-hydroxy-1-(4-nitrobenzyloxycarbonyl)pyrrolidine (2.29 g) with triphenylphosphine (1.70 g) and diethyl azodicarboxylate (1.02 ml), and then with thiobenzoic S-acid (0.76 ml) in substantially the same manner as that of Preparation 4.

NMR (CDCl$_3$, δ): 1.85–2.32 (1H, m), 2.35–2.85 (1H, m), 5.20 (4H, s), 7.33–7.65 (7H, m), 7.85–8.00 (2H, m), 8.22 (4H, d, J=8H)

PREPARATION 18-2

(2S,4S)-4-Benzoylthio-2-(2-ureidoethyl)thiomethyl-1-(4-nitrobenzyloxycarbonyl)pyrrolidine (1.87 g) was obtained by reacting (2S,4R)-2-(2-ureidoethyl)thiomethyl-4-hydroxy-1-(4-nitrobenzyloxycarbonyl)pyrrolidine (1.71 g) with triphenylphosphine (1.69 g) and diethyl azodicarboxylate (1.01 ml), and then with thiobenzoic S-acid (0.76 ml) in substantially the same manner as that of Preparation 4.

IR (Neat): 1710–1650, 1530–1515, 1350–1340 cm$^{-1}$

NMR (CDCl$_3$, δ): 1.60–2.25 (2H, m), 2.40–3.60 (8H, m), 3.83–4.38 (3H, m), 4.45–4.80 (2H, m), 5.22 (2H, s), 5.35–5.65 (1H, m), 7.33–7.76 (5H, m), 7.95 (2H, dd, J=7, 2 Hz), 8.24 (2H, d, J=8 Hz)

PREPARATION 19-1

(2S,4S)-2-[N-Carbamoylmethyl-N-(4-nitrobenzyloxycarbonyl)]aminomethyl-4-mercapto-1-(4-nitrobenzyloxycarbonyl)pyrrolidine (1.46 g) was obtained by reacting (2S,4S)-4-benzoylthio-2-[N-carbamoylmethyl-N-(4-nitrobenzyloxycarbonyl)]aminomethyl-1-(4-nitrobenzyloxycarbonyl)pyrrolidine (2.42 g) with 28% sodium methoxide-methanol solution (0.93 ml) in substantially the same manner as that of Preparation 7-1).

IR (Neat) 1710–1790, 1610, 1530–1520 cm$^{-1}$

NMR (CDCl$_3$, δ): 1.63–2.00 (2H, m), 2.27–2.76 (1H, m), 3.00–3.50 (2H, m), 5.21 (4H, s), 7.33–7 66 (4H, m), 8.22 (4H, d, J=8 Hz)

PREPARATION 19-2

(2S,4S)-2-(2-Ureidoethyl)thiomethyl-4-mercapto-1-(4-nitrobenzyloxycarbonyl)pyrrolidine (1.07 g) was obtained by reacting (2S,4S)-4-benzoylthio-2-(2-ureidoethyl)thiomethyl-1-(4-nitrobenzyloxycarbonyl)pyrrolidine (1.85 g) with 28% sodium methoxide-methanol solution (0.89 ml) in substantially the same manner as that of Preparation 7-1).

IR (Neat): 1715–1655, 1610, 1530, 1350 cm$^{-1}$

NMR (CDCl$_3$, δ): 1.60–2 20 (2H, m), 2.40–3.70 (8H, m), 3.75–4.40 (2H, m), 4.60–4.90 (2H, m), 5.23 (2H, s), 5.30–5.60 (1H, m), 7.53 (2H, d, J=8 Hz), 8.25 (2H, d, J=8 Hz)

PREPARATION 20-1

A mixture of (2S,4R)-4-t-butyldimethylsilyloxy-2-hydroxymethyl-1-(4-nitrobenzyloxycarbonyl)pyrrolidine (10.0 g), methanol (100 ml) and 20% palladium hydroxide on carbon (0.5 g) was stirred under atmospheric pressure of hydrogen at ambient temperature for 3 hours. The catalyst was filtered off and the filtrate was concentrated under reduced pressure to give a syrup. To a solution of the syrup in a mixture of tetrahydrofuran (100 ml) and water (100 ml) was dropwise added a solution of chloroacetyl chloride (5.0 ml) in tetrahydrofuran (10 ml) under ice-cooling with stirring, keeping the pH between 8–9 with 4N aqueous sodium hydroxide. The mixture was stirred at the same condition for 2 hours and extracted with a mixture of ethyl acetate and tetrahydrofuran (1:1 V/V) (100 ml×5). The solution was dried over magnesium sulfate and concentrated under reduced pressure to give a syrup. The syrup was subjected to a column chromatography on silica gel (200 g) and eluted with a mixture of methanol and dichloromethane (1:99 V/V) to give (2S,4R)-4-t-butyldimethylsilyloxy-1-chloroacetyl-2-(hydroxymethyl)pyrrolidine (4.22 g).

IR (Neat): 3400, 1660–1630 cm$^{-1}$

NMR (CDCl$_3$, δ): 1.10 (6H, s), 1.90 (9H, s), 1.5–2.3 (3H, m), 3.3–3.9 (5H, m), 4.03 (2H, s), 4.1–4.5 (3H, m)

PREPARATION 20-2

(2S,4R)-1-(2-Bromo-2-methylpropionyl)-4-t-butyldimethylsilyloxy-2-(hydroxymethyl)pyrrolidine (3.70 g) was obtained by reacting (2S,4R)-4-t-butyldimethylsilyloxy-2-(hydroxymethyl)pyrrolidine (3.00 g) with 2-bromo-2-methylpropionyl bromide (1.95 ml) in substantially the same manner as that of Preparation 20-1).

mp : 77°–80° C.

IR (Nujol) : 1620 cm$^{-1}$

NMR (CDCl$_3$, δ) : 0.10 (6H, s), 0.90 (9H, s), 2.00 (6H, s)

PREPARATION 21-1

A solution of (2S,4R)-4-t-butyldimethylsilyloxy-1-chloroacetyl-2-(hydroxymethyl)pyrrolidine (4.20 g) in tetrahydrofuran (20 ml) was dropwise added to a suspension of sodium hydride (62.8% in oil suspension) (0.55 g) in tetrahydrofuran (60 ml) at 20°–30° C. and the mixture was stirred at 25°–30° C. for 3 hours. The mixture was concentrated under reduced pressure to give a syrup. A solution of the syrup in ethyl acetate (80 ml) was washed with water (100 ml), dried over magnesium sulfate and concentrated under reduced pressure to give a residue. The residue was subjected to a column chromatography on silica gel (30 g) and eluted with a mixture of methanol and chloroform (1:99 V/V) to give (6S,8R)-8-t-butyldimethylsilyloxy-2-oxo-1-aza-4-oxabicyclo[4.3.0]nonane (3.49 g).

mp : 81°–82° C.

IR (Nujol) : 1650 cm$^{-1}$

NMR (CDCl$_3$, δ) : 1.10 (6H, s), 1.90 (9H, s), 1.3–1.6 (1H, m), 1.8–2.1 (1H, m), 3.1–3.5 (2H, m), 3.8–4.3 (5H, m), 4.4–4.6 (1H, m)

MS : 256 (M$^+$ − 15), 214

PREPARATION 21-2

(6S,8R)-8-t-butyldimethylsilyloxy-3,3-dimethyl-2-oxo-1-aza-4-oxabicyclo[4.3.0]nonane (1.18 g) was obtained by reacting (2S,4R)-1-(2-bromo-2-methylpropionyl-4-t-butyldimethylsilyloxy-2-(hydroxymethyl)pyrrolidine (3.70 g) with sodium hydride in substantially the same manner as that of Preparation 21-1.

mp : 40°–45° C.

IR (Nujol) : 1740 cm$^{-1}$

NMR (CDCl$_3$, δ) : 0.02 (6H, s), 0.85 (9H, s), 1.37 (3H, s), 1.43 (3H, s)

PREPARATION 22

A suspension of (6S,8R)-8-t-butyldimethylsilyloxy-2-oxo-1-aza-4-oxabicyclo[4.3.0]nonane (1.43 g) in 6N hydrochloric acid (14 ml) was heated for 3 hours under reflux. After cooling, the solution was washed with ethyl acetate (7 ml×2) and concentrated under reduced pressure to give (2S,4R)-2-(carboxymethyloxymethyl)-4-hydroxypyrrolidine hydrochloride.

PREPARATION 23

To a solution of the compound obtained in Preparation 22 in a mixture of water (30 ml) and tetrahydrofuran (30 ml) was dropwise added a solution of 4-nitrobenzyloxycarbonyl chloride (1.36 g) in tetrahydrofuran (6 ml) under ice-cooling with stirring, keeping the pH between 8–9 with 4N aqueous sodium hydroxide. The mixture was stirred under the same condition for 2 hours, adjusted to pH 2.5 with 6N hydrochloric acid and extracted with ethyl acetate (50 ml×2). The organic solution was combined, washed with brine, dried over magnesium sulfate and concentrated under reduced pressure to give a syrup. The syrup was subjected to a column chromatography on silica gel (20 g) and eluted with a mixture of methanol and chloroform (3:97 V/V) to give (2S,4R)-2-(carboxymethyloxymethyl)-4-hydroxy-1-(4-nitrobenzyloxycarbonyl)pyrrolidine (1.45 g).

IR (Neat) : 3600–3300, 1750–1680 cm$^{-1}$

NMR (DMSO-d$_6$, δ) : 1.8–2.2 (2H, m), 3.2–3.7 (4H, m), 3.98 (2H, s), 3.9–4.4 (2H, m), 5.20 (2H, s), 7.58 (2H, d, J=8.5 Hz), 8.18 (2H, d, J=8.5 Hz)

PREPARATION 24-1

A solution of (6S,8R)-8-t-butyldimethylsilyloxy-2-oxo-1-aza-4-oxabicyclo[4.3.0]nonane (20.0 g) in 6N hydrochloric acid (200 ml) was heated for 3 hours under reflux. After cooling, the solution was washed with ethyl acetate (100 ml) and concentrated under reduced pressure to give (2S,4R)-2-carboxymethyloxymethyl-4hydroxypyrrolidine. The compound obtained above was dissolved in a mixture of tetrahydrofuran (100 ml) and water (100 ml). To the solution was dropwise added a solution of benzyloxycarbonyl chloride (11.55 ml) in tetrahydrofuran (20 ml) under ice-cooling with stirring, keeping the pH between 8-9 with 4N aqueous sodium hydroxide. The mixture was stirred at the same condition for 1 hour and washed with ethyl acetate (100 ml×2). The aqueous solution was adjusted to pH 2 with 6N hydrochloric acid and ethyl acetate (150 ml) was added thereto. The organic layer was separated, washed with brine, dried over magnesium sulfate and concentrated under reduced pressure to give (2S,4R)-1-benzyloxycarbonyl-2-carboxymethyloxymethyl-4-hydroxypyrrolidine (19.95 g).

IR (CHCl$_3$) : 3450-3050, 1750-1660 cm$^{-1}$

NMR (CDCl$_3$, δ): 1.8-2.3 (2H, m), 3.4-3.9 (4H, m), 3.9-4.3 (3H, m), 4.3-4.6 (1H, m), 5.13 (2H, s), 7.34 (5H, s)

PREPARATION 24-2

(2S,4R)-2-(1-Carboxy-1-methylethyl)oxymethyl-4-hydroxy-1-(4-nitrobenzyloxycarbonyl)pyrrolidine (0.85 g) was obtained by reacting (6S,8R)-8-t-butyldimethylsilyloxy-3,3-dimethyl-2-oxo-1-aza-4-oxabicyclo[4.3.0]nonane (1.15 g) with hydrochloric acid and 4-nitrobenzyloxycarbonyl chloride successively in substantially the same manners as those of Preparations 22 and 23.

IR (Neat) : 1710-1675 cm$^{-1}$

NMR (CDCl$_3$, δ) : 1.39 (3H, s), 1.41 (3H, s), 1.95-2.20 (2H, m), 5.23 (2H, m), 7.48 (2H, d, J=8.5 Hz), 8.19 (2H, d, J=8.5 Hz)

PREPARATION 25-1

A solution of methanesulfonyl chloride (0.62 ml) in dichloromethane (2 ml) was dropwise added to a solution of (2S,4R)-2-(carboxymethyloxymethyl)-4-hydroxy-1-(4nitrobenzyloxycarbonyl)pyrrolidine (1.42 g) and triethylamine (1.4 ml) in dichloromethane (14 ml) at 0°-5° C., and the mixture was stirred at the same temperature for 1 hour. The mixture was poured into water (50 ml), adjusted to pH 2.5 with 6N hydrochloric acid and extracted with dichloromethane (50 ml×2). The organic layer was washed with brine, dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-2-(carboxymethyloxymethyl)-4-methanesulfonyloxy-1-(4-nitrobenzyloxycarbonyl)pyrrolidine (1.30 g).

IR (CHCl$_3$) : 1750, 1705 cm$^{-1}$

NMR (CDCl$_3$, δ) : 2.3-2.5 (2H, m), 3.03 (3H, s), 3.5-4.4 (5H, m), 4.08 (2H, s), 5.22 (2H, s), 5.2-5.4 (1H, m), 5.8-6.2 (1H, m), 7.48 (2H, d, J=8.5 Hz), 8.19 (2H, d, J=8.5 Hz)

PREPARATION 25-2

A solution of methanesulfonyl chloride (10 ml) in tetrahydrofuran (20 ml) was dropwise added to a solution of (2S,4R)-1-benzyloxycarbonyl-2-carboxymethyloxymethyl-4-hydroxypyrrolidine (19.95 g) and triethylamine (27 ml) in tetrahydrofuran (200 ml) at −10°∼5° C. and the mixture was stirred at the same temperature for 1 hour The mixture was poured into water (200 ml), adjusted to pH 2.5 with 6N hydrochloric acid and extracted with ethyl acetate (150 ml×2). The organic layer was washed with brine (200 ml×2), dried over magnesium sulfate and concentrated under reduced pressure to give (2S,4R)-1-benzyloxycarbonyl-2-carboxymethyloxymethyl-4methanesulfonyloxypyrrolidine (24.85 g).

IR (Neat) : 3500-3100, 1755-1650 cm$^{-1}$

PREPARATION 26-1

A solution of isobutyl chloroformate (0.60 g) in tetrahydrofuran (1 ml) was dropwise added to a solution of (2S,4R)-2-(carboxymethyloxymethyl)-4-methanesulfonyloxy-1-(4-nitrobenzyloxycarbonyl)pyrrolidine (1.28 g) and triethylamine (0.82 ml) in tetrahydrofuran (13 ml) at −10°∼−5° C., and the mixture was stirred at the same temperature for 30 minutes. The mixture was dropwise added to concentrated ammonia water (10 ml) at 0°-5° C. and the solution was stirred at the same temperature for 1 hour. The mixture was poured into water (50 ml) and extracted with chloroform (50 ml). The organic layer was dried over magnesium sulfate and concentrated under reduced pressure to give a syrup. The syrup was subjected to a column chromatography on silica gel (25 g) and eluted with a mixture of methanol and chloroform (2:98 V/V) to give (2S,4R)-2-(carbamoylmethyloxymethyl)4-methanesulfonyloxy-1-(4-nitrobenzyloxycarbonyl)pyrrolidine (1.00 g).

IR (Neat) : 1710-1670 cm$^{-1}$

NMR (CDCl$_3$, δ) : 2.2-2.6 (2H, m), 3.06 (3H, s), 3.5-4.5 (7H, m), 3.98 (2H, s), 5.2-5.5 (1H, m), 5.29 (1H, m), 7.55 (2H, d, J=8.5 Hz), 8.28 (2H, d, J=8.5 Hz)

PREPARATION 26-2

To a solution of (2S,4R)-1-benzyloxycarbonyl-2-carboxymethyloxymethyl-4-methanesulfonyloxypyrrolidine (3.80 g) in benzene (19 ml) was added thionyl chloride (0.90 ml) with stirring at ambient temperature and the mixture was stirred at the same temperature for one hour. To the mixture were added urea (1.80 g) and concentrated sulfuric acid (0.05 ml) successively. The mixture was heated under reflux for 5 hours. The reaction mixture was poured into ice-water (100 ml) and extracted with ethyl acetate (100 ml). The organic layer was dried over magnesium sulfate and concentrated under reduced pressure to give a syrup. The syrup was subjected to a column chromatography on silica gel (100 g) and eluted with a mixture of methanol and chloroform (1:99 V/V) to give (2S,4R)-1-benzyloxycarbonyl-4-methanesulfonyloxy-2-[(ureidocarbonylmethyl)oxymethyl]pyrrolidine (1.85 g).

mp : 120°-122° C.

IR (KBr) : 3500-3100, 1725-1685 cm$^{-1}$

NMR (CDCl$_3$, δ) : 3.00 (3H, s), 4.04 (2H, s), 5.17 (2H, s), 5.95 (1H, br s), 7.38 (5H, s), 8.03 (1H, br s), 8.85 (1H, br s)

EI MS : 429 (M ), 298, 254

PREPARATION 27

A solution of methanesulfonyl chloride (0.4 ml) in tetrahydrofuran (2 ml) was dropwise added to a solution of (2S,4R)-2-(1-carboxy-1-methylethyl)oxymethyl-4-hydroxy-1-(4-nitrobenzyloxycarbonyl)pyrrolidine (0.84 g) and triethylamine (1 ml) in tetrahydrofuran (8 ml) at $-10° \sim -5°$ C. and the mixture was stirred at the same condition for 30 minutes. The mixture was dropwise added to a 10% solution (20 ml) of ammonia in ethanol and the mixture was stirred at the same temperature for 1 hour. The mixture was concentrated under reduced pressure to give a residue. The residue was dissolved in ethyl acetate (50 ml), washed with water (50 ml), dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-2-(1-carbamoyl-1-methylethyl)oxymethyl-4-methanesulfonyloxy-1-(4-nitrobenzyloxycarbonyl)pyrrolidine (1.01 g).

IR (CHCl$_3$) : 1710–1685 cm$^{-1}$

NMR (CDCl$_3$, δ) : 1.37 (6H, s), 3.05 (3H, s), 5.24 (2H, s), 7.51 (2H, d, J=8.5 Hz), 8.23 (2H, d, J=8.5 Hz)

PREPARATION 28

To (2S,4R)-2-(carbamoylmethyl)oxymethyl-4-methanesulfonyloxy-1-(4-nitrobenzyloxycarbonyl)pyrrolidine (1.75 g) was added N,N-dimethylformamide dimethylacetal (1.75 ml) and the mixture was stirred at 70° C. for 3 hours. The mixture was poured into ethyl acetate, washed in turn with water and brine, and evaporated in vacuo. The oily residue was dissolved in acetic acid (30 ml) and to this solution was added hydrazine hydrate (0.32 ml) at room temperature. After stirring at the same temperature for 2 hours, the mixture was poured into a mixture of water and ethyl acetate. The organic layer was washed in turn with saturated aqueous sodium bicarbonate and brine, dried over magnesium sulfate and evaporated in vacuo. The oily residue was subjected to a column chromatography on silica gel eluting with a mixture of acetone and dichloromethane (1:4, V/V) to give (2S,4R)-4-methanesulfonyloxy-2-[(2H-1,2,4-triazol-3-ylmethyl)oxymethyl]pyrrolidine (1.47 g).

IR (CH$_2$Cl$_2$) : 1690–1710, 1610 cm$^{-1}$

NMR (CDCl$_3$, δ) : 3.07 (3H, s), 4.70 (2H, s), 5.1–5.4 (3H, m), 7.4–7.7 (2H, d, J=9 Hz), 8.21 (2H, d, J=9 Hz), 8.09 (1H, s)

PREPARATION 29

A solution of (2S,4R)-1-benzyloxycarbonyl-4-methanesulfonyloxy-2-[(ureidocarbonylmethyl)oxymethyl]pyrrolidine (3.00 g) in a mixture of methanol (30 ml) and tetrahydrofuran (60 ml) was hydrogenated under atmospheric pressure of hydrogen at ambient temperature for 5 hours in the presence of 20% palladium hydroxide on carbon (1 g). The catalyst was filtered off and the filtrate was concentrated under reduced pressure to give (2S,4R)-4-methanesulfonyloxy-2-[(ureidocarbonylmethyl)oxymethyl]pyrrolidine. To a solution of the compound obtained above in a mixture of tetrahydrofuran (20 ml) and water (20 ml) was dropwise added a solution of allyl chloroformate (0.82 ml) in tetrahydrofuran (2 ml) under ice-cooling with stirring, keeping the pH between 9–10 with 4N aqueous sodium hydroxide. The mixture was stirred at the same condition for 1 hour and extracted with ethyl acetate (50 ml). The organic layer was dried over magnesium sulfate and evaporated under reduced pressure to give a syrup. The syrup was subjected to a column chromatography on silica gel (15 g) and eluted with a mixture of methanol and chloroform (2:98 v/v) to give (2S,4R)-1-allyloxycarbonyl-4-methanesulfonyloxy-2-[(ureidocarbonylmethyl)oxymethyl]pyrrolidine (1.11 g).

IR (Neat) : 1720–1685 cm$^{-1}$

NMR (CDCl$_3$, δ) : 3.07 (3H, s), 4.10 (2H, s)

PREPARATION 30-1

A solution of (2S,4R)-2-(carbamoylmethyl)oxymethyl-4-methanesulfonyloxy-1-(4-nitrobenzyloxycarbonyl)pyrrolidine (0.98 g) in dimethylformamide (2 ml) was added to a reaction mixture of thioacetic S-acid (0.25 ml) and sodium hydride (62.8% in oil suspension) (0.11 g) in dimethylformamide (10 ml) in a nitrogen stream and the mixture was heated at 70°–75° C. for 3 hours. The mixture was poured into water (100 ml), extracted with ethyl acetate (50 ml×3), dried over magnesium sulfate and concentrated under reduced pressure to give a syrup. The syrup was subjected to a column chromatography on silica gel (20 g) and eluted with a mixture of methanol and chloroform (1:99 v/v) to give (2S,4S)-4-acetylthio-2-(carbamoylmethyl)oxymethyl-1-(4nitrobenzyloxycarbonyl)pyrrolidine (0.72 g).

IR (Neat) : 1715–1670 cm$^{-1}$

NMR (CDCl$_3$, δ) : 2.33 (3H, s), 3.72 (2H, d, J=5 Hz), 3.97 (2H, s), 5.20 (2H, s), 7.45 (2H, d, J=8.5 Hz), 8.18 (2H, d, J=8.5 Hz)

PREPARATION 30-2

(2S,4S)-4-Acetylthio-1-(4-nitrobenzyloxycarbonyl)-2-[(2H-1,2,4-triazol-3-ylmethyl)oxymethyl]pyrrolidine (1.18 g) was obtained by reacting (2S,4R)-4-methanesulfonyloxy-1-(4-nitrobenzyloxycarbonyl)-2-[{(2H-1,2,4-triazol-3-yl)methyl}oxymethyl]pyrrolidine (1.47 g) with thioacetic S-acid (0.36 ml) in substantially the same manner as that of Preparation 30-1).

IR (CH$_2$Cl$_2$) : 1690–1710, 1610 cm$^{-1}$

NMR (CDCl$_3$, δ) : 2.32 (3H, s), 3.1–3.4 (1H, m), 4.72 (2H, s), 5.24 (2H, s), 7.51 (2H, d, J=9 Hz), 8.09 (1H, s), 8.28 (2H, d, J=9 Hz)

PREPARATION 30-3

(2S,4S)-4-Acetylthio-1-allyloxycarbonyl-2-[(ureidocarbonylmethyl)oxymethyl]pyrrolidine (0.60 g) was obtained by reacting (2S,4R)-1-allyloxycarbonyl-4-methanesulfonyloxy-2-[(ureidocarbonylmethyl)oxymethyl]pyrrolidine (1.05 g) with thioacetic S-acid (0.44 ml) in substantially the same manner as that of Preparation 30-1)

IR (Neat) : 1730–1670 cm$^{-1}$

NMR (CDCl$_3$, δ) : 2.33 (3H, s), 4.06 (2H, s)

PREPARATION 30-4

(2S,4S)-4-Acetylthio-2-(1-carbamoyl-1-methylethyl)oxymethyl-1-(4-nitrobenzyloxycarbonyl)pyrrolidine (0.84 g) was obtained by reacting (2S,4R)-2-(1-carbamoyl-1-methylethyl)oxymethyl-4-methanesulfonyloxy-1-(4-nitrobenzyloxycarbonyl)pyrrolidine (0.95 g) in substantially the same manner as that of Preparation 30-1).

IR (Neat) : 1710–1675 cm$^{-1}$

NMR (CDCl$_3$, δ) : 1.40 (6H, s), 2.37 (3H, s), 5.23 (2H, s), 7.51 (2H, d, J=8.5 Hz), 8.24 (2H, d, J=8.5 Hz)

PREPARATION 31-1

To a solution of (2S,4S)-4-acetylthio-2-(carbamoylmethyl)oxymethyl-1-(4-nirobenzyloxycarbonyl)pyrrolidine (0.80 g) in methanol (16 ml) was added sodium methoxide (28% solution in methanol) (0.45 ml) at $-10° \sim 5°$ C. in a nitrogen stream and the mixture was stirred at the same condition for 0.5 hour. To the mixture was added glacial acetic acid (0.15 ml) at −10°∼0° C. The mixture was concentrated under reduced pressure to give a residue. The residue was dissolved in ethyl acetate (40 ml). The solution was washed with water (40 ml), dried over magnesium sulfate and concentrated under reduced pressure to give a syrup. The syrup was subjected to a column chromatography on a silica gel (20 g) and eluted with a mixture of methanol and chloroform (1:99 v/v) to give (2S,4S)-2-(carbamoylmethyl)oxymethyl-4-mercapto-1-(4-nitrobenzyloxycarbonyl)pyrrolidine (0.60 g).

IR (Neat) : 1710–1670 cm$^{-1}$

NMR (CDCl$_3$, δ) : 3.96 (2H, s), 5.20 (2H, s), 7.48 (2H, d, J=8.5 Hz), 8.20 (2H, d, J=8 Hz)

PREPARATION 31-2

(2S,4S)-4-Mercapto-1-(4-nitrobenzyloxycarbonyl)-2-[(2H-1,2,4-triazol-3-yl)methyloxymethyl]pyrrolidine (1.0 g) was obtained by reacting (2S,4S)-4-acetylthio-1-(4-nitrobenzyloxycarbonyl)-2-[{(2H-1,2,4-triazol-3-yl)methyl}oxymethyl]pyrrolidine (1.18 g) with sodium methoxide (28% solution in methanol) (0.83 ml) in substantially the same manner as that of Preparation 31-1).

IR (CH$_2$Cl$_2$) : 1690–1710, 1610 cm$^{-1}$

NMR (CDCl$_3$, δ) : 4.72 (2H, s), 5.23 (2H, s), 7.52 (2H, d, J=9 Hz), 8.08 (1H, s), 8.27 (2H, d, J=9 Hz)

PREPARATION 31-3

(2S,4S)-1-Allyloxycarbonyl-4-mercapto-2-(ureidocarbonylmethyl)oxymethylpyrrolidine (0.36 g) was obtained by reacting (2S,4S)-4-acetylthio-1-allyloxycarbonyl-2-[(ureidocarbonylmethyl)oxymethyl]pyrrolidine (0.58 g) with sodium methoxide (28% solution in methanol) (0.36 ml) in substantially the same manner as that of Preparation 31-1).

IR (Neat) : 1720–1670 cm$^{-1}$

NMR (CDCl$_3$, δ) : 4.10 (2H, s)

PREPARATION 31-4

(2S,4S)-2-(1-carbamoyl-1-methylethyl)oxymethyl-4-mercapto-1-(4-nitrobenzyloxycarbonyl)pyrrolidine (0.65 g) was obtained by reacting (2S,4S)-4-acetylthio-2-(1-carbamoyl-1-methylethyl)oxymethyl-1-(4-nitrobenzyloxycarbonyl)pyrrolidine (0.83 g) in substantially the same manner as that of Preparation 31-1).

IR (Neat) : 1705–1675 cm$^{-1}$

NMR (CDCl$_3$, δ) : 1.39 (6H, s), 3.66 (2H, d, J=4.5 Hz), 3.9–4.3 (2H, m), 5.23 (2H, s), 7.52 (2H, d, J=8.5 Hz), 8.25 (2H, d, J=8.5 Hz)

PREPARATION 32

1) To a suspension of sodium hydride (62.8% suspension in oil) (0.38 g) in N,N-dimethylformamide (12 ml) was added 5-mercapto-1-methyl-1H-tetrazole (1.14 g) under ice-cooling. The mixture was stirred at the same temperature for 30 minutes. This solution was added dropwise to a solution of (2S,4R)-4-t-butyldimethylsilyloxy-2-methanesulfonyloxymethyl-1-(4nitrobenzyloxycarbonyl)pyrrolidine (3.0 g) in N,N-dimethylformamide (60 ml) under ice-cooling. The mixture was stirred at 60°–70° C. for 2 hours. The reaction mixture was poured into ice-water (200 ml) and extracted 3 times with ethyl acetate (100 ml). The extracts were combined, washed with saturated aqueous sodium chloride, dried over anhydrous magnesium sulfate and evaporated in vacuo. The resulting residue was chromatographed on silica gel (100 g) eluting with a mixture of dichloromethane and acetone (40:1, V/V). The fractions containing the desired compound were collected and concentrated under reduced pressure to give (2S,4R)-4-t-butyldimethylsilyloxy-2-(1-methyl-1H-tetrazol-5-yl)thiomethyl-1-(4-nitrobenzyloxycarbonyl)-pyrrolidine (1.68 g).

IR (Neat) : 1710–1700, 1610, 1530–1520, 1350, 1260 cm$^{-1}$

NMR (CDCl$_3$, δ) : 0.07 (6H, s), 0.86 (9H, s), 1.90–2.15 (2H, m), 3.40–3.60 (2H, m), 3.60–3.85 (2H, m), 3.83 (3H, s), 4.25–4.55 (2H, m), 5.15–5.35 (2H, m), 7.53 (2H, br. d, J=8 Hz), 8.23 (2H, d, J=8 Hz)

2) (2S,4R)-4-t-Butyldimethylsilyloxy-1-(4-nitrobenzyloxycarbonyl)-2-(1,3,4-thiadiazol-2-ylthiomethyl)-pyrrolidine (2.41 g) was obtained by reacting (2S,4R)-4-t-butyldimethylsilyloxy-2-methanesulfonyloxymethyl-1-(4-nitrobenzyloxycarbonyl)pyrrolidine (3.0 g) with 2-mercapto-1,3,4-thiadiazole (2.32 g) in substantially the same manner as that of Preparation 32-1).

IR (Neat): 1705, 1610, 1525, 1350, 1260 cm$^{-1}$

NMR (CDCl$_3$, δ): 0.06 (6H, s), 0.82 (9H, s), 1.56 (1H, s), 1.93–2.22 (2H, m), 3.43–3.63 (2H, m), 3.66–3.95 (2H, m), 4.30–4.65 (2H , m), 5.25 (2H, br. s), 7.52 (2H, br. d, J=8 Hz), 8.21 (2H, d, J=8 Hz), 8.98 (1H, s)

3) (2S,4R)-4-t-Butyldimethylsilyloxy-2-[1-{2-(N,N-dimethylamino)ethyl}-1H-tetrazol-5-yl]thiomethyl-1-(4-nitrobenzyloxycarbonyl)pyrrolidine (2.55 g) was obtained by reacting (2S,4R)-4-t-butyldimethylsilyloxy-2-methanesulfonyloxymethyl-1-(4-nitrobenzyloxycarbonyl)pyrrolidine (3.0 g) with 1-[2-(N,N-dimethylamino)ethyl]-5-mercapto-1H-tetrazole (2.28 g) in substantially the same manner as that of Preparation 32-1).

IR (Neat) : 1710, 1678, 1610, 1528, 1405, 1260 cm$^{-1}$

NMR (CDCl$_3$, δ) : 0.04 (6H, s), 0.83 (9H, s), 1.88–2.21 (2H, m), 2.25 (6H, s), 3.45–3.64 (2H, m), 3.68–3.91 (2H, m), 4.17–4.60 (4H, m), 5.21–5.36 (2H, m), 7.55 (2H, br. d, J=8 Hz), 8.62 (2H, d, J=8 Hz)

4) (2S,4R)-4-t-Butyldimethylsilyloxy-1-(4-nitrobenzyloxycarbonyl)-2-(pyridin-4-ylthiomathyl)pyrrolidine (2.59 g) was obtained by reacting (2S,4R)-4-t-butyldimethylsilyloxy-2-methanesulfonyloxymethyl-1-(4nitrobenzyloxycarbonyl)pyrrolidine (3.5 g) with 4-mercaptopyridine (1.28 ml) in substantially the same manner as that of Preparation 32-1).

IR (Neat) : 1710–1700, 1610, 1580, 1525, 1350, 1260 cm$^{-1}$

NMR (CDCl$_3$, δ) : 0.06 (9H, s), 0.86 (3H, s), 1.90–2.25 (4H, m), 2.80–3.30 (1H, m), 3.35–3.65 (3H, m), 4.10–4.65 (2H, m), 5.25 (2H, br. s), 7.20–7.75 (4H, m), 8.15–8.55 (4H, m)

PREPARATION 33

1) To a solution of (2S,4R)-4-t-butyldimethylsilyloxy-2-(1-methyl-1H-tetrazol-5-yl)thiomethyl-1-(4nitrobenzyloxycarbonyl)pyrrolidine (1.67 g) in methanol (30 ml) was added conc. hydrochloric acid (0.82 ml) at ambient temperature. After stirring at the same temperature for 1 hour, the reaction mixture was concentrated under reduced pressure. The resulting residue was dissolved in ethyl acetate (80 ml). The solution was washed with saturated aqueous sodium hydrogen carbonate and saturated aqueous sodium chloride successively, dried over anhydrous magnesium sulfate, and evaporated in vacuo to give (2S,4R)-4-hydroxy-2-(1-methyl-1H-tetrazol-5-yl)thiomethyl-1-(4-nitrobenzyloxycarbonyl)pyrrolidine (1.25 g).

IR (Neat): 1710–1680, 1610, 1525, 1350 cm$^{-1}$

NMR (CDCl$_3$, δ): 2.10–2.35 (3H, m), 3.50–3.90 (4H, m), 3.93 (3H, s), 4.30–4.70 (2H, m), 5.21 (2H, s), 7.56 (2H, d, J=8 Hz), 8.22 (2H, d, J=8 Hz)

Mass : 394 (M$^+$)

2) (2S,4R)-4-Hydroxy-1-(4-nitrobenzyloxycarbonyl)-2-(1,3,4-thiadiazol-2-ylthiomethyl)pyrrolidine (1.76 g) was obtained by reacting (2S,4R)-4-t-butyldimethylsilyloxy-1-(4-nitrobenzyloxycarbonyl-2-(1,3,4-thiadiazol-2-ylthiomethyl)pyrrolidine (2.40 g) with conc. hydrochloric acid in substantially the same manner as that of Preparation 33-1).

IR (Neat) : 1710, 1690, 1610, 1520, 1350 cm$^{-1}$

NMR (CDCl$_3$, δ) : 2.06–2.34 (3H, m), 3.50–3.90 (4H, m), 4.33–4.73 (2H, m), 5.22 (2H, s), 7.53 (2H,br.d, J=8 Hz), 8.20 (2H, d, J=8 Hz), 9.86 (1H, s)

Mass : 396 (M$^+$)

3) (2S,4R)-2-[1-{2-(N,N-Dimethylamino)ethyl}-1H-tetrazol-5-yl]thiomethyl-4-hydroxy-1-(4-nitrobenzyloxycarbonyl)pyrrolidine (1.83 g) was obtained by reacting (2S,4R)-4-t-butyldimethylsilyloxy-2-[1-{2-(N,N-dimethylamino)ethyl}-1H-tetrazol-5-yl]thiomethyl-1-(4-nitrobenzyloxycarbonyl)pyrrolidine (2.54 g) with conc. hydrochloric acid in substantially the same manner as that of Preparation 33-1).

IR (Neat) : 1705, 1610, 1525, 1405, 1350 cm$^{-1}$

NMR (CDCl$_3$, δ): 2.02–2.25 (1H, m), 2.26 (6H, s), 2.63–3.01 (2H, m), 3.53–3.95 (4H, m), 4.18–4.67 (4H, m), 5.25 (2H, s), 7.58 (2H, br.d, J=8 Hz), 8.63 (2H, d, J=8 Hz)

Mass : 451 (M$^+$)

4) (2S,4R)-4-Hydroxy-1-(4-nitrobenzyloxycarbonyl)-(pyridin-4-ylthiomethyl)pyrrolidine (1.98 g) was obtained by reacting (2S,4R)-4-t-butyldimethylsilyloxy-(4-nitrobenzyloxycarbonyl)-2-(pyridin-4-ylthiomethyl)-pyrrolidine (2.57 g) with conc. hydrochloric acid (1.25 ml) in substantially the same manner as that of Preparation 33-1) .

IR (Neat) : 1700–1685, 1610, 1590, 1525, 1350 cm$^{-1}$

NMR (CDCl$_3$, δ) : 2.70–3.20 (3H, m), 3.35–3.85 (3H, m), 4.15–4.60 (2H, m), 5.21 (2H, s), 7.15–7.40 (2H, m), 7.48 (2H, d, J=8 Hz), 8.18 (2H, d, J=8 Hz), 8.20–8.45 (2H, m),

Mass : 389 (M$^+$), 265 (M$^+$−124)

PREPARATION 34

1) To a solution of (2S,4R)-4-hydroxy-2-(1-methyl-1H-tetrazol-5-yl)thiomethyl-1-(4-nitrobenzyloxycarbonyl)pyrrolidine (1.23 g) and triphenylphosphine (1.23 g) in tetrahydrofuran (25 ml) was added dropwise a solution of diethyl azodicarboxylate (0.74 ml) in tetrahydrofuran (2 ml) under ice-cooling. After stirring at the same temperature for 30 minutes, to the solution was added thiobenzoic S-acid (0.55 ml) under ice-cooling. The mixture was stirred at the same temperature for 2 hours. The reaction mixture was concentrated under reduced pressure to give a residue. The residue was dissolved in ethyl acetate (100 ml) and the solution was washed with saturated aqueous sodium hydrogen carbonate and saturated aqueous sodium chloride successively, dried over anhydrous magnesium sulfate, and evaporated in vacuo. The resulting residue was chromatographed on silica gel (100 g) eluting with a mixture of dichloromethane and acetone (19:1, V/V). The fractions containing the resired compound were collected and evaporated in vacuo to give (2S,4S)-4-benzoylthio-2-(1-methyl-1H-tetrazol-5-yl)thiomethyl-1(4-nitrobenzyloxycarbonyl)pyrrolidine (1.61 g).

IR (Neat) : 1710–1700, 1665, 1610, 1525, 1350, 1210 cm$^{-1}$

NMR (CDCl$_3$, δ) : 3.92 (3H, s), 5.92 (2H, s), 7.41–7.75 (5H, ml), 7.83–8.08 (2H, m), 8.25 (2H, d, J=8 Hz)

2) (2S,4S)-4-Benzoylthio-1-(4-nitrobenzyloxycarbonyl)-2-(1,3,4-thiadiazol-2-ylthiomethyl)pyrrolidine (2.73 g) was obtained by reacting (2S,4R)-4-hydroxy-1-(4-nitrobenzyloxycarbonyl)-2-(1,3,4-thiadiazol-2-ylthiomethyl)pyrrolidine (1.77 g) with triphenylphosphine (1.76 g), diethyl azodicarboxylate (1.05 ml) and thiobenzoic S-acid (0.79 ml) successively in substantially the same manner as that of Preparation 34-1).

IR (Neat) : 1710–1660, 1610, 1530–1520, 1350 cm$^{-1}$

NMR (CDCl$_3$, δ) : 3.80–4.06 (2H, m), 5.27 (2H, s), 7.37–7.73 (5H, m), 7.82–8.05 (2H, m), 8.24 (2H, d, J=8 Hz), 9.01 (1H, s)

3) (2S,4S)-4-Benzoylthio-2-[1-{2-(N,N-dimethylamino)ethyl}-1H-tetrazol-5-yl]thiomethyl-1-(4-nitrobenzyloxycarbonyl)pyrrolidine (2.68 g) was obtained by reacting (2S,4R)-2-[1-{2-(N,N-dimethylamino)ethyl}-1H-tetrazol-5-yl]thiomethyl-4-hydroxy-1-(4-nitrobenzyloxycarbonyl)pyrrolidine (1.82 g) with triphenylphosphine (1.59 g), diethyl azodicarboxylate (0.95 ml), and thiobenzoic S-acid (0.98 ml) successively in substantially the same manner as that of Preparation 34-1).

IR (Neat) : 1710, 1670–1660, 1610, 1525, 1405, 1350 cm$^{-1}$

NMR (CDCl$_3$, δ) : 2.22 (3H, s), 2.66–2.96 (2H, m), 4.15–4.50 (4H, m), 5.26 (2H, s), 8.25 (2H, d, J=8 Hz)

4) (2S,4S)-4-Benzoylthio-1-(4-nitrobenzyloxycarbonyl)-2-(pyridin-4-ylthiomethyl)pyrrolidine (3.56 g) was obtained by reacting (2S,4R)-4-hydroxy-1-(4-nitrobenzyloxycarbonyl)-2-(pyridine-4-ylthiomethyl)-pyrrolidine (1.97 g) with triphenylphosphine (1.99 g), diethyl azodicarboxylate (1.19 ml) and thiobenzoic S-acid (0.89 ml) successively in substantially the same manner as that of Preparation 34-1).

IR (Nujol) : 1710, 1670, 1585, 1525, 1350 cm$^{-1}$

NMR (CDCl$_3$, δ): 2.40–2.70 (2H, m), 4.10–4.45 (2H, m), 5.25 (2H, s), 8.15–8.60 (4H, m)

PREPARATION 35

1) To a solution of (2S,4S)-4-benzoylthio-2-(1-methyl-1H-tetrazol-5-yl)thiomethyl-1-(4-nitrobenzyloxycarbonyl)pyrrolidine (1.60 g) in methanol (30 ml) was added sodium methoxide (28% solution in methanol) (0.78 ml) under ice-cooling. After stirring at the same temperature for 30 minutes, to this solution was added glacial acetic acid (1 ml). The mixture was concentrated under reduced pressure to give a residue. The residue was dissolved in ethyl acetate (100 ml). The solution was washed with saturated aqueous sodium chloride, dried over anhydrous magnesium sulfate and evaporated in vacuo. The resulting residue was chromatographed on silica gel (100 g) eluting with a mixture of dichloromethane and acetone (20:1, V/V). The fractions containing the desired compound were collected and evaporated in vacuo to give (2S,4S)-4-mercapto-2-(1-methyl-1H-tetrazol-5-yl)thiomethyl-1-(4-nitrobenzyloxycarbonyl)pyrrolidine (0.78 g).

mp: 144°–145° C.

IR (Neat): 1710–1690, 1610, 1520, 1350 cm$^{-1}$

NMR (CDCl$_3$, δ): 1.63–1.93 (2H, m), 1.98–2.25 (1H, m), 2.52–3.03 (1H, m), 3.12–3.53 (2H, m), 3.65–3.95 (1H, m), 3.92 (3H, s), 4.02–4.54 (2H, m), 5.22 (2H, s), 7.56 (2H, br.d, J=8 Hz), 8.21 (2H, d, J=8 Hz)

Mass: 410 (M$^+$), 377 (M$^+$−33)

2) (2S,4S)-4-Mercapto-1-(4-nitrobenzyloxycarbonyl-2-(1,3,4-thiadiazol-2-ylthiomethyl)pyrrolidine (1.74 g) was obtained by reacting (2S,4S)-4-benzoylthio-1-(4-nitrobenzyloxycarbonyl-2-(1,3,4-thiadiazol-2-ylthiomethyl)pyrrolidine (2.71 g) with sodium methoxide in substantially the same manner as that of Preparation 35-1).

mp: 81°–82° C.

IR (Nujol): 1700, 1605, 1535 (sh), 1520, 1405, 1340 cm$^{-1}$

NMR (CDCl$_3$, δ): 1.71–1.90 (1H, m), 1.90–2.23 (2H, m), 2.43–2.96 (1H, m), 3.03–3.60 (2H, m), 3.70–4.03 (2H, m), 5.25 (2H, s), 7.60 (2H, br. d, J=8 Hz), 8.23 (2H, d, J=8 Hz), 9.03 (1H, s)

Mass : 379 (M$^+$ −34)

3) (2S,4S)-2-[1-{2-(N,N-Dimethylamino)ethyl}-1H-tetrazol-5-yl]thiomethyl-4-mercapto-1-(4-nitrobenzyloxycarbonyl)pyrrolidine (1.13 g) was obtained by reacting (2S,4S)-4-benzoylthio-2-[1-{2-(N,N-dimethylamino)ethyl}-1H-tetrazol-5-yl]thiomethyl-1-(4-nitrobenzyloxycarbonyl)pyrrolidine (2.66 g) with sodium methoxide in substantially the same manner as that of Preparation 35-1).

IR (Neat): 1710–1700, 1610, 1525, 1405, 1350 cm$^{-1}$

NMR (CDCl$_3$, δ): 2.28 (6H, s), 5.25 (2H, s), 8.24 (2H, d, J=8 Hz)

Mass: 467 (M$^+$ −1)

4) (2S,4S)-4-Mercapto-1-(4-nitrobenzyloxycarbonyl)-2-(pyridin-4-ylthiomethyl)pyrrolidine (2.40 g) was obtained by reacting (2S,4S)-4-benzoylthio-1-(4-nitrobenzyloxycarbonyl)-2-(pyridin-4-ylthiomethyl)pyrrolidine (3.54 g) with sodium methoxide in substantially the same manner as that of Preparation 35-1)

IR (Nujol): 1690, 1580, 1525, 1350 cm$^{-1}$

NMR (CDCl$_3$, δ) : 1.65–2.20 (2H, m), 2.40–2.90 (1H, m), 3.05–3.50 (2H, m), 3.50–3.65 (1H, m), 3.80–4.40 (3H, m), 5.25 (2H, s), 8.20 (2H, d, J=8 Hz), 8.36 (2H, br. d, J=6 Hz)

Mass: 405 (M$^+$), 281 (M$^+$ −124)

PREPARATION 36

To a solution of (2S,4R)-2-(carboxymethyloxymethyl)-4-methanesulfonyloxy-1-(4-nitrobenzyloxycarbonyl)pyrrolidine (2.4 g) in tetrahydrofuran (50 ml) was added triethyamine (1.6 ml). Isobutyl chloroformate (1.1 ml) was dropwise added to the mixture at −5° to −10° C. under nitrogen, followed by stirring for 30 minutes at the same temperature The insoluble material was filtered off and the filtrate was added to a solution of sodium borohydride (0.70 g) in water (20 ml) at 0° C. After stirring for 2 hours at the same temperature, acetic acid (3 ml) was added thereto The reaction mixture was evaporated, diluted with ethyl acetate and washed successively with water, saturated sodium bicarbonate and brine The dried organic layer was concentrated under reduced pressure, and the obtained syrup was subjected to a column chromatography on silica gel and eluted with a mixture of dichloromethane and acetone (4:1 v/v) to give (2S,4R)-2-(2-hydroxyethyloxymethyl)-4-methane- sulfonyloxy-1-(4-nitrobenzyloxycarbonyl)pyrrolidine (2.1 g).

IR (CH$_2$Cl$_2$): 3460, 1680–1720, 1605 cm$^{-1}$

NMR (CDCl$_3$, δ): 2.1–2.5 (2H, m), 3.02 (3H, s), 3.4–4.0 (8H, m), 4.1–4.4 (1H, m), 5.2–5.5 (3H, m), 7.53 (2H, d, J=8.5Hz), 8.27 (2H, d, J=8.5Hz)

PREPARATION 37

(2S,4S)-4-Acetylthio-2-(2-hydroxyethyloxymethyl)-1-(4-nitrobenzyloxycarbonyl)pyrrolidine (1.8 g) was obtained by reacting (2S,4R)-2-(2-hydroxyethyloxymethyl)-4-methane-sulfonyloxy-1-(4-nitrobenzyloxycarbonyl)pyrrolidine (2.1 g) with thioacetic S-acid (0.54 ml) and sodium hydride (62.8% suspension in oil, 0.29 g) in substantially the same manner as that of Preparation 30-1).

IR (Neat): 3350–3450, 1670–1720, 1605 cm$^{-1}$

NMR (CDCl$_3$, δ): 1.8–2.7 (2H, m), 2.33 (3H, s), 3.28 (1H, m), 3.5–4.4 (9H, m), 5.27 (2H, s), 7.54 (2H, d, J=9Hz), 8.29 (2H, d, J=9Hz)

PREPARATION 38

To a solution of (2S,4S)-4-acetylthio-2-(2-hydroxyethyloxymethyl)-1-(4-nitrobenzyloxycarbonyl)pyrrolidine (1.1 g) in acetonitrile (20 ml) was added chlorosulfonyl isocyanate(0.32 ml) at 0°–5° C. and the mixture was stirred at 20°–25° C. for 1 hour. Water (3 ml) was added to the solution at the same temperature and the mixture was stirred for 20 hours. After the solvent was evaporated, the residue was dissolved in ethyl acetate, washed with water, saturated sodium bicarbonate and brine successively. The dried organic layer was evaporated to give (2S,4S)-4-acetylthio-2-(2-carbamoyloxyethyloxymethyl)-1-(4-nitrobenzyloxycarbonyl)pyrrolidine (1.19 g).

IR (Neat): 3450, 3350, 1680–1730, 1605 cm$^{-1}$

NMR (CDCl$_3$, δ): 2.32 (3H, s), 2.2–2.8 (2H, m), 3.0–3.4 (1H, m), 3.5–3.8 (4H, m), 3.8–4.3 (5H, m), 4.5–5.0 (2H, m), 5.22 (2H, s), 7.56 (2H, d, J=9Hz) 8.29 (2H, d, J=9Hz)

PREPARATION 39-1

(2S,4S)-2-(2-Hydroxyethyloxymethyl)-4-mercapto-1-(4-nitrobenzyloxycarbonyl)pyrrolidine (520 mg) was obtained by reacting (2S,4S)-4-acetylthio-2-(2-hydroxyethyloxymethyl)-1-(4-nitrobenzyloxycarbonyl)pyrrolidine (640 mg) with a 28% solution of sodium methoxide in methanol (0.5 ml) in substantially the same manner as that of Preparation 31-1).

IR (Neat): 3400, 1685–1710, 1605 cm$^{-1}$

NMR (CDCl$_3$, δ): 3.1–3.4 (1H, m), 3.4–3.8 (6H, m), 3.9–4.3 (3H, m), 5.21 (1H, m), 7.52 (2H, d, J=9Hz) 8.29 (2H, d, J=9Hz)

PREPARATION 39-2

(2S,4S)-2-(2-Carbamoyloxyethyloxymethyl)-4-mercapto-1-(4-nitrobenzyloxycarbonyl)pyrrolidine (910 mg) was obtained by reacting (2S,4S)-4-acetylthio-2-(2-carbamoyloxyethyloxymethyl)-1-(4-nitrobenzyloxycarbonyl)pyrrolidine (1.19 g) with a 28% solution of sodium methoxide in methanol (0.83 ml) in substantially the same manner as that of Preparation 31-1).

IR (Neat): 3300–3400, 1670–1720, 1600 cm$^{-1}$

NMR (CDCl$_3$, δ): 3.0–3.4 (2H, m), 3.5–3.8 (4H, m), 3.9–4.3 (4H, m), 5.22 (2H, s), 7.53 (2H, d, J=9Hz), 8.29 (2H, d, J=9Hz)

PREPARATION 40

To a solution of (2S,4R)-2-acetylthiomethyl-4-t-butyl-dimethylsilyloxy-1-(4-nitrobenzyloxycarbonyl)-pyrrolidine (1 g) in methanol (10 ml) was added 28% sodium methoxidemethanol solution (0.45 ml) with stirring under ice-cooling and the mixture was stirred at the same temperature for 10 minutes. To the reaction mixture was dropwise added epichlorohydrin (0.22 ml) and then the mixture was stirred at ambient temperature for 2 hours. The reaction mixture was evaporated in vacuo. The resulting residue was dissolved in ethyl acetate (40 ml) and the solution was washed with saturated aqueous sodium chloride, dried over anhydrous magnesium sulfate and concentrated under reduced pressure. The resulting residue was subjected to a column chromatography on silica gel (50 g) eluting with a mixture of n-hexane and ethyl acetate (2:1 v/v). The fractions containing the desired compound were collected and evaporated in vacuo to give (2S,4R)-4-t-butyldimethylsilyloxy-2-[(2,3-epoxypropyl)thiomethyl]-1-(4-nitrobenzyloxycarbonyl}pyrrolidine (0.61 g).

IR (Neat): 1710, 1610, 1525, 1350, 1260 cm$^{-1}$

NMR (CDCl$_3$, δ): 0.06 (6H, s), 0.86 (9H, s), 1.90–2.20 (2H, m), 2.45–3.30 (7H, m), 3.45–3.65 (2H, m), 4.10–4.60 (2H, m), 5.27 (2H, s), 7.55 (2H, d, J=9 Hz), 8.37 (2H, d, J=9 Hz)

PREPARATION 41

A solution of (2S,4R)-4-t-butyldimethylsilyloxy-2-[(2,3-epoxypropyl)thiomethyl]-1-(4-nitrobenzyloxycarbonyl)pyrrolidine (2.59 g), sodium azide (0.52 g) and ammonium chloride (0.43 g) in N,N-dimethylformamide (26 ml) was stirred at 80°–90° C. for 2 hours. The reaction mixture was poured into ice-water (100 ml) and extracted 3 times with ethyl acetate (40 ml). The extract was washed with saturated aqueous sodium chloride, dried over anhydrous magnesium sulfate and evaporated in vacuo. The resulting residue was chromatographed on silica gel (100 g) eluting with a mixture of n-hexane and ethyl acetate (3:1 v/v). The fractions containing the desired compound were collected and evaporated in vacuo to give (2S,4R)-2-[(3-azido-2-hydroxypropyl)thiomethyl]-4-t-butyldimethylsilyloxy-1-(4-nitrobenzyloxycarbonyl)pyrrolidine (1.95 g).

IR (Neat) : 2110, 1740, 1710–1700, 1680–1665, 1610, 1525, 1350, 1255 cm$^{-1}$

PREPARATION 42

To a solution of (2S,4R)-2-[(3-azido-2-hydroxypropyl)thiomethyl]-4-t-butyldimethylsilyloxy-1-(4-nitrobenzyloxycarbonyl)pyrrolidine (1.94 g) in pyridine (6 ml) was added triphenylphosphine (1.55 g) and the mixture was stirred at ambient temperature for 1 hour. To the reaction mixture was added conc. ammonia (0.50 ml) and the mixture was allowed to stand overnight at ambient temperature. The reaction mixture was concentrated under reduced pressure. The resulting mixture was dissolved in ethyl acetate (40 ml) and the solution was washed with saturated aqueous sodium chloride, dried over magnesium sulfate and evaporated in vacuo to give (2S,4R)-2-[(3-amino-2-hydroxypropyl)thiomethyl]-4-t-butyldimethylsilyloxy-1-(4-nitrobenzyloxycarbonyl)pyrroliidine. The residue containing the compound obtained above was dissolved in a mixture of ethyl acetate and water (3:1 V/V, 40 ml). To the solution was dropwise added a solution of 4-nitrobenzyloxycarbonyl chloride (0.87 g) in tetrahydrofuran (3 ml) with stirring at 2°–5° C., keeping the pH between 9–10 with 1N sodium hydroxide. The mixture was stirred at the same temperature for 1 hour. The organic layer was separated, washed with saturated aqueous sodium chloride, dried over magnesium sulfate and evaporated in vacuo. The resulting residue was chromatographed on silica gel (100 g) eluting with a mixture of dichloromethane and acetone (9:1 v/v). The fractions containing the desired compound were collected and evaporated in vacuo to give (2S,4R)-2-{3-(4-nitrobenzyloxycarbonyl)amino-2hydroxypropyl}thiomethyl-4-t-butyldimethylsilyloxy-1-(4-nitrobenzyloxycarbonyl)-pyrrolidine (2.25 g).

IR (Neat): 1710–1700, 1610, 1525, 1350, 1260 cm$^{-1}$

NMR (CDCl$_3$, δ): 0.06 (6H, s), 0.86 (9H, s), 1.90–2.20 (2H, m), 5.15–5.30 (4H, m), 7.52 (4H, d, J=8 Hz), 8.25 (4H, d, J=8 Hz)

PREPARATION 43

To a solution of (2S,4R)-2-[3-(4-nitrobenzyloxycarbonyl)amino-2-hydroxypropyl]thiomethyl-4-t-butyldimethylsilyloxy-1-(4-nitrobenzyloxycarbonyl)pyrrolidine (2.24 g) in dichloromethane (40 ml) were added pyridine (0.52 ml) and acetyl chloride (0.46 ml) under ice-cooling with stirring. The mixture was stirred at the same temperature for 1 hour. The reaction mixture was washed with water, saturated aqueous sodium hydrogen carbonate and saturated aqueous sodium chloride, in turn, dried over anhydrous magnesium sulfate, and evaporated in vacuo to give (2S,4R)-2-[2-acetoxy-3-(4-nitrobenzyloxycarbonyl)aminopropyl]thiomethyl-4-t-butyldimethylsilyloxy-1-(4-nitrobenzyloxycarbonyl)-pyrrolidine (2.37 g).

NMR (CDCl$_3$, δ): 0.06 (6H, s), 0.83 (9H, s), 2.06 (3H, d, J=3 Hz), 5.15–5.30 (4H, m), 8.22 (4H, d, J=8 Hz)

PREPARATION 44

(2S,4R)-2-[2-Acetoxy-3-(4-nitrobenzyloxycarbonyl)aminopropyl]thiomethyl-4-hydroxy-1-(4-nitrobenzyloxycarbonyl)pyrrolidine (1.94 g) was obtained by reacting (2S,4R)-2-[2-acetoxy-3-(4-nitrobenzyloxycarbonyl)aminopropyl]thiomethyl-4-t-butyldimethylsilyloxy-1-(4-nitrobenzyloxycarbonyl)pyrrolidine (2.36 g) with conc. hydrochloric acid (0.54 ml) in substantially the same manner as that of Preparation 9.

NMR (CDCl$_3$, δ): 2.06 (3H, s), 5.15–5.35 (4H, m), 7.40–7.60 (4H, m), 8.21 (4H, d, J=8 Hz)

PREPARATION 45

(2S,4S)-2-[2-Acetoxy-3-(4-nitrobenzyloxycarbonyl)aminopropyl]thiomethyl-4-benzoylthio-1-(4-nitrobenzyloxycarbonyl)pyrrolidine (1.51 g) was obtained by reacting (2S,4R)-2-[2-acetoxy-3-(4-nitrobenzyloxycarbonyl)aminopropyl]thiomethyl-4-hydroxy-1-(4-nitrobenzyloxycarbonyl)pyrrolidine (1.94 g) with triphenylphosphine (1.10 g), and diethyl azodicarboxylate (0.66 ml) successively, and then with thiobenzoic S-acid (0.50 ml) in substantially the same manner as that of Preparation 4.

NMR (CDCl$_3$, δ): 2.06 (3H, s), 4.90–5.20 (2H, m), 5.20–5.40 (4H, m), 7.40–7.70 (7H, m), 7.97 (2H, dd, J=7 Hz, J=2 Hz), 8.26 (4H, d, J=8 Hz)

PREPARATION 46

(2S,4S)-2-[2-Hydroxy-3-(4-nitrobenzyloxycarbonyl)aminopropyl]thiomethyl-4-mercapto-1-(4-nitrobenzyloxycarbonyl)pyrrolidine (0.49 g) was obtained by reacting (2S,4S)-2-[2-acetoxy-3-(4-nitrobenzyloxycarbonyl)aminopropyl]thiomethyl-4-benzoylthio-1-(4-nitrobenzyloxycarbonyl)pyrrolidine (1.50 g) with 28% sodium methoxide-methanol solution (0.81 ml) in substantially the same manner as that of Preparation 7-1).

NMR (CDCl$_3$, δ): 1.50–2.05 (3H, m), 2.40–3.60 (9H, m), 3.70–4.25 (3H, m), 5.22 (4H, s), 5.25–5.45 (1H, m) 7.53 (4H, d, J=8 Hz), 8.25 (4H, d, J=8 Hz)

PREPARATION 47

To a solution of (2S,4R)-2-aminomethyl-4-t-butyldimethylsilyloxy-1-(4-nitrobenzyloxycarbonyl)pyrrolidine (2 g) were successively added triethylamine (0.82 ml) and methanesulfonyl chloride (0.42 ml) under ice-cooling with stirring, and the mixture was stirred at the same temperature for 1 hour. The reaction mixture was washed with saturated aqueous sodium chloride, dried over anhydrous magnesium sulfate and evaporated in vacuo to give (2S,4R)-2-methanesulfonylaminomethyl-4-t-butyldimethylsilyloxy-1-(4nitrobenzyloxycarbonyl)-pyrrolidine (2.15 g).

IR (Neat): 1705, 1690, 1610, 1530, 1350 cm$^{-1}$

NMR (CDCl$_3$, δ): 0.08 (6H, s), 0.86 (9H, s), 1.80–2.20 (2H, m), 2.94 (3H, s), 4.00–4.55 (2H, m), 5.23–5.46 (2H, m), 7.55 (2H, m), 8.26 (1H, d, J=9 Hz)

PREPARATION 48

(2S,4R)-4-Hydroxy-2-methanesulfonylaminomethyl-1-(4-nitrobenzyloxycarbonyl)pyrrolidine (1.57 g) was obtained by reacting (2S,4R)-4-t-butyldimethylsilyloxy-2-methanesulfonylaminomethyl-1-(4-nitrobenzyloxycarbonyl)pyrrolidine (2.14 g) with conc. hydrochloric acid (0.73 ml) in substantially the same manner as that of Preparation 9.

IR (Neat): 1760–1750, 1710–1690, 1640, 1605, 1515 cm$^{-1}$

PREPARATION 49

(2S,4R)-2-Methanesulfonylaminomethyl-4-methanesulfonyloxy-1-(4-nitrobenzyloxycarbonyl)pyrrolidine (1.63 g) was obtained by reacting (2S,4R)-4-hydroxy-2-methanesulfonylaminomethyl-1-(4-nitrobenzyloxycarbonyl)pyrrolidine (1.62 g) with methanesulfonyl chloride (0.37 ml) in substantially the same manner as that of Preparation 25-1).

NMR (CDCl$_3$, δ): 2.00–2.70 (2H, m), 2.92 (3H, s), 3.03 (3H, s), 5.25 (2H, s), 7.55 (2H, d, J=8 Hz), 8.25 (2H, d, J=8 Hz)

EI MS: 277 (M$^+$ −174)

PREPARATION 50

To a suspension of sodium borohydride (0.5 g) in tetrahydrofuran (30 ml) was dropwise added boron trifluoride etherate (5.8 ml) under ice-cooling. After 30 minutes, a solution of (2S,4R)-2-(carbamoylmethyloxymethyl)-4-methanesulfonyloxy-1-(4-nitrobenzyloxycarbonyl)pyrrol:ine (2.40 g) in tetrahydrofuran (10 ml) was added to the mixture under ice-cooling, and the mixture was stirred under the same condition for 2 hours and at ambient temperature for 18 hours. The mixture was concentrated under reduced pressure to give a residue. The residue was stirred in a mixture of concentrated hydrochloric acid (4 ml) and methanol (40 ml) at ambient temperature for 16 hours, and evaporated under reduced pressure to give a syrup. To a solution of the syrup in tetrahydrofuran (30 ml) were added triethylamine (1.2 ml) and methanesulfonyl chloride (0.5 ml) in turn under ice-cooling. After stirring for 1 hour, the reaction mixture was poured into a mixture of ethyl acetate (150 ml) and water (100 ml). The organic layer was dried over magnesium sulfate and concentrated under reduced pressure to give a syrup. The syrup was subjected to a column chromatography on silica gel (30 g) and eluted with a mixture of methanol and chloroform (3:97 V/V) to give (2S,4R)-2-[2-(methanesulfonylamino)ethyloxymethyl]-4-methanesulfonyloxy-1-(4-nitrobenzyloxycarbonyl)pyrrolidine (1.30 g).

IR (Neat): 1705–1685, 1605 cm$^{-1}$

NMR (CDCl$_3$, δ) : 2.96 (3H, s), 3.03 (3H, s), 5.23 (2H, s), 7.48 (2H, d, J=8.5 Hz), 8.18 (2H, d, J=8.5 Hz).

PREPARATION 51-1

(2S,4S)-4-Acetylthio-2-methanesulfonylaminomethyl-1-(4-nitrobenzyloxycarbonyl)pyrrolidine (1.16 g) was obtained by reacting (2S,4R)-2-methanesulfonylaminomethyl-4-methanesulfonyloxy-1-(4-nitrobenzyloxycarbonyl)pyrrolidine (1.61 g) with potassium thioacetate (0.81 g) in substantially the same manner as that of Preparation 30-1).

NMR (CDCl$_3$, δ): 1.50–2.20 (2H,m), 2.33 (3H, s), 2.92 (3H, s), 3.10–3.60 (3H, m), 3.70–4.25 (3H, m), 5.23 (2H, s), 7.55 (2H, d, J=9 Hz) 8.22 (2H, d, J=9 Hz)

PREPARATION 51-2

(2S,4S)-4-Acetylthio-2-[2-(methanesulfonylamino)ethyloxymethyl]-1-(4-nitrobenzyloxycarbonyl)pyrrolidine (0.80 g) was obtained by reacting (2S,4R)-2-[2-(methanesulfonylamino)ethyloxymethyl]-4-methanesulfonyloxy-1-(4-nitrobenzyloxycarbonyl)pyrrolidine (1.28 g) with thioacetic S-acid in substantially the same manner as that of Preparation 30-1).

IR (Neat) : 1705–1685, 1605 cm$^{-1}$

NMR (CDCl$_3$, δ): 2.33 (3H, s), 2.96 (3H, s), 5.20 (2H, s), 7.48 (2H, d, J=8.5 Hz), 8.18 (2H, d, J=8.5 Hz)

PREPARATION 52-1

(2S,4S)-4-Mercapto-2-methanesulfonylaminomethyl-1-(4-nitrobenzyloxycarbonyl)pyrrolidine (0.72 g) was obtained by reacting (2S,4S)-4-acetylthio-2-methanesulfonylaminomethyl-1-(4-nitrobenzyloxycarbonyl)pyrrolidine (1.15 g) with 28% sodium methoxide-methanol solution (0.61 ml) in substantially the same manner as that of Preparation 31-1).

NMR (CDCl$_3$, δ): 1.50–2.05 (2H, m), 2.40–2.80 (1H, m), 2.95 (3H, s), 3.00–3.75 (4H, m), 3.80–4.25 (2H, m) 5.25 (2H, s), 7.56 (2H, d, J=9 Hz), 8.30 (2H, d, J=9 Hz)

PREPARATION 52-2

(2S,4S)-4-Mercapto-2-[2-(methanesulfonylamino)ethyloxymethyl]-1-(4-nitrobenzyloxycarbonyl)pyrrolidine (0.53 g) was obtained by reacting (2S,4S)-4-acetylthio-2-[2-(methanesulfonylamino)ethyloxymethyl]-1-(4-nitrobenzyloxycarbonyl)pyrrolidine (0.79 g) with 28% sodium methoxide-methanol solution in substantially the same manner as that of Preparation 31-1).

IR (Neat) : 1705–1685, 1605 cm$^{-1}$

NMR (CDCl$_3$, δ): 2.96 (3H, s), 5.21 (2H, s), 7.48 (2H, d, J=8.5 Hz), 8.20 (2H, d, J=8.5 Hz)

PREPARATION 53

To a mixture of dimethylformamide (1.50 ml) and tetrahydrofuran (10 ml) was dropwise added phosphorus oxychloride (1.50 ml) at −5°~5° C. and the mixture was stirred at the same temperature for 30 minutes. To the mixture was added a solution of (2S,4R)-2-carboxymethyloxymethyl-4-hydroxy-1-(4-nitrobenzyloxycarbonyl)pyrrolidine (2.30 g) in tetrahydrofuran (20 ml) at −5°~5° C., followed by stirring at the same temperature for 30 minutes. The mixture was dropwise added to concentrated ammonia water (30 ml) at 0°–10° C. with stirring. The mixture was stirred at the same condition for 2 hours. Tetrahydrofuran was evaporated under reduced pressure to give a mixture. The mixture was extracted with ethyl acetate (50 ml×3). The ethyl acetate layer was dried over magnesium sulfate and concentrated under reduced pressure to give a syrup. The syrup was subjected to a column chromatography on silica gel (20 g) and eluted with a mixture of methanol and chloroform (3:97 V/V) to give (2S,4R)-2-(carbamoylmethyloxymethyl)-4-hydroxy-1-(4-nitrobenzyloxycarbonyl)pyrrolidine (1.43 g).

mp: 131°-133° C.

IR (Nujol): 1705-1685 cm$^{-1}$

NMR (DMSO-d$_6$, δ): 1.8-2.1 (2H, m), 3.27 (2H, s), 3.2 3.45 (2H, m), 3.45-3.65 (2H, m), 3.77 (2H, s), 3.85-4.35 (2H, m), 4.90 (2H, d, J=3 Hz), 5.19 (2H, s), 7.08 (2H, br d, J=15 Hz), 7.57 (2H, d, J=8.5 Hz), 8.18 (2H, d, J=8.5Hz)

EI MS: 295 (M$^+$ −58), 278 (M$^+$ −75), 265 (M$^+$ −88)

PREPARATION 54

To a suspension of sodium borohydride (0.30 g) in tetrahydrofuran (15 ml) was added boron trifluoride etherate (3.5 ml) in a nitrogen stream with stirring at 0°-10° C. The mixture was stirred at the same temperature for 30 minutes. To the mixture was added a solution of (2S,4R)-2-(carbamoylmethyloxymethyl)-4-hydroxy-1-(4-nitrobenzyloxycarbonyl)pyrrolidine (1.40 g) in tetrahydrofuran (3 ml) at 0°-10° C. The mixture was stirred at 0°-10° C. for 3 hours and at ambient temperature overnight. Methanol (10 ml) was added to the reaction mixture at 0°-10° C. After 2 hours, insoluble material was filtered off and the filtrate was concentrated under reduced pressure to give a residue. A solution of the residue in a mixture of concentrated hydrochloric acid (3 ml) and methanol (30 ml) was stirred at ambient temperature for 20 hours. The mixture was concentrated under reduced pressure to give a syrup. A solution of the syrup in ethyl acetate (30 ml) was extracted with 1N hydrochloric acid (30 ml×3). The aqueous solution was adjusted to pH 10 with aqueous sodium hydroxide and extracted with chloroform (30 ml×3). The organic solution was dried over magnesium sulfate and concentrated under reduced pressure to give a syrup. The syrup was subjected to a column chromatography on silica gel (20 g) and eluted with a mixture of methanol and chloroform (5:95 and then 10:90 V/V) to give (2S,4R)-2-(2-aminoethyloxymethyl)-4-hydroxy-1-(4-nitrobenzyloxycarbonyl)pyrrolidine (1.13 g).

IR (Neat): 3500-3050, 1705 cm

NMR (CDCl$_3$, 6): 5.21 (2H, s), 7.48 (2H, d, J=8.5 Hz), 8.18 (2H, d, J=8.5 Hz)

PREPARATION 55

To a solution of (2S,4R)-2-(2-aminoethyloxymethyl)-4-hydroxy-1-(4-nitrobenzyloxycarbonyl)pyrrolidine (1.12 g) in a mixture of water (20 ml) and tetrahydrofuran (40 ml) was added a solution of 4-nitrobenzyloxycarbonyl chloride (0.85 g) in tetrahydrofuran (4 ml) under ice-cooling with stirring, keeping the pH between 8.5-9.5 with 4N aqueous sodium hydroxide. The mixture was stirred at the same condition for 2 hours. The reaction mixture was evaporated under reduced pressure and then ethyl acetate (50 ml) was added thereto. The organic layer was dried over magnesium sulfate and concentrated under reduced pressure to give a syrup. The syrup was subjected to a column chromatography on silica gel (20 g) and eluted with a mixture of methanol and chloroform (2:98 V/V) to give (2S,4R)-4-hydroxy-1-(4-nitrobenzyloxycarbonyl)-2-[2-(4nitrobenzyloxycarbonylamino)ethyloxymethyl]pyrrolidine (0.88 g).

IR (Nujol): 1710-1685 cm$^{-1}$

PREPARATION 56

To a solution of (2S,4R)-4-hydroxy-1-(4-nitrobenzyloxycarbonyl)-2-[2-(4-nitrobenzyloxycarbonylamino)ethyloxymethyl]pyrrolidine (0.87 g) and triethylamine (0.35 ml) in a mixture of tetrahydrofuran (5 ml) and dichloromethane (10 ml) was dropwise added a solution of methanesulfonyl chloride (0.16 ml) in dichloromethane (2 ml) with stirring at 0°-5° C. and the mixture was stirred at 0°-5° C. for 30 minutes. The reaction mixture was washed with water (20 ml), dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-4-methanesulfonyloxy-1-(4-nitrobenzyloxycarbonyl)2-[2-(4-nitrobenzyloxycarbonylamino)ethyloxymethyl]pyrrolidine (0.92 g).

IR (Neat): 1725-1700 cm$^{-1}$

NMR (CDCl$_3$, 6): 2.2-2.6 (2H, m), 3.02 (3H, s), 3.2-4.3 (9H, m), 4.9-5.4 (6H, m), 7.45 (4H, d, J=8.5 Hz), 8.16 (4H, d, J=8.5 Hz)

PREPARATION 57-1

(2S,4R)-4-Methanesulfonyloxy-1-(4-nitrobenzyloxycarbonyl)-2-[2-(4-nitrobenzyloxycarbonylamino)ethyloxymethyl]pyrrolidine (1.80 g) was obtained by reacting (2S,4R)-2-(carbamoylmethyloxymethyl)-4-methanesulfonyloxy-1-(4-nitrobenzyloxycarbonyl)pyrrolidine (3.60 g) with a mixture of sodium borohydride (0.75 g) and boron trifluoride etherate (8.7 ml), concentrated hydrochloric acid (6 ml), and 4-nitrobenzyloxycarbonyl chloride (2.1 g) successively in substantially the same manners as that of Preparation 10.

IR (Neat): 1725-1700 cm$^{-1}$

NMR (CDCl$_3$, δ): 2.2-2.6 (2H, m), 3.02 (3H, s), 3.2-4.3 (9H, m), 4.9-5.4 (6H, m), 7.45 (4H, d, J=8.5 Hz), 8.16 (4H, d, J=8.5 Hz)

PREPARATION 57-2

(2S,4R)-2-[{1,1-Dimethyl-2-(4-nitrobenzyloxycarbcnylamino)ethyl}oxymethyl]-4-methanesulfonyloxy-1-(4nitrobenzyloxycarbonyl)pyrrolidine (1.78 g) was obtained by reacting (2S,4R)-2-(1-carbamoyl-1-methylethyl)oxymethyl-4-methanesulfonyloxy-1-(4-nitrobenzyloxycarbonyl)pyrrolidine (1.60 g) with a mixture of sodium borohydride (0.34 g) and boron trifluoride etherate (3.25 ml) and then with 4-nitrobenzyloxycarbonyl chloride (0.75 g) in substantially the same manners as those of Preparations 7 and 8.

IR (Neat): 1725-1700, 1605 cm$^{-1}$

NMR (CDCl$_3$, δ): 1.12 (6H, s), 3.06 (3H, s), 5.20 (2H, s), 5.23 (2H, s)

PREPARATION 58-1

A solution of (2S,4R)-4-methanesulfonyloxy-1-(4-nitrobenzyloxycarbonyl)-2-[2-(4-nitrobenzyloxycarbonylamino)ethyloxymethyl]pyrrolidine (0.90 g) in dimethylformamide (2 ml) was added to a reaction mixture of thioacetic S-acid (0.16 ml) and sodium hydride (62.8% in oil suspension) (0.07 g) in dimethylformamide (9 ml) in a nitrogen stream and the mixture was heated at 70°-75° C. for 6 hours. The mixture was poured into water (100 ml), extracted with ethyl acetate (50 ml×2), dried over magnesium sulfate and concentrated under reduced pressure to give a syrup. The syrup was subjected to a column chromatography on silica gel (20 g) and eluted with chloroform to give (2S,4S)-4-acetylthio-1-(4-nitrobenzyloxycarbonyl)-2-[2-(4-nitrobenzyloxycarbonylamino)ethyloxymethyl]pyrrolidine (0.60 g).

IR (Neat): 1725-1685 cm$^{-1}$
NMR (CDCl$_3$δ): 2.30 (3H, s)

PREPARATION 58-2

Crude product of (2S,4S)-4-acetylthio-2-[{1,1-dimethyl-2-(4-nitrobenzyloxycarbonylamino)ethyl}oxymethyl]-1-(4-nitrobenzyloxycarbonyl)pyrrolidine (1.77 g) was obtained by reacting (2S,4R)-2-[{1,1-dimethyl-2-(4-nitrobenzyloxycarbonylamino)ethyl}oxymethyl]-4-methanesulfonyloxy-1-(4-nitrobenzyloxycarbonyl)pyrrolidine (1.77 g) with thioacetic S-acid in substantially the same manner as that of Preparation 58-1).

IR (Neat): 1720-1690, 1605 cm$^{-1}$
NMR (CDCl$_3$δ): 1.13 (6H, s), 2.31 (3H, s)

PREPARATION 59-1

To a solution of (2S,4S)-4-acetylthio-1-(4-nitrobenzyloxycarbonyl)-2-[2-(4-nitrobenzyloxycarbonylamino)ethyloxymethyl]pyrrolidine (0.59 g) in a mixture of methanol (12 ml) and tetrahydrofuran (12 ml) was added sodium methoxide (28% solution in methanol) (0.25 ml) at $-20°\sim-10°$ C. in a nitrogen stream and the mixture was stirred at the same condition for 1 hour. To the mixture was added glacial acetic acid (0.1 ml) at $-10°\sim0°$ C. The mixture was concentrated under reduced pressure to give a residue. The residue was dissolved in ethyl acetate (20 ml). The solution was washed with water (20 ml), dried over magnesium sulfate and concentrated under reduced pressure to give a syrup. The syrup was subjected to a column chromatography on a silica gel (10 g) and eluted with a mixture of acetone and chloroform (5:95 V/V) to give (2S,4S)-4-mercapto-1-(4-nitrobenzyloxycarbonyl)-2-[2-(4-nitrobenzyloxycarbonylamino)ethyloxymethyl]pyrrolidine (0.46 g).

IR (Neat): 1725-1690 cm$^{-1}$

PREPARATION 59-2

(2S,4S)-2-[{1,1-Dimethyl-2-(4-nitrobenzyloxycarbonylamino)ethyl}oxymethyl]-4-mercapto-1-(4-nitrobenzyloxycarbonyl)pyrrolidine (0.71 g) was obtained by reacting (2S,4S)-4-acetylthio-2-[{1,1-dimethyl-2-(4-nitrobenzyloxycarbonylamino)ethyl}oxymethyl]-1-(4-nitrobenzyloxycarbonyl)pyrrolidine (2.00 g) with 28% sodium methoxide-methanol solution (0.75 ml) in substantially the same manner as that of Preparation 59-1).

IR (Neat): 1725-1680, 1605 cm$^{-1}$
NMR (CDCl$_3$, δ): 1.13 (6H, s)

PREPARATION 60

To a solution of (2S, 4R)-2-aminomethyl-4-t-butyldimethylsilyloxy-1-(4-nitrobenzyloxycarbonyl)pyrrolidine (8.43 g) in dichloromethane (80 ml) were added t-butoxycarbonylglycine (3.61 g), 1-hydroxybenzotriazole (2.78 g) and 1-ethyl-3-(3-dimethylaminopropyl)carbodiimide hydrochloride (3.95 g) under ice-cooling. The mixture was stirred under ice-cooling for 1 hour and at ambient temperature for 15 hours. The solution was washed with water (80 ml), saturated aqueous sodium hydrogen carbonate (80 ml), and brine (80 ml) successively, dried over magnesium sulfate, and concentrated under reduced pressure to give a syrup. The syrup was subjected to a column chromatography on silica gel (80 g) and eluted with a mixture of methanol and chloroform (2:98 v/v) to give (2S, 4R)-4-t-butyldimethylsilyloxy-2-[(t-butoxycarbonylamino)methylcarbonyl]aminomethyl-1-(4-nitrobenzyloxycarbonyl)pyrrolidine (9.07 g).

IR (CHCl$_3$): 3330, 1720-1660 cm$^{-1}$
NMR (CDCl$_3$, δ): 0.03 (6H, s), 0.85 (9H, s), 1.58 (9H, s), 7.52 (2H, d, J=7.5 Hz), 8.92 (2H, d, J=7.5 Hz)

PREPARATION 61

To a solution of (2S, 4R)-4-t-butyldimethylsilyloxy-2-[(t-butoxycarbonylamino)methylcarbonyl]aminomethyl-1-(4-nitrobenzyloxycarbonyl)pyrrolidine (9.05 g) in tetrahydrofuran (90 ml) was added a 1M solution (31.9 ml) of tetrabutylammonium fluoride in tetrahydrofuran at $0°\sim10°$ C. The mixture was stirred at $0°\sim10°$ C. for 1 hour and at ambient temperature for 3 hours. The mixture was poured into a mixture of water (100 ml) and ethyl acetate (200 ml). The organic layer was separated, dried over magnesium sulfate and concentrated under reduced pressure to give a syrup. The syrup was subjected to a column chromatography on silica gel (80 g) and eluted with a mixture of methanol and dichloromethane (3:97 v/v) to give (2S,4R)-2-[(t-butoxycarbonylamino)methylcarbonyl]amino-methyl-4-hydroxy-1-(4-nitrobenzyloxycarbonyl)pyrrolidine (5.32 g).

IR (CHCl$_3$): 3400-3200, 1710-1740 cm$^{-1}$
NMR (CDCl$_3$, δ): 1.43 (9H, s)

PREPARATION 62

A solution of (2S, 4R)-2-[(t-butoxycarbonylamino)methylcarbonyl]aminomethyl-4-hydroxy-1-(4-nitrobenzyloxycarbonyl)pyrrolidine (5.30 g) in a mixture of anisole (1 ml) and trifluoroacetic acid (50 ml) was stirred at ambient temperature for 1 hour. The mixture was evaporated under reduced pressure to give (2S, 4R)-2-(aminomethylcarbonyl)aminomethyl-4-hydroxy-1-(4-nitrobenzyloxycarbonyl)pyrrolidine. To a solution of the compound obtained above in a mixture of water (25 ml) and tetrahydrofuran (25 ml) was added a solution of potassium cyanate (4.75 g) in water (15 ml) at $40°\sim50°$ C., keeping the pH between 4-5 with concentrated hydrochloric acid. Tetrahydrofuran was removed by evaporation to give an aqueous solution. The aqueous solution was adjusted to pH 6.0 with 1N hydrochloric acid, subjected to a column chromatography on nonionic adsorption resin, "Diaion HP-20" (50 ml), washed with water, and eluted with a mixture of methanol and water (50:50 v/v). The fractions containing the desired compound were collected, concentrated under reduced pressure, and recrystallized from a mixture of methanol and diisopropyl ether to give (2S, 4R)-4-hydroxy-1-(4-nitrobenzyloxycarbonyl)-2-[(ureidomethylcarbonyl)aminomethyl]pyrrolidine (3.93 g).

mp: 167°-169° C.
IR (Nujol): 3500-3200, 1685, 1660, 1640 cm$^{-1}$
MS: 395 (M+), 369 (M+ −26), 300

PREPARATION 63

To a suspension of sodium borohydride (1.38 g) in tetrahydrofuran (50 ml) was added boron trifluoride etherate (4.49 ml) in a nitrogen stream with stirring at $0°\sim5°$ C. The mixture was stirred at the same condition for 30 minutes To the mixture was added a solution of (2S, 4R)-4-hydroxy-1-(4-nitrobenzyloxycarbonyl)-2-[(ureidomethylcarbonyl)aminomethyl]pyrrolidine (2.90 g) at $0°\sim5°$ C. The mixture was stirred at $0°\sim5°$ C. for 1 hour and at ambient temperature overnight. Ethanol (30 ml) was added to the reaction mixture at $0°\sim10°$ C.

After stirring for 2 hours, insoluble material was filtered off and the filtrate was concentrated under reduced pressure to give a residue. A solution of the residue in a mixture of concentrated hydrochloric acid (2.9 ml) and methanol (29 ml) was stirred at ambient temperature for 20 hours. The mixture was concentrated under reduced pressure to give (2S, 4R)-4-hydroxy-1-(4-nitrobenzyloxycarbonyl)-2-[(2-ureidoethyl) aminomethyl]pyrrolidine hydrochloride. To a solution of the compound obtained above in a mixture of water (20 ml) and tetrahydrofuran (20 ml) was added a solution of 4-nitrobenzyloxycarbonyl chloride (1.60 g) in tetrahydrofuran (5 ml) under ice-cooling, keeping the pH between 8.5-9.5 with concentrated hydrochloric acid. The reaction mixture was extracted with ehtyl acetate (100 ml). The organic layer was washed with brine (50 ml×2), dried over magnesium sulfate, and concentrated under reduced pressure to give a syrup. The syrup was subjected to a column chromatography on silica gel (20 g) and eluted with a mixture of methanol and chloroform (5:95 v/v) to give (2S, 4R)-4-hydroxy-1-(4-nitrobenzyloxycarbonyl)-2-[N-(4-nitrobenzyloxycarbonyl)-N-(2-ureidoethyl)amino]-methylpyrrolidine (1.78 g).

IR (CHCl$_3$): 3500–3200, 1705–1650 cm$^{-1}$

PREPARATION 64

To a solution of (2S, 4R)-4-hydroxy-1-(4-nitrobenzyloxycarbonyl)-2-[N-(4-nitrobenzyloxycarbonyl)-N-(2-ureidoethyl)amino]methylpyrrolidine (1.75 g) in pyridine (17.5 ml) was added methanesulfonyl chloride (0.60 ml) at 0°~10° C. The mixture was stirred at the same temperature for 1 hour and at ambient temperature for 15 hours. The mixture was poured into a mixture of water (100 ml) and ethyl acetate (100 ml). The organic layer was washed in turn with 1N hydrochloric acid (100 ml×3), saturated sodium hydrogen carbonate (100 ml) and brine (100 ml), dried over magnesium sulfate and concentrated under reduced pressure to give a syrup. The syrup was subjected to a column chromatography on silica gel (30 g) and eluted with a mixture of methanol and chloroform (1:99 v/v) to give (2S, 4R)-2-[N-{2-(cyanoamino)ethyl}-N-(4-nitrobenzyloxycarbonyl)aminomethyl]-4-methanesulfonyloxy-1-(4-nitrobenzyloxycarbonyl)pyrrolidine (1.53 g).

IR (CHCl$_3$) : 2240, 1715–1685 cm$^{-1}$

NMR (CDCl$_3$, δ): 3.03 (3H, s), 5.20 (4H, s), 7.48 (4H, d, J=7.5 Hz), 8.20 (4H, d, J=7.5 Hz)

PREPARATION 65

To a solution of (2S, 4R)-2-[N-{2-(cyanoamino)ethyl}-N-(4-nitrobenzyloxycarbonyl)aminomethyl]-4-methanesulfonyloxy-1-(4-nitrobenzyloxycarbonyl)pyrrolidine (1.52 g) in acetone (30 ml) was added oxalic acid dihydrate (1.92 g) at ambient temperature. The mixture was stirred at the same temperature for 18 hours. Acetone was removed by evaporation to give a residue. A suspension of the syrup in ethyl acetate (100 ml) was washed in turn with 1N aqueous sodium hydroxide (50 ml×2), water (50 ml) and brine (50 ml), dried over magnesium sulfate and concentrated under reduced pressure to give a syrup. The syrup was subjected to a column chromatography on silica gel (20 g) and eluted with a mixture of methanol and chloroform (2:98 v/v) to give (2S, 4R)-4-methanesulfonyloxy-1-(4-nitrobenzyloxycarbonyl)-2-[N-(4-nitrobenzyloxycarbonyl)-N-(2-ureidoethyl)aminomethyl]pyrrolidine (1.43 g).

IR (CHCl$_3$): 3500–3200, 1710–1670 cm$^{-1}$

NMR (CDCl$_3$, δ): 3.03 (3H, s), 5.21 (4H, s), 7.52 (4H d, J=7.5 Hz), 8.22 (4H, d, J=7.5 Hz).

PREPARATION 66

(2S, 4S)-4-Acetylthio-1-(4-nitrobenzyloxycarbonyl)-2-[N-(4-nitrobenzyloxycarbonyl)-N-(2-ureidoethyl)aminomethyl]pyrrolidine (1.11 g) was obtained by reacting (2S, 4R)-4-methanesulfonyloxy-1-(4-nitrobenzyloxycarbonyl)-2-[N-(4-nitrobenzyloxycarbonyl)-N-(2-ureidoethyl)aminomethyl]pyrrolidine (1.40 g) with thioacetic S-acid (0.25 ml) in substantially the same manner as that of Preparation 58-1).

IR (CHCl$_3$): 3500–3200, 1710–1655 cm$^{-1}$

NMR (CDCl$_3$, δ): 2.32 (3H, s), 5.20 (4H, s), 7.52 (4H, d, J=7.5 Hz), 8.25 (4H, d, J=7.5 Hz).

PREPARATION 67

(2S, 4S)-4-Mercapto-1-(4-nitrobenzyloxycarbonyl)-2-[N-(4-nitrobenzyloxycarbonyl)-N-(2-ureidoethyl)aminomethyl]pyrrolidine (0.77 g) was obtained by reacting (2S, S)-4-acetylthio-1-(4-nitrobenzyloxycarbonyl)-2-[N-(4-nitrobenzyloxycarbonyl)-N-(2-ureidoethyl)aminomethyl]pyrrolidine (1.06 g) with 28% solution (0.45 ml) of sodium methoxide in methanol in substantially the same manner as that of Preparation 59-1).

IR (CHCl$_3$): 3500–3200, 1715–1655 cm$^{-1}$

NMR (CDCl$_3$, δ): 7.54 (4H, d, J=7.5 Hz), 8.25 (4H, d, J=7.5 Hz)

EXAMPLE 1

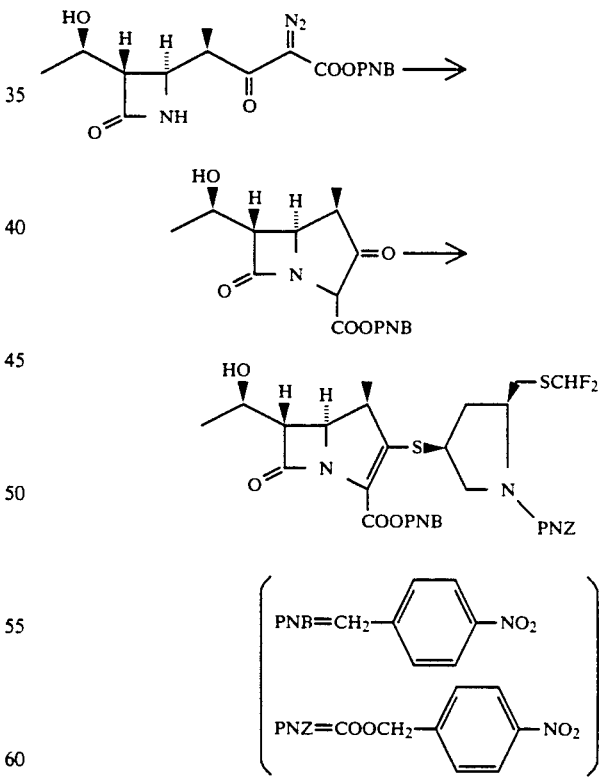

To a solution of 4-nitrobenzyl (4R)-2-diazo-4-[(2R, 3S)-3-{(1R)-1-hydroxyethyl}-4-oxoazetidin-2-yl]-3-oxopentanoate (0.5 g) in 1,2-dichloroethane (10 ml) was added rhodiim(II) acetate (2 mg) under refluxing. After refluxing for 30 minutes, the reaction mixture was cooled and evaporated in vacuo to give a residue. The residue was dissolved in anhydrous benzene (10 ml) and then evaporated. This operation was repeated once again and the residue was dried in vacuo to give 4-nitrobenzyl (4R,5R,6S)-6-[(1R)-1-hydroxyethyl]-4-methyl-3,7-dioxo-1-azabicyclo[3.2.0]heptane-2-carboxylate.

The compound obtained above was dissolved in anhydrous acetonitrile (10 ml) and cooled to 0° C. under an atmosphere of nitrogen. To this solution were added N,N-diisopropyl-N-ethylanine (0.27 ml) and diphenyl phosphorochloridate (0.28 ml) successively, and the solution was stirred at 0° C. for 40 minutes. To the resulting solution were added dropwise a solution of (2S,4S)-2-(difluoromethyl)thiomethyl-4-mercapto-1-(4-nitrobenzyloxycarbonyl)pyrrolidine (0.54 g) in anhydrous acetonitrile (3 ml) and N,N-diisopropyl-N-ethylamine (0.29 ml) at 5° C. with stirring, and the stirring was continued at the same temperature for 2 hours. To the reaction mixture was added ethyl acetate (30 ml). The solution was washed twice with saturated aqueous sodium chloride (20 ml), dried over anhydrous magnesium sulfate and evaporated. The oily residue was chromatographed on silica gel (60 g) eluting with a mixture of dichloromethane and acetone (5:1,V/V) to give 4-nitrobenzyl (4R,5S,6S)-3-[(2S,4S)-2-(difluoromethyl)thiomethyl-1-(4-nitrobenzyloxycarbonyl)pyrrolidin-4-ylthio]-6-[(1R)-1-hydroxyethyl]-4-methyl-7-oxo-1-azabicyclo[3.2.0]hept-2-ene-2-carboxylate (0.58 g).

IR (Nujol): 1770, 1760, 1710, 1690, 1610, 1525, 1350 cm$^{-1}$

NMR (CDCl$_3$, δ): 1.30 (3H, d, J=7 Hz), 1.35 (3H, d, J=7 Hz), 1.70–2.10 (2H, m), 5.15–5.50 (4H, m), 6.80 (1H, t, J=56 Hz), 7.53 (2H, d, J=8 Hz), 7.65 (2H, d, J=8 Hz), 8.37 (4H, d, J=8 Hz)

EXAMPLE 2

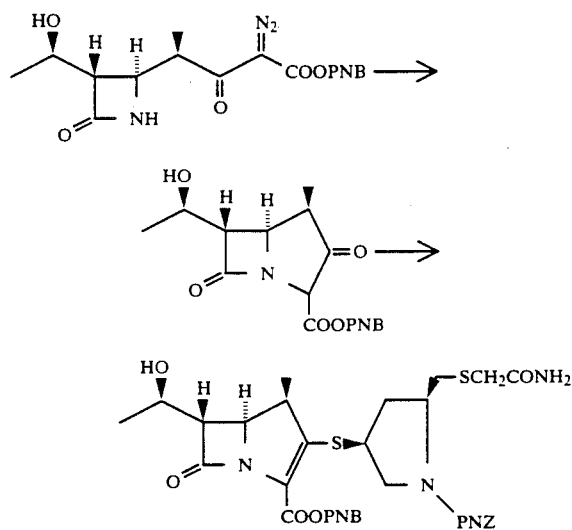

To a solution of 4-nitrobenzyl (4R)-2-diazo-4-(2R,3S)-3-{(1R)-1 hydroxyethyl}-4-oxoazetidin-2-yl]-3oxopentanoate (0.4 g) in 1,2-dichloroethane was added rhodium(II) acetate (1 mg) under refluxing. After refluxing for 1 hour, the reaction mixture was cooled and evaporated in vacuo to give a residue. The residue was dissolved in anhydrous benzene (10 ml) and then evaporated in vacuo. This operation was repeated once again and the residue was dried in vacuo to give 4-nitrobenzyl (4R,5R,6S)-6-[(1R)-1-hydroxyethyl]-4-methyl-3,7-dioxo-1-azabicyclo[3.2.0]heptane-2-carboxylate. 3,7-dioxo-1-azabicyclo[3.2.0]heptane-2-carboxylate. The compound obtained above was dissolved in anhydrous acetonitrile (10 ml) and cooled to 0° C. under an atmosphere of nitrogen. To this solution were added N,N-diisopropyl-N-ethylamine (0.21 ml) and diphenyl phosphorochloridate (0.22 ml) successively, and the solution was stirred at 0° C. for 40 minutes. To the resulting solution were added dropwise a solution of (2S,4S)-2-(carbamoylmethyl)thiomethyl-4-mercapto-1-(4-nitrobenzyloxycarbonyl)pyrrolidine (0.45 g) in N,N-dimethylformamide (3 ml) and N,N-diisopropyl-N-ethylamine (0.21 ml) at 0°-2° C. with stirring and the stirring was continued at the same temperature for 2 hours. To the reaction mixture was added ethyl acetate (30 ml). The solution was washed 3 times with saturated aqueous sodium chloride (20 ml), dried over anhydrous magnesium sulfate and evaporated in vacuo to give a residue. The residue was chromatographed on silica gel (60 g) eluting with a mixture of dichloromethane and acetone (1:1,V/V). The fractions containing the desired compound were collected and evaporated in vacuo to give 4-nitrobenzyl (4R,5S,6S)-3-[(2S,4S)-2-(carbamoylmethyl)thiomethyl-1-(4-nitrobenzyloxycarbonyl)pyrrolidin-4-ylthio]-6-[(1R)-1-hydroxyethyl]-4-methyl-7-oxo-1-azabicyclo[3.2.0]hept-2-ene-2-carboxylate (0.44 g).

IR (Nujol): 1760, 1710–1700, 1690–1670, 1610, 1540–1515 cm$^{-1}$

NMR (CDCl$_3$, δ): 1.26 (3H, d, J=7 Hz), 1.35 (3H, d, J=7 Hz), 1.55–2.10 (6H, m), 3.20 (2H, s), 3.20–3.50 (3H, m), 3.85–4.40 (4H, m), 5.10–5.70 (4H, m), 7.53 (2H, d, J=7 Hz), 7.65 (2H, d, J=7 Hz), 8.24 (4H, d, J=7 Hz)

EXAMPLE 3

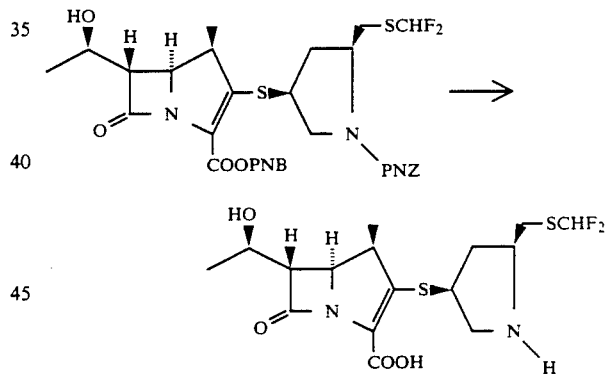

A mixture of 4-nitrobenzyl (4R,5S,6S)-3-[(2S,4S)-2-(difluoromethyl)thiomethyl-1-(4-nitrobenzyloxycarbonyl)pyrrolidin-4-ylthio]-6-[(1R)-1-hydroxyethyl]-4-methyl-7-oxo-1-azabicyclo[3.2.0]hept-2-ene-2-carboxylate (0.58 g), 20% palladium hydroxide on carbon (0.5 g), 0.05M phosphate buffer (pH 6.3, 18 ml) and tetrahydrofuran (18 ml) was stirred at ambient temperature for 4 hours under atmospheric pressure of hydrogen. After the catalyst was filtered off, the filtrate was concentrated under reduced pressure to remove the organic solvent. The resulting aqueous residue was washed with ethyl acetate (10 ml×2) and the aqueous layer was concentrated under reduced pressure to remove the organic solvent. The residue was chromatographed on nonionic adsorption resin "Diaion HP-20" (Trademark, made by Mitsubishi Chemical Industries) (20 ml) eluting in turn with water (80 ml) and 6% aqueous acetone (80 ml). The fractions containing the desired compound were collected and lyophilized to give (4R,5S,6-

S)-3-[(2S,4S)-2-(difluoromethyl)thiomethylpyrrolidin-4-ylthio]-6-[(1R)-1-hydroxyethyl]-4-methyl-7-oxo-1-azabicyclo[3.2.0]hept-2-ene-2-carboxylic acid (0.19 g).

mp: >165° C. (dec.)

IR (Nujol): 1760, 1590, 1180, 1150 cm$^{-1}$

NMR (D$_2$O, δ): 1.22 (3H, d, J=7 Hz), 1.28 (3H, d, J=7 Hz), 1.71–1.86 (1H, m), 2.74–2.95 (1H, m), 3.20 (1H, dd, J=10, 15 Hz), 3.28–3.50 (3H, m), 3.69 (1H, dd, J=8, 12 Hz), 3.90–4.10 (2H, m), 4.18–4.30 (2H, m), 7.11 (1H, t, J=55 Hz)

SI Mass: 407 (M$^+$), 363 (M$^+$ −44)

EXAMPLE 4

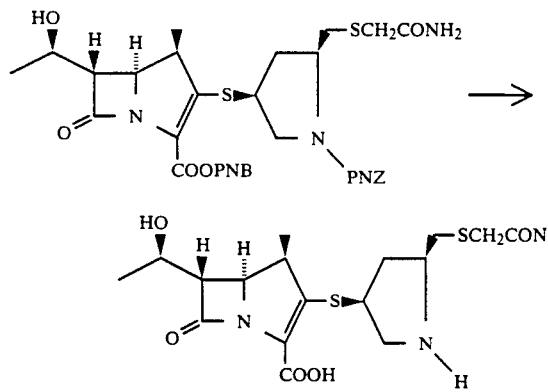

A mixture of 4-nitrobenzyl (4R,5S,6S)-3-[(2S,4S)-2-(carbamoylmethyl)thiomethyl-1-(4-nitrobenzyloxycarbonyl)pyrrolidin -4-ylthio]-6-[(1R)-1-hydroxyethyl]-4-methyl-7-oxo-1-azabicyclo[3.2.0]hept-2-ene-2-carboxylate (0.42 g), 20% palladium hydroxide on carbon (0.4 g), 0.05M phosphate buffer (pH 6.3, 20 ml), and tetrahydrofuran (20 ml) was stirred at ambient temperature for 4 hours under atmospheric pressure of hydrogen. After the catalyst was filtered off, the filtrate was concentrated under reduced pressure to remove the organic solvent. The resulting residue was washed twice with ethyl acetate (20 ml) and the aqueous layer was concentrated under reduced pressure to remove the organic solvent. The residue was chromatographed on nonionic adsorption resin "Diaion HP-20" (Trademark, made by Mitsubishi Chemical Industries) (20 ml) eluting in turn with water (100 ml) and 5% aqueous acetone (100 ml). The fractions containing the desired compound were collected and lyophilized to give (4R,5S,6S)-3-[(2S,4S)-2-(carbamoylmethyl)thiomethylpyrrolidin-4-ylthio]-6-[(1R)-1-hydroxyethyl]-4-methyl-7-oxo-1-azabicyclo[3.2.0]hept-2-ene-2-carboxylic acid (0.16 g).

mp: 171°–174° C. (dec.)

IR (Nujol): 1750, 1670, 1580, 1150 cm$^{-1}$

NMR (D$_2$O, δ): 1.21 (3H, d, J=7 Hz), 1.27 (3H, d, J=7 Hz), 1.45–2.00 (2H, m), 2.55–3.20 (5H, m), 3.39 (2H, s)

EXAMPLE 5

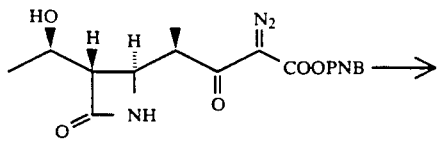

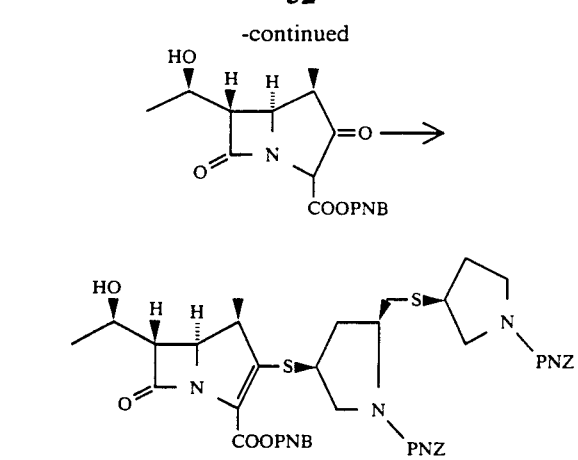

4-Nitrobenzyl (4R,5S,6S)-6-[(1R)-1-hydroxyethyl]-4-methyl-3-[(2S,4S)-1-(4-nitrobenzyloxycarbonyl)-2-[{(3S)-1-(4-nitrobenzyloxycarbonyl)pyrrolidin-3-ylthio}methyl]-pyrrolidin-4-ylthio]-7-oxo-1-azabicyclo[3.2.0]hept-2-ene-2carboxylate (0.32 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.30 g) with rhodium(II) acetate (1 mg), and then successively with diphenyl phosphorochloridate (0.17 ml) and (2S,4S)-4-mercapto-1-(4-nitrobenzyloxycarbonyl)-2-[{(3S)-1-(4-nitrobenzyloxycarbonyl)pyrrolidin-3-ylthio}methyl]pyrrolidine (0.41 g) in substantially the same manner as that of Example 2.

IR (Neat): 1775–1760, 1710, 1690, 1610, 1520 cm$^{-1}$

NMR (CDCl$_3$, δ): 1.30 (3H, d, J=7 Hz), 1.38 (3H, d, J=7 Hz), 1.75–2.10 (3H, m), 2.80–3.90 (11H, m), 3.90–4.40 (4H, m), 5.20–5.50 (6H, m), 7.55 (4H, d, J=8 Hz), 7.66 (2H, d, J=8 Hz), 8.25 (6H, d, J=8 Hz)

EXAMPLE 6

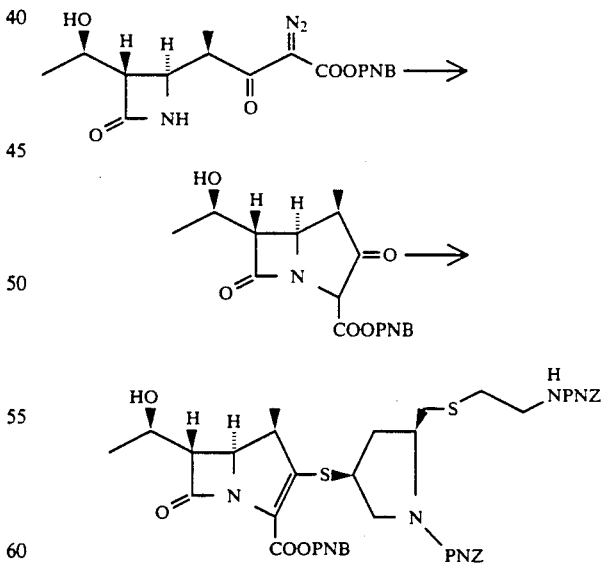

4-Nitrobenzyl (4R,5S,6S)-6-[(1R)-1-hydroxyethyl]-4-methyl 3-[(2S,4S)-1 (4-nitrobenzyloxycarbonyl)-2-[{2 (4-nitrobenzyloxycarbonylamino)ethylthio}methyl]-pyrrolidin-4-ylthio]-7-oxo-1-azabicyclo[3.2.0]hept-2-ene-2-carboxylate (0.22 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.30 g) with rhodium(II) acetate (1 mg), and then successively with diphenyl phosphorochloridate (0.17 ml) and (2S,4S)-4-mercapto-1-(4-nitrobenzyloxycarbonyl)-2-[{2-(4-nitrobenzyloxycarbonylamino)ethylthio}methyl]pyrrolidine (0.46 g) in substantially the same manner as that of Example 2.

IR (Neat): 1765-1750, 1710, 1660-1640, 1530-1510 cm$^{-1}$

EXAMPLE 7

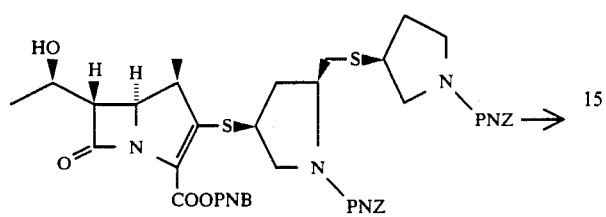

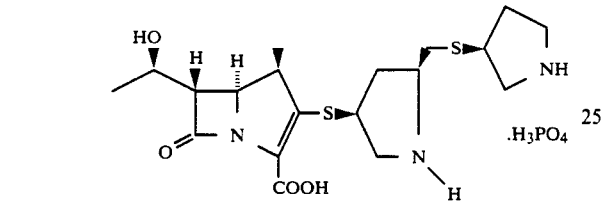

(4R,5S,6S)-6-[(1R)-1-Hydroxyethyl]-4-methyl-7-oxo-3-[(2S,4S)-2-{(3S)-pyrrolidin-3-ylthiomethyl}pyrrolidin-4-ylthio]-1-azabicyclo[3.2.0]hept-2-ene-2-carboxylic acid phosphate (61.4 mg) was obtained by hydrogenating 4-nitrobenzyl (4R,5S,6S)-6-[(1R)-1-hydroxyethyl]-4-methyl-3-[(2S,4S)-1-(4-nitrobenzyloxycarbonyl)-2-[{(3S)-1-(4-nitrobenzyloxycarbonyl)pyrrolidin-3-ylthio}methyl]-pyrrolidin-4-ylthio]-7-oxo-1-azabicyclo[3.2.0]hept-2-ene-2-carboxylate (350 mg) in substantially the same manner as that of Example 4.

IR (Nujol): 1760-1740, 1580 cm$^{-1}$

NMR (D$_2$O, δ): 1.22 (3H, d, J=7 Hz), 1.29 (3H, d, J=7 Hz), 1.46-1.95 (2H, m)

EXAMPLE 8

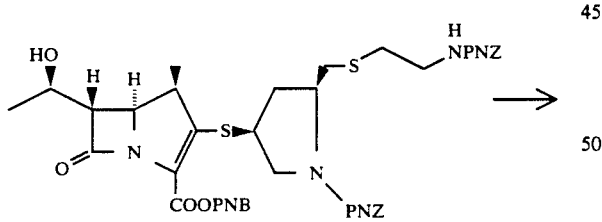

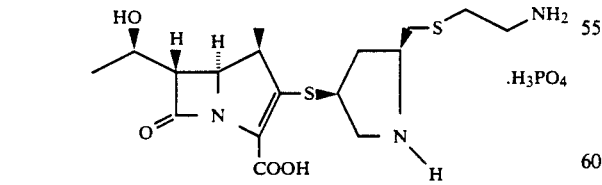

(4R,5S,6S)-3-[(2S,4S)-2-{(2-Aminoethylthio)methyl}-pyrrolidin-4-ylthio]-6-[(1R)-1-hydroxyethyl]-4-methyl-7-oxo-1-azabicyclo[3.2.0]hept-2-ene-2-carboxylic acid phosphate (0.04 g) was obtained by hydrogenating 4-nitrobenzyl (4R,5S,6S)-6-[(1R)-1-hydroxyethyl]-4-methyl-3-[(2S,4S)-1-(4-nitrobenzyloxycarbonyl)-2-[{2-(4-nitrobenzyloxycarbonylamino)ethylthio}methyl]pyrrolidin-4-ylthio]-7-oxo-1-azabicyclo[3.2.0]hept-2-ene-2-carboxylate (0.20 g) in substantially the same manner as that of Example 4.

mp: >178° C. (dec.)

IR (Nujol): 1750, 1590-1580 cm$^{-1}$

NMR (D$_2$O, δ): 1.22 (3H, d, J=7 Hz), 1.30 (3H, d, J=7 Hz), 1.45-1.95 (2H, m), 2.55-3.08 (5H, m), 3.12-4.35 (9H, m)

SI Mass: 402 (M$^+$)

EXAMPLE 9

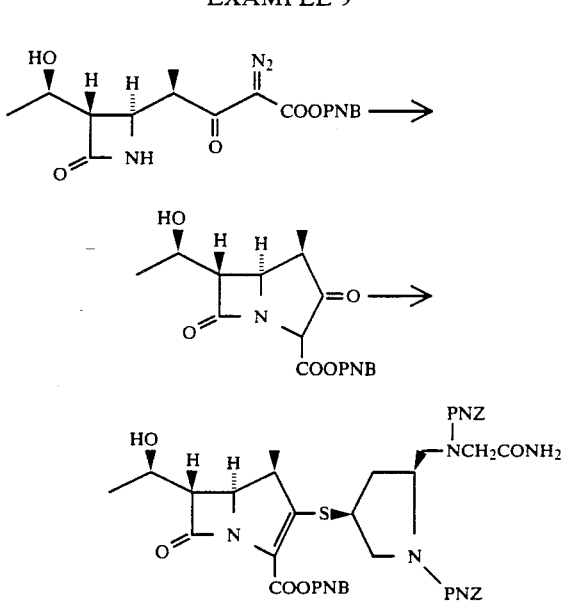

4-Nitrobenzyl (4R,5S,6S)-3-[(2S,4S)-2-{N-carbamoylmethyl-N-(4-nitrobenzyloxycarbonyl)-}aminomethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (1.05 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.85 g) with rhodium(II) acetate (1 mg), and then successively with diphenyl phosphorochloridate (0.47 ml) and (2S,4S)-2-[N-carbamoylmethyl-N-(4-nitrobenzyloxycarbonyl)]aminomethyl-4-mercapto-1-(4-nitrobenzyloxycarbonyl)pyrrolidine (1.43 g) in substantially the same manner as that of Example 2.

IR (Nujol): 1755, 1710-1700, 1610, 1520, 1350 cm$^{-1}$

NMR (CDCl$_3$, δ): 1.24 (3H, d, J=7 Hz), 1.36 (3H, d, J=7 Hz), 3.15-3.46 (3H, m), 3.56-4.40 (12H, m), 5.12-5.50 (6H, m), 7.36-7.80 (6H, m), 8.24 (6H, d, J=8 Hz)

EXAMPLE 10

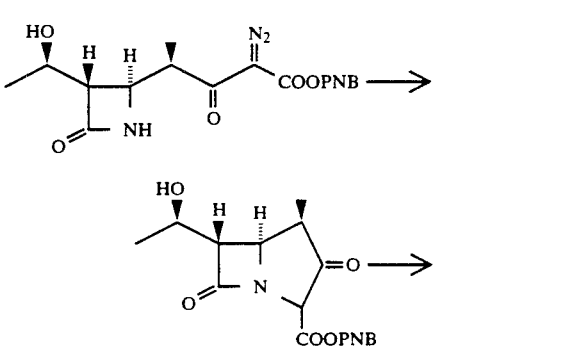

-continued

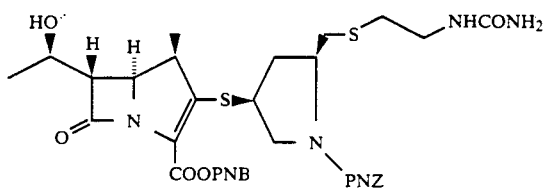

4-Nitrobenzyl (4R,5S,6S)-3-[(2S,4S)-2-(2-ureidoethyl)thiomethyl -1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.97 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.90 g) with rhodium(II) acetate (1 mg), and then successively with diphenyl phosphorochloridate (0.50 ml) and (2S,4S)-4-mercapto-2-(2-ureidoethyl)thiomethyl-1-(4-nitrobenzyloxycarbonyl)-pyrrolidine (1.05 g) in substantially the same manner as that of Example 2.

IR (Nujol): 1770, 1705, 1610, 1525, 1350 cm$^{-1}$

NMR (CDCl$_3$, δ): 1.25 (3H, d, J=7 Hz), 1.32 (3H, d, J=6 Hz), 3.10-4.38 (11H, m), 4.81 (2H, br s), 5.24 (2H, s), 5.38 (2H, dd, J=14, 29 Hz), 7.56 (2H, d, J=8 Hz), 7.68 (2H, d, J=8 Hz), 8.26 (4H, d, J=8 Hz)

EXAMPLE 11

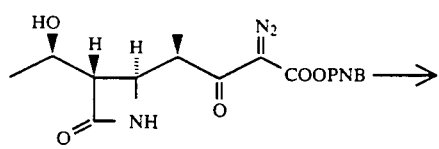

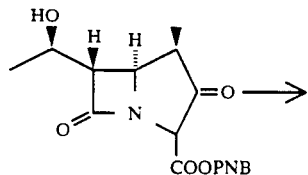

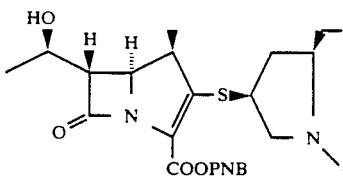

4-Nitrobenzyl (4R,5S,6S)-3-[(2S,4S)-2-(carbamoylmethyl)oxymethyl-1-(4-nitrobenzyloxycarbonyl)-pyrrolidin-4-yl]thio-6-[1R)-1-hydroxyethyl]-4-methyl-7-oxo-1-azabicyclo[3.2.0]hept-2-ene-2-carboxylate (0.75 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.62 g) with rhodium(II) acetate (2 mg), and then successively with diphenyl phosphorochloridate (0.35 ml) and (2S,4S)-2-(carbamoylmethyl)oxymethyl-4-mercapto-1-(4-nitrobenzyloxycarbonyl)-pyrrolidine (0.58 g) in substantially the same manner as that of Example 2.

mp: 58°-64° C.

IR (KBr): 1765, 1705-1675 cm$^{-1}$

NMR (D$_2$O, δ): 1.29 (3H, d, J=6 Hz), 1.36 (3H, d, J=6.5 Hz), 3.94 (2H, s), 7.45 (2H, d, J=8.5 Hz), 7.61 (2H, d, J=8.5 Hz), 8.18 (4H, d, J=8.5 Hz)

EXAMPLE 12

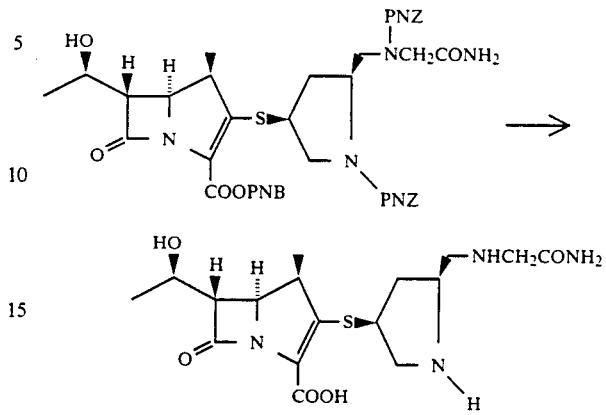

(4R,5S,6S)-3-[(2S,4S)-2-{(N-Carbamoylmethyl)aminomethyl}pyrrolidin-4-ylthio]-6-[(1R)-1-hydroxyethyl]-4-methyl-7-oxo-1-azabicyclo[3.2.0]hept-2-ene-2-carboxylic acid (0.30 g) was obtained by hydrogenating 4-nitrobenzyl (4R,5S,6S)-3-[(2S,4S)-2-(N-carbamoylmethyl-N-(4-nitrobenzyloxycarbonyl)}aminomethyl-1-(4-nitrobenzyloxycarbonyl)pyrrolidin- 4-yl]thio-6-[(1R)-1-hydroxyethyl]-4-methyl-7-oxo-1-azabicyclo[3.2.0]hept-2-ene-2-carboxylate (1.03 g) in substantially the same manner as that of Example 4.

mp: >188° C. (dec.)

IR (Nujol): 1760-1750, 1660-1640 cm$^{-1}$

NMR (D$_2$, δ): 1.22 (3H, d, J=6 Hz), 1.30 (3H, d, J=6 Hz), 1.55-2.05 (2H, m), 2.50-2.96 (2H, m), 3.00-4.40 (10H, m)

EXAMPLE 13

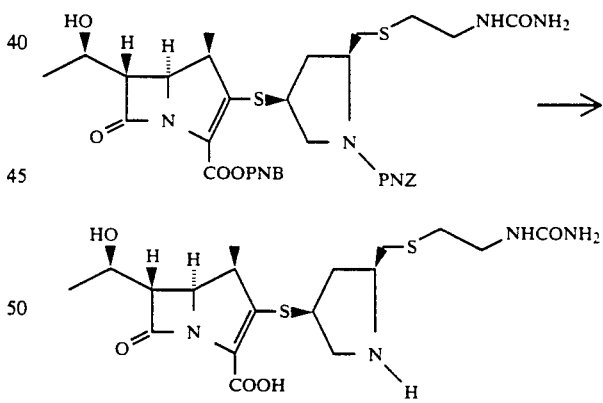

(4R,5S,6S)-3-[(2S,4S)-2-{(2-Ureidoethyl)thiomethyl}-pyrrolidin-4-yl]thio-6-[(1R)-1-hydroxyethyl]-4-methyl-7-oxo-1-azabicyclo[3.2.0]hept-2-ene-2-carboxylic acid (0.30 g) was obtained by hydrogenating 4-nitrobenzyl (4R,5S,6S)-3-[(2S,4S)-2-(2-ureidoethyl)thiomethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.95 g) in substantially the same manner as that of Example 4.

mp: >169° C. (dec )

IR (Nujol): 1755, 1650, 1580 cm$^{-1}$

NMR (D$_2$O, δ): 1.21 (3H, d, J=9 Hz), 1.27 (3H, d, J=6 Hz), 1.42-2.03 (2H, m), 2.53-4.36 (14H, m)

SI Mass: 445 (M$^+$), 444 (M$^+$−1), 443 (M$^+$−2)

EXAMPLE 14

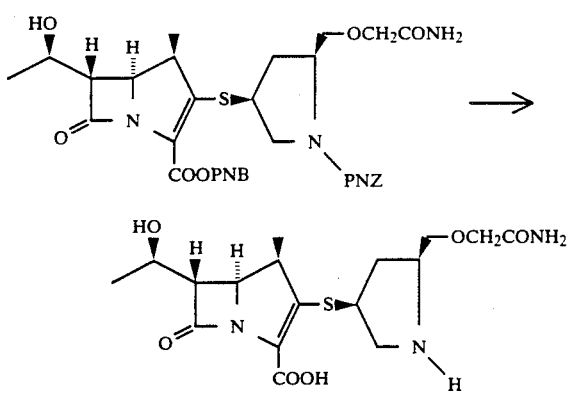

(4R,5S,6S)-3-[(2S,4S)-2-{(carbamoylmethyl)oxymethyl}pyrrolidin-4-yl]thio-6-[(1R)-1-hydroxyethyl]-4-methyl-7-oxo-1-azabicyclo[3.2.0]hept-2-ene-2-carboxylic acid (0.33 g) was obtained by hydrogenating 4-nitrobenzyl (4R,5S,6S)-3-[(2S,4S)-2-(carbamoylmethyl)oxymethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.73 g) in substantially the same manner as that of Example 4.

mp: 165° C. (dec.)

IR (KBr): 1745, 1670, 1585 cm$^{-1}$

NMR (D$_2$O, δ): 1.19 (3H, d, J=6.5 Hz), 1.26 (3H, d, J=6.5 Hz), 1.6-2.0 (1H, m), 2.5-2.9 (1H, m)

SI Mass: 400 (M$^{30}$ +1)

The following compounds were obtained in substantially the same manner as that of Example 2.

EXAMPLE 15

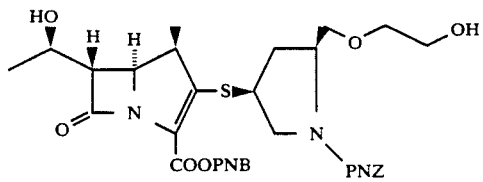

4-Nitrobenzyl (4R,5S,6S)-6-[(1R)-1-hydroxyethyl]-3-[2S,4S)-2-(2-hydroxyethyloxymethyl)-1-(4-nitrobenzyloxy-carbonyl)pyrrolidin-4-yl]thio-4-methyl-7-oxo-1-azabicyclo[3.2.0]hept-2-ene-2-carboxylate IR (Nujol): 3400, 1740-1770, 1680-1710, 1605 cm$^{-1}$ NMR (CDCl$_3$, δ): 1.1-1.6 (6H, m), 5.1-5.6 (4H, m), 7.3-7.7 (4H, m), 8.21 (4H, d, J=9 Hz)

EXAMPLE 16

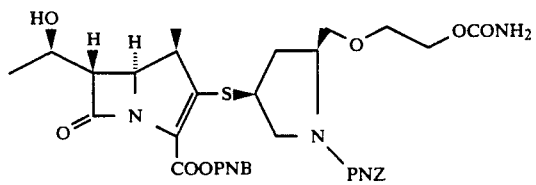

4-Nitrobenzyl (4R,5S,6S)-3-[(2S,4S)-2-(2-carbamoyloxyethyloxymethyl)-1-(4-nitrobenzyloxycarbonyl)-pyrrolidin-4-yl]thio-6-[(1R)-1-hydroxyethyl]-4-methyl-7-oxo-1-azabicyclo[3.2.0]hept-2-ene-2-carboxylate IR (CH$_2$Cl$_2$): 3400-3500, 1765, 1700-1720, 1605 cm$^{-1}$ NMR (CDCl$_3$, δ): 1.1-1.7 (6H, m), 5.0-5.6 (4H, m), 7.4-7.8 (4H, m), 8.21 (4H, d, J=8.5 Hz)

EXAMPLE 17

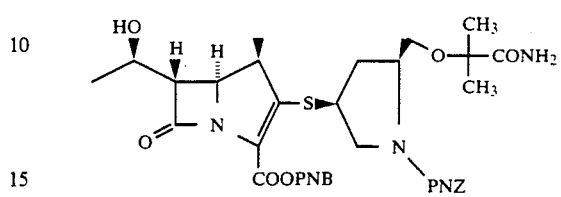

4-Nitrobenzyl (4R,5S,6S)-3-[(2S,4S)-2-(1-carbamoyl-1-ethylethyl)oxymethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate IR (CHCl$_3$) 1770, 1710-1680 cm$^{-1}$

EXAMPLE 18

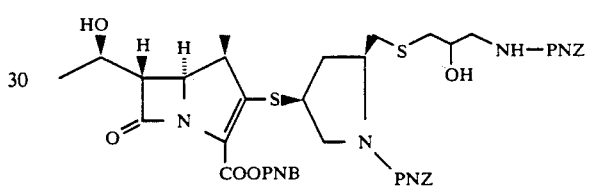

4-Nitrobenzyl (4R,5S,6S)-3-[(2S,4S)-2-{2-hydroxy-3-(4-nitrobenzyloxycarbonylamino)propyl}thiomethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate NMR (CDCl$_3$, δ): 1.26 (3H, d, J=9 Hz), 1.36 (3H, d, J=6 Hz), 5.15-5.45 (6H, m), 7.40-7.75 (6H, m), 8.25 (6H, d, J=8 Hz)

EXAMPLE 19

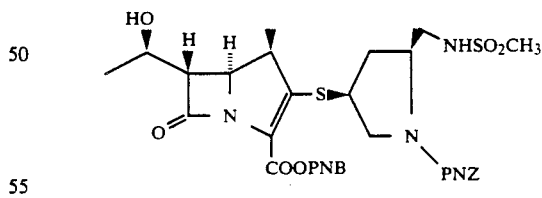

4-Nitrobenzyl (4R,5S,6S)-6-[(1R)-1-hydroxyethyl]-3-[(2S,4S)-2-(methylsulfonylamino)methyl-1-(4-nitrobenzyloxycarbonyl)pyrrolidin-4-yl]thio-4-methyl-7-oxo-1-azabicyclo[3.2.0]hept-2-ene-2-carboxylate IR (Nujol): 1770-1750, 1710-1690, 1605, 1520 cm$^{-1}$ NMR (CDCl$_3$, δ): 1.28 (3H, d, J=7 Hz), 1.37 (3H, d, J=7 Hz), 1.65-2.10 (3H, m), 2.35-2.85 (2H, m), 2.94 (3H, s), 5.25 (4H, s), 5.40-5.75 (2H, m), 7.56 (2H, d, J=9 Hz), 7.66 (2H, d, J=9 Hz), 8.26 (4H, d, J=9 Hz)

The following compounds were obtained in substantially the same manner as that of Example 4.

EXAMPLE 20

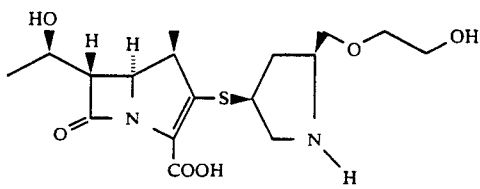

(4R,5S,6S)-6-[(1R)-1-hydroxyethyl]-3-[(2S,4S)-2-(2-hydroxyethyloxymethyl)pyrrolidin-4-yl]thio-4-methyl-7-oxo-1-azabicyclo[3.2.0]hept-2-ene-2-carboxylic acid
mp: 170°-175° C. (dec.)
IR(KBr): 1730-1760, 1570-1590 cm$^{-1}$
NMR (D$_2$O, δ): 1.21 (3H, d, J=8 Hz), 1.28 (3H, d, J=7 Hz), 1.5-2.1 (1H, m), 2.4-2.9 (1H, m)
SIMS: 387 (M$^+$+1)

EXAMPLE 21

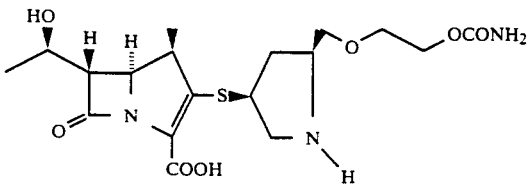

(4R,5S,6S)-3-[(2S,4S)-2-(2-carbamoyloxyethyloxymethyl)pyrrolidin-4-yl]thio-6-[(1R)-1-hydroxyethyl]-4-methyl-7-oxo-1-azabicyclo[3.2.0]hept-2-ene-2-carboxylic acid
mp: 145°-155° C. (dec.)
IR (KBr): 1750, 1705-1725, 1580 cm$^{-1}$
NMR (D$_2$O, δ): 1.22 (3H, d, J=7 Hz), 1.28 (3H, d, J=6 Hz), 1.6-1.9 (1H, m), 2.4-2.9 (1H, m)
SIMS: 430 (M$^+$+1)

EXAMPLE 22

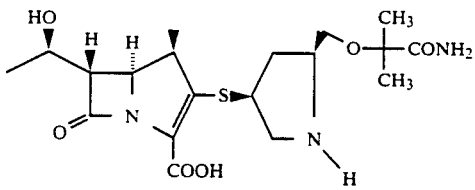

(4R,5S,6S)-3-[(2S,4S)-2-(1-carbamoyl-1-methylethyl)oxymethylpyrrolidin-4-yl]thio-6-[(1R)-1-hydroxyethyl]-4-methyl-7-oxo-1-azabicyclo[3.2.0]hept-2-ene-2-carboxylic acid
mp: 175° C. (dec.)
IR (KBr): 1755-1730, 1670-1645 cm$^{-1}$
NMR (D$_2$O, δ): 1.18 (3H, d, J=7 Hz), 1.28 (3H, d, J=7 Hz), 1.44 (6H, s)

EXAMPLE 23

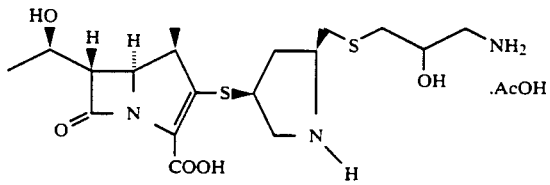

(4R,5S,6S)-3-[(2S,4S)-2-(3-amino-2-hydroxypropyl)-thiomethylpyrrolidin-4-yl]thio-6-[(1R)-1-hydroxyethyl]-4-methyl-7-oxo-1-azabicyclo[3.2.0]hept-2-ene-2-carboxylic acid
IR (Nujol): 1755-1740, 1585-1560 cm$^{-1}$
NMR (D$_2$O, δ): 1.22 (3H, d, J=8 Hz), 1.28 (3H, d, J=6 Hz), 1.55-2.00 (2H, m), 1.92 (3H, s)

EXAMPLE 24

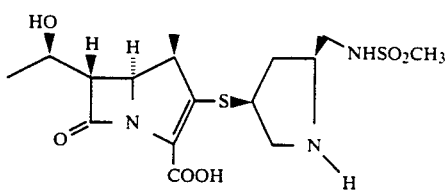

(4R,5S,6S)-6-[(1R)-1-hydroxyethyl]-3-[(2S,4S)-2-(methylsulfonylamino)methylpyrrolidin-4-yl]thio-4-methyl-7-oxo-1-azabicyclo[3.2.0]hept-2-ene-2-carboxylic acid
mp: >178° C.
IR (Nujol): 1760-1750, 1590-1580, 1150 cm$^{-1}$
NMR (D$_2$O, δ): 1.22 (3H, d, J=7 Hz), 1.28 (3H, d, J=6 Hz), 1.45-2.00 (2H, m), 2.46-2.95 (1H, m), 3.13 (3H, s)
SIMS: 420 (M$^+$)

EXAMPLE 25

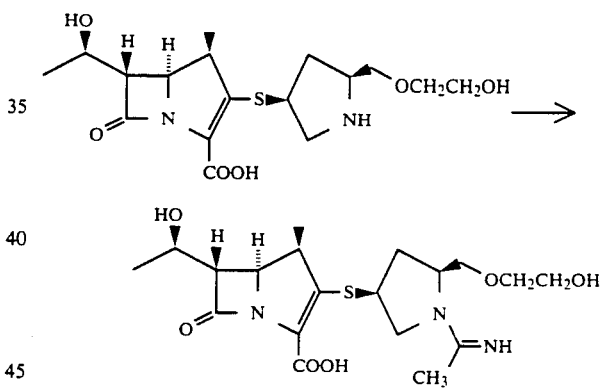

A solution of (4R,5S,6S)-6-[(1R)-1-hydroxyethyl]-3-[(2S,4S)-2-(2-hydroxyethyloxymethyl)pyrrolidin-4-ylthio]-4-methyl-7-oxo-1-azabicyclo[3.2.0]hept-2-ene-2-carboxylic acid (300 mg) in 0.05M phosphate buffer (pH 7, 30 ml) was adjusted to pH 8.5 with 30% potassium carbonate at 0° C., and ethyl acetimidate hydrochloride (3 g) was added in portions, while adjusting the mixture to around pH 8.5. After stirring for 1 hour, the reaction mixture was neutralized with 1N hydrochloric acid and washed with ethyl acetate and concentrated in vacuo. The residue was chromatographed on nonionic adsorption resin "Diaion HP-20" eluting successively with water and 5% aqueous acetone. The fractions containing the desired compound were collected and lyophilized to give (4R,5S,6S)-3-[(2S,4S)-1-acetimidoyl-2-(2-hydroxyethyloxymethyl)pyrrolidin-4-ylthio]-6-[(1R)-1-hydroxyethyl]-4-methyl-7-oxo-1-azabicyclo[3.2.0]hept-2-ene-2-carboxylic acid (290 mg).
IR (KBr): 3100-3400, 1730-1750, 1580 cm$^{-1}$ -continued NMR (D₂O, δ): 1.19 (3H, d, J=7Hz), 1.28 (3H, d, J=6Hz), 2.28 (s) / 2.39 (s) { (3H), 2.5-2.9 (1H, m)

SI Mass: 426 (M⁺ −1)

EXAMPLE 26

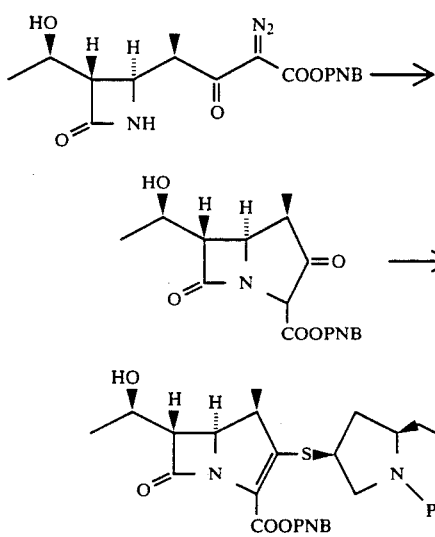

To a solution of 4-nitrobenzyl (4R)-2-diazo-4-[(2R,3S)-3-{(1R)-1-hydroxyethyl}-4-oxoazetidin-2-yl]-3-oxopentanoate (0.6 g) in anhydrous 1,2-dichloroethane (12 ml) was added rhodium(II) acetate (2 mg) under refluxing. After refluxing for 20 minutes, the reaction mixture was cooled and evaporated in vacuo to give a residue. The residue was dissolved in anhydrous benzene (10 ml) and then evaporated. This operation was repeated once again and the residue was dried in vacuo to give 4-nitrobenzyl (4R,5R,6S)-6-[(1R)-1-hydroxyethyl]-4-methyl-3,7-dioxo-1-azabicyclo[3.2.0]heptane-2-carboxylate. The compound obtained above was dissolved in anhydrous acetonitrile (15 ml) and cooled to 0° C. under an atmosphere of nitrogen. To this solution were added N,N-diisopropyl-N-ethylamine (0.32 ml) and diphenyl phosphorochloridate (0.33 ml) successively, and the solution was stirred at 0° C. for 40 minutes. To the resulting solution were added dropwise a solution of (2S,4S)-4-mercapto-2-(1-methyl-1H-tetrazol-5-yl)thiomethyl-1-(4-nitrobenzyloxycarbonyl)-pyrrolidine (0.76 g) in anhydrous acetonitrile (3 ml) and N,N-diisopropyl-N-ethylamine (0.32 ml) with stirring at 0°-2° C., and the stirring was continued at the same temperature for 2 hours. Ethyl acetate (50 ml) was added to the reaction mixture. The mixture was washed twice with saturated aqueous sodium chloride, dried over anhydrous magnesium sulfate, and evaporated in vacuo. The resulting residue was chromatographed on silica gel (100 g) eluting with a mixture of dichloromethane and acetone (5:1, V/V). The fractions containing the desired compound were collected and evaporated in vacuo to give 4-nitrobenzyl (4R,5S,6S) TM 3-[(2 S,4S)-2-(1-methyl-1H-tetrazol-5-yl)thiomethyl-1-(4-nitrobenzyloxycarbonyl)pyrrolidin-4-yl]thio-4-methyl-6-[(1R)-1-hydroxyethyl]-7-oxo-1-azabicyclo[3.2.0]hept-2-ene-2-carboxylate (0.81 g).

IR (Neat): 1765, 1710-1700, 1660, 1610, 1525, 1350 cm⁻¹

NMR (CDCl₃, δ): 1.39 (3H, d, J=7 Hz), 1.36 (3H, d, J=7 Hz), 1.63 (1H, m), 3.20-3.42 (2H, m), 3.93 (3H, s), 4.10-4.40 (4H, m), 5.13-5.66 (4H, m), 7.66 (4H, d, J=8 Hz), 8.26 (4H, d, J=8 Hz)

The following compounds were obtained in substantially the same manner as that of Example 26.

EXAMPLE 27

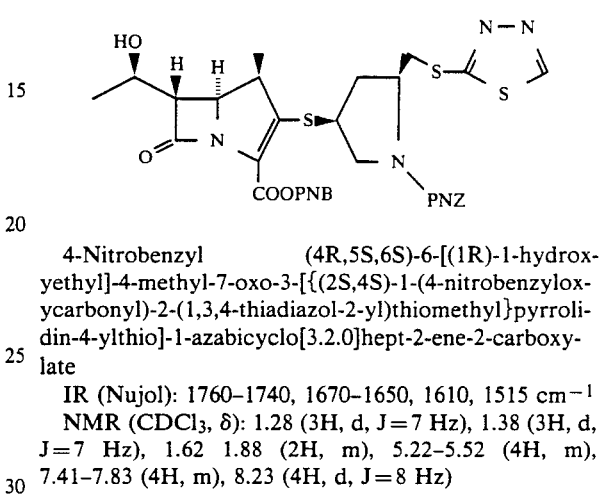

4-Nitrobenzyl (4R,5S,6S)-6-[(1R)-1-hydroxyethyl]-4-methyl-7-oxo-3-[{(2S,4S)-1-(4-nitrobenzyloxycarbonyl)-2-(1,3,4-thiadiazol-2-yl)thiomethyl}pyrrolidin-4-ylthio]-1-azabicyclo[3.2.0]hept-2-ene-2-carboxylate IR (Nujol): 1760-1740, 1670-1650, 1610, 1515 cm⁻¹

NMR (CDCl₃, δ): 1.28 (3H, d, J=7 Hz), 1.38 (3H, d, J=7 Hz), 1.62 1.88 (2H, m), 5.22-5.52 (4H, m), 7.41-7.83 (4H, m), 8.23 (4H, d, J=8 Hz)

EXAMPLE 28

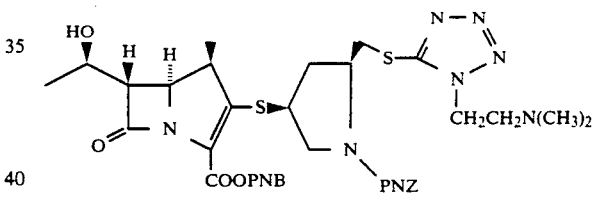

4-Nitrobenzyl (4R,5S,6S)-3-[(2S,4S)-2-[1-{2-(N,N-dimethylamino)ethyl}-1H-tetrazol-5-yl]thiomethyl-1-(4-nitrobenzyloxycarbonyl)pyrrolidin-4-ylthio]-6-[(1R)-1-hydroxyethyl]-4-methyl-7-oxo-1-azabicyclo[3.2.0]hept-2-ene-2-carboxylate IR (Nujol): 1765, 1700, 1605, 1520, 1350 cm⁻¹

NMR (CDCl₃, δ): 1.27 (3H, d, J=6 Hz), 1.36 (3H, d, J=6 Hz), 1.73-1.96 (4H, m), 2.25 (6H, s), 2.56 2.93 (3H, m), 5.20-5.47 (4H, m), 8.25 (4H, d, J=8 Hz)

EXAMPLE 29

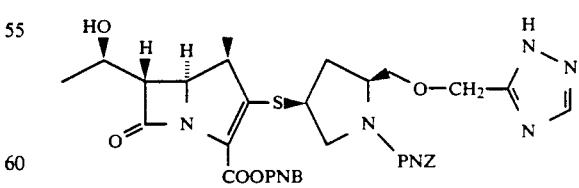

4-Nitrobenzyl (4R,5S,6S)-6-[(1R)-1-hydroxyethyl]-4-methyl-3-[(2S,4S)-1-(4-nitrobenzyloxycarbonyl)-2-{(2H-1,2,4-triazol-3-ylmethyl)oxymethyl}pyrrolidin-4-yl]thio-oxo-1-azabicyclo[3.2.0]hept-2-ene-2-carboxylate IR (CH₂Cl₂): 3200-3400, 1765, 1760-1710, 1610 cm⁻¹

NMR (CDCl₃, δ): 1.1–1.4 (6H, m), 2.3–2.7 (1H, m), 4.71 (2H, s), 5.1–5.6 (4H, m), 7.4–7.7 (4H, m), 8.0–8.3 (4H, m)

EXAMPLE 30

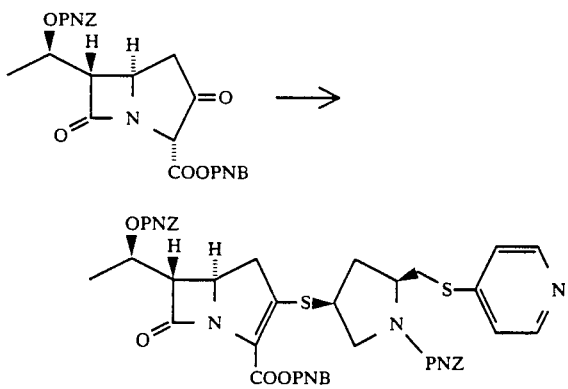

To a solution of 4-nitrobenzyl (2R,5R,6S)-6-[(1R)-1-(4-nitrobenzyloxycarbonyloxy)ethyl]-3,7-dioxo-1-azabicyclo[3.2.0]heptane-2-carboxylate (1.2 g) in dry dichloromethane (40 ml) were added N,N-diisopropyl-N-ethylamine (0.44 ml) and trifluoromethanesulfonic anhydride (0.40 ml) at −40° C., and the solution was stirred at the same temperature for 15 minutes.

To this solution were added N,N-diisopropyl-N-ethylamine (0.63 ml) and a solution of (2S,4S)-4-mercapto-1-(4-nitrobenzyloxycarbonyl)-2-(pyridin-4-ylthiomethyl)pyrrolidine (1.38 g) in dry dichloromethane (5 ml) successively at the same temperature under an atmosphere of nitrogen, and stirred at ambient temperature for 2 hours. The reaction mixture was washed with saturated aqueous sodium chloride, dried over anhydrous magnesium sulfate and evaporated in vacuo to give a residue. The residue was chromatographed on silica gel (100 g) eluting with a mixture of dichloromethane and acetone (4:1 V/V). The fractions containing the desired compound were collected and evaporated in vacuo to give 4-nitrobenzyl (5R,6S)-3-[(2S,4S)-1-(4-nitrobenzyloxycarbonyl)-2-(pyridin-4-ylthiomethyl)pyrrolidin-4-ylthio]-6-[(1R)-1-(4-nitrobenzyloxycarbonyloxy)ethyl]-7-oxo-1-azabicyclo[3.2.0]hept-2-ene-2-carboxylate (0.94 g).

IR (Nujol): 1780, 1750, 1690, 1610, 1575, 1520, 1350 cm⁻¹

NMR (CDCl₃, δ): 1.42 (3H, d, J=7 Hz), 1.80–2.15 (2H, m), 2.35–2.80 (1H, m), 2.85–3.25 (3H, m), 3.25–3.75 (4H, m), 3.90–4.35 (3H, m), 5.00–5.60 (6H, m), 7.35–7.75 (8H, m), 8.10–8.45 (8H, m)

EXAMPLE 31

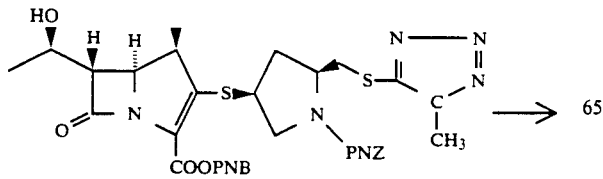

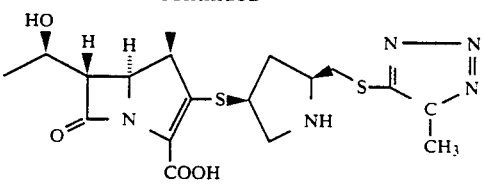

A mixture of 4-nitrobenzyl (4R,5S,6S)-3-[(2S,4S)-2-(1-methyl-1H-tetrazol-5-yl)thiomethyl-1-(4-nitrobenzyloxycarbonyl)pyrrolidin-4-yl]thio-4-methyl-6-[(1R)-1-hydroxyethyl]-7-oxo-1-azabicyclo[3.2.0]hept-2-ene-2-carboxylate (0.80 g), 20% palladium hydroxide on carbon (0.5 g), 0.05M phosphate buffer (pH 6.3, 30 ml) and tetrahydrofuran (30 ml) was stirred for 3 hours under atmospheric pressure of hydrogen at ambient temperature. After the catalyst was filtered off, the filtrate was concentrated under reduced pressure to remove the organic solvent. The residue was washed with ethyl acetate (30 ml×2) and evaporated in vacuo to remove the organic solvent. The residue was chromatographed on nonionic adsorption resin "Diaion HP-20" (Trademark, made by Mitsubishi Chemical Industries) (20 ml) eluting in turn with water (60 ml) and 10% aqueous acetone solution (120 ml). The fractions containing the desired compound were collected and lyophilized to give (4R,5S,6S)-6-[(1R)-1-hydroxyethyl]-4-methyl-3-[-(2S,4S)-2-{(1-methyl-1H-tetrazol-5-yl)thiomethyl}pyrrolidin-4-ylthio]-7-oxo-1-azabicyclo[3.2.0]hept-2-ene-2-carboxylic acid (0.23 g).

mp: >165° C. (dec.)

IR (Nujol): 1760–1750, 1590–1580, 1170 cm⁻¹

NMR (D₂O, δ): 1.21 (3H, d, J=7 Hz), 1.30 (3H, d, J=7 Hz), 1.65–2.05 (1H, m), 2.60–3.10 (1H, m), 3.25–3.90 (7H, m), 3.90–4.40 (3H, m), 4.03 (3H, s)

SI Mass: 441 (M+)

The following compounds were obtained in substantially the same manner as that of Example 31.

EXAMPLE 32

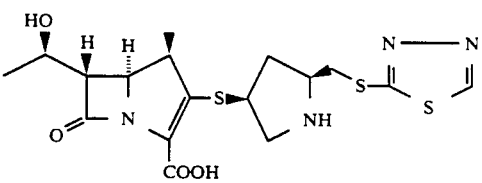

(4R,5S,6S)-6-[(1R)-1-Hydroxyethyl]-4-methyl-7-oxo-3-[(2S,4S)-2-(1,3,4-thiadiazol-2-ylthiomethyl)pyrrolidin-4-ylthio]-1-azabicyclo[3.2.0]hept-2-ene-2-carboxylic mp: >178° C. (dec.)

IR (Nujol): 1750, 1585, 1290, 1260 cm⁻¹

NMR (D₂O, δ): 1.19 (3H, d, J=7 Hz), 1.27 (3H, d, J=7 Hz), 1.60–2.10 (2H, m), 2.10–3.03 (2H, m), 9.40 (1H, s)

EXAMPLE 33

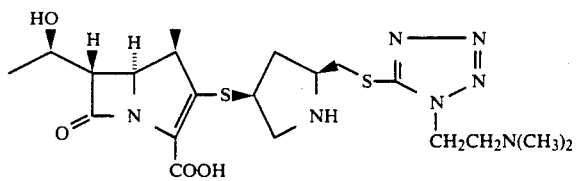

(4R,5S,6S) 6-[(1R)-1-hydroxyethyl]-4-methyl-7-oxo-3-[(2S,4S)-2-[1-{2-(N,N-dimethylamino)ethyl}-1H-tetrazol-5-yl]thiomethylpyrrolidin-4-ylthio]-1-azabicyclo[3.2.0]hept-2-ene-2-carboxylic acid mp: 163°-168° C. (dec.)

IR (Nujol): 1650, 1590-1580, 1290-1260 cm$^{-1}$

NMR (D$_2$O, δ): 1.28 (3H, d, J=7 Hz), 1.27 (3H, d, J=7 Hz), 1.53-1.95 (2H, m), 2.64 (6H, s), 2.20-3.04 (2H, m)

EXAMPLE 34

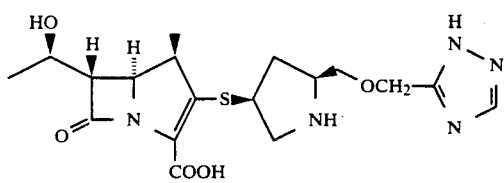

(4R,5S,6S)-6-[(1R)-1-Hydroxyethyl]-4-methyl-7-oxo-3-[(2S,4S)-2-{(2H-1,2,4-triazol-3-ylmethyl)oxymethyl}pyrrolidin-4-ylthio]-1-azabicyclo[3.2.0]hept-2-ene-2-carboxylic acid IR (KBr): 1740-1760, 1580 cm$^{-1}$ NMR (D$_2$O, δ): 1.19 (3H, d, J=8 Hz), 1.28 (3H, d, J=6 Hz), 2.5-2.9 (1H, m), 8.40 (1H, s)

SI Mass: 424 (M$^+$+1)

EXAMPLE 35

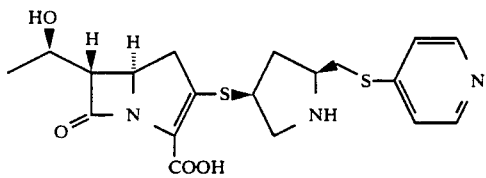

(5R,6S)-6-[(1R)-1-Hydroxyethyl]-7-oxo-3-[(2S,4S)-2-(pyridin-4-ylthiomethyl)pyrrolidin-4-ylthio]-1-azabicyclo[3.2.0]hept-2-ene-2-carboxylic acid mp: >184° C. (dec.)

IR (Nujol): 1770-1760, 1580, 1250-1220 cm$^{-1}$

NMR (DMSO-d$_6$, δ): 1.11 (3H, d, J=7 Hz), 1.36-1.50 (1H, m), 2.72-2.90 (1H, m), 7.22-7.32 (2H, m), 8.32-8.40 (2H, m)

SI Mass: 420 (M$^+$-2)

EXAMPLE 36

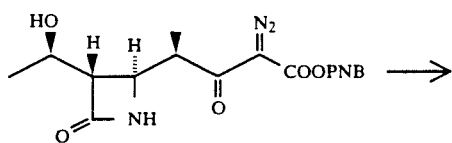

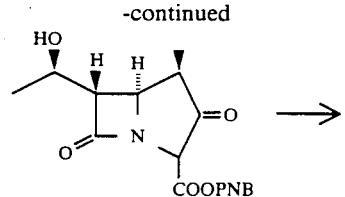

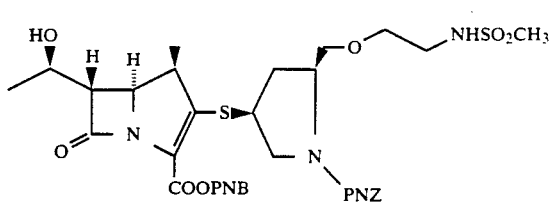

4-Nitrobenzyl (4R,5S,6S)-6-[(1R)-1-hydroxyethyl]-3-[(2S,4S)-2-{2-(methanesulfonylamino)ethyloxymethyl}-(4-nitrobenzyloxycarbonyl)pyrrolidin-4-yl]thio-4-methyl-7-oxo-1-azabicyclo[3.2.0]hept-2-ene-2-carboxylate (0.60 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.60 g) with (2S,4S)-4-mercapto-2-[2-(methanesulfonylamino)ethyloxymethyl]-1-(4-nitrobenzyloxycarbonyl)pyrrolidine (0.52 g) in substantially the same manner as that of Example 2.

IR (CHCl$_3$): 1765, 1705-1695 cm$^{-1}$

NMR (CDCl$_3$, δ): 1.28 (3H, d, J=7 Hz), 1.36 (3H, d, J=7 Hz), 2.95 (3H, s)

EXAMPLE 37

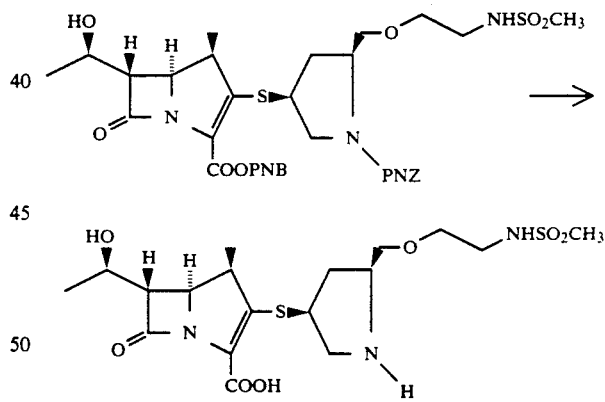

(4R,5S,6S)-6-[(1R)-1-Hydroxyethyl]-3-[(2S,4S)-2-{2-(methanesulfonylamino)ethyl}oxymethyl]pyrrolidin-4-yl]thio-4-methyl-7-oxo-1-azabicyclo[3.2.0]hept-2-ene-2-carboxylic acid (0.23 g) was obtained by hydrogenating 4-nitrobenzyl (4R,5S,6S)-6-[(1R)-1-hydroxyethyl]-3-(2S,4S)-2-{2-(methanesulfonylamino)ethyloxymethyl}-1-(4-nitrobenzyloxycarbonyl)pyrrolidin-4-yl]thio-4-methyl-7-oxo-1-azabicyclo[3.2.0]hept-2-ene-2-carboxylate (0.60 g) in substantially the same manner as that of Example 4.

mp: 160° C. (dec.)

IR (KBr): 1755-1730 cm$^{-1}$

NMR (D$_2$O, δ): 1.20 (3H, d, J=7 Hz), 1.28 (3H, d, J=7 Hz), 3.08 (3H, s)

EXAMPLE 38

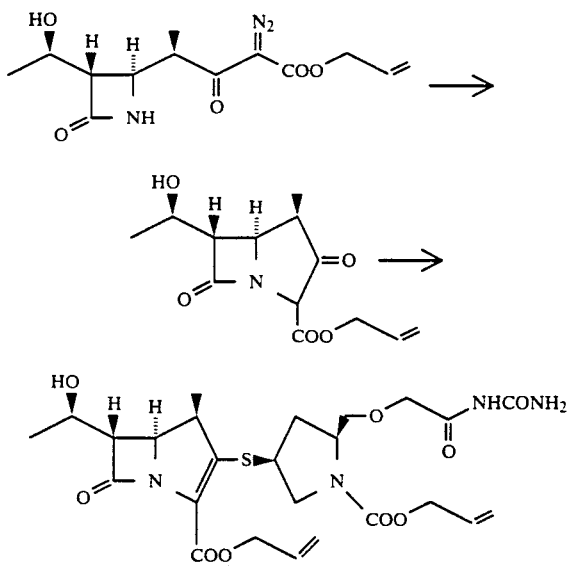

To a solution of allyl (4R)-2-diazo-4-[(2R,3S)-3-{(1R)-1-hydroxyethyl}-4-oxoazetidin-2-yl]-3-oxopentanoate (0.36 g) in dichloromethane (2.25 ml) was added rhodium(II) octanoate ( 6 mg) under reflux. After refluxing for 20 minutes, to the solution was added rhodium(II) octanoate (6 mg). The mixture was refluxed for 40 minutes. The reaction mixture was cooled and evaporated in vacuo to give a residue. The residue was dissolved in anhydrous acetonitrile (4.5 ml) and then evaporated. This operation was repeated once again and the resulting residue was dried in vacuo to give allyl (4R,5R,6S)-6-[(1R)-1-hydroxyethyl]-4-methyl-3,7-dioxo-1-azabicyclo[3.2.0]heptane-2-carboxylate. The residue containing the compound obtained above was dissolved in anhydrous acetonitrile (4.5 ml) and cooled to 0°-5° C. under an atmosphere of nitrogen. To this solution were added diphenyl phosphorochloridate (0.35 ml) and N,N-diisopropyl-N-ethylamine (0.32 ml) successively and the solution was stirred at 0°-5° C. for 1 hour. To the resulting solution were added dropwise a solution of (2S,4S)-1-allyloxycarbonyl-4-mercapto-2-[(ureidocarbonylxethyl)oxymethyl]pyrrolidine (0.35 g) in a mixture of dimethylformamide (1 ml) and acetonitrile (3 ml), and N,N-diisopropyl-N-ethylamine (0.35 ml) successively with stirring at 0°-5° C., and the stirring was continued at the same temperature for 3 hours. To a reaction mixture was added ethyl acetate (50 ml) and water (50 ml) with stirring, and the organic layer was separated.

The organic layer was dried over magnesium sulfate and evaporated in vacuo. The residue was chromatographed on silica gel (15 g) eluting with a mixture of acetone and dichloromethane (1:9 and then 2:8 V/V). The fractions containing the desired compound were collected and evaporated in vacuo to give allyl (4R,5S,6S)-3-[(2S,4S)-1-allyloxycarbonyl-2-{(ureidocarbonylmethyl)oxymethyl}pyrrolidin-4-yl]thio-6-[(1R)-1-hydroxyethyl]-4-methyl-7-oxo-1-azabicyclo[3.2.0]hept-2-ene-2-carboxylate (160 mg).

IR (CHCl₃): 1760, 1710–1685 cm⁻¹

EXAMPLE 39

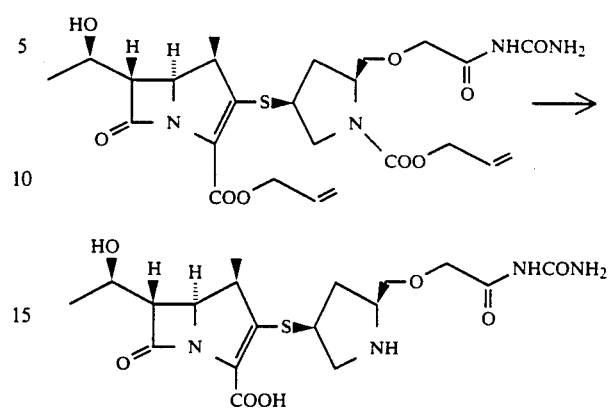

To a solution of allyl (4R,5S,6S)-3-[(2S,4S)-1-allyloxycarbonyl-2-{(ureidocarbonylmethyl)oxymethyl}pyrrolidin-4-yl]thio-6-[(1R)-1-hydroxyethyl]-4-methyl-7-oxo-1-azabicyclo[3.2.0]hept-2-ene-2-carboxylate (0.23 g) in a mixture of tetrahydrofuran (11.5 ml) and water (2.3 ml) were added triphenylphosphine (23 mg), morpholine (0.12 ml), formic acid (0.05 ml), and tetrakis(triphenylphosphine)palladium(O) (26 mg) successively with stirring under ice-cooling. The mixture was stirred at the same temperature for 1 hour and at ambient temperature for 2 hours, and poured into a mixture of ethyl acetate (50 ml) and water (50 ml). The aqueous layef was separated and washed 2 times with ethyl acetate (50 ml). This aqueous layer was concentrated in vacuo to remove the organic solvent. The residue was chromatographed on nonionic adsorption resin, "Diaion HP-20" (made by Mitsubishi Chemical Industries) (10 ml), eluting in turn with water, and a mixture of acetone and water (5:95 V/V). The fractions containing the desired compound were collected and lyophilized to give (4R,5S,6S)-6-[(1R)-1-hydroxyethyl]-4-methyl-7-oxo 3-[(2S,4S)-2-{(ureidocarbonylmethyl)oxymethyl}pyrrolidin-4-yl]thio-1-azabicyclo[3.2.0-]hept-2-ene-2-carboxylic acid (0.09 g).

mp: 155° C. (dec.)

IR (Nujol): 1750–1680 cm⁻¹

NMR (CDCl₃, δ): 1.20 (3H, d, J=7.5 Hz), 1.27 (3H, d, J=7.5 Hz)

SI MS: 443 (M⁺ +1), 426

EXAMPLE 40

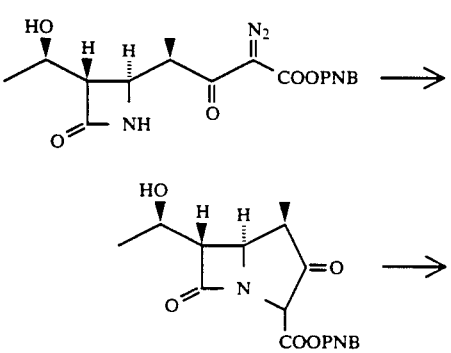

-continued

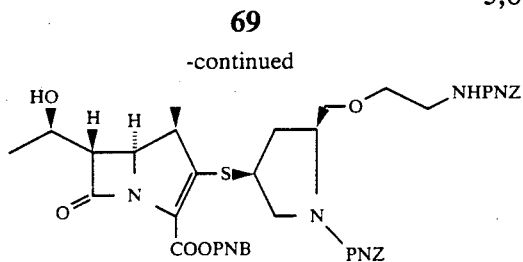

To a solution of 4-nitrobenzyl (4R)-2-diazo-4-[(2R,3S)-3-{(1R)-1-hydroxyethyl}-4-oxoazetidin-2-yl]-3-oxopentanoate (0.35 g) in dichloroethane (10 ml) was added rhodium acetate (1 mg) under reflux in a nitrogen stream. The mixture was refluxed for 30 minutes and concentrated under reduced pressure to give 4-nitrobenzyl (4R,5R,6S)-6-[(1R)-1-hydroxyethyl]-4-methyl-3,7-dioxo-1-azabicyclo[3.2.0]heptane-2-carboxylate.

The compound obtained above was dissolved in acetonitrile (10 ml). To the solution was added diphenyl phosphorochloridate (0.20 ml) at −10°∼5° C. in nitrogen stream and dropwise added N,N-diisopropyl-N-ethylamine (0.20 ml) at the same condition. The mixture was stirred at the same condition for 1 hour. To the solution were added N,N-diisopropyl-N-ethylamine (0.2 ml) and then a solution of (2S,4S)-4-mercapto-1-(4-nitrobenzyloxycarbonyl)-2-[2-(4-nitrobenzyloxycarbonylamino)ethyloxymethyl]pyrrolidine (0.46 g) in acetonitrile (2 ml) at −20° C. The mixture was stirred at the same temperature for 30 minutes and then at 0°-10° C. for 3 hours. The mixture was poured into a mixture of water (60 ml) and ethyl acetate (90 ml). The organic layer was washed with water (90 ml×2) and brine (90 ml) successively, dried over magnesium sulfate, and concentrated under reduced pressure to give a syrup. The syrup was subjected to a column chromatography on silica gel (20 g) and eluted with a mixture of acetone and dichloromethane (5:95, 10:90, and 15:85, in turn) to give 4-nitrobenzyl (4R,5S,6S)-6-[(1R)-1-hydroxyethyl]-4-methyl-3-[(2S,4S)-1-(4-nitrobenzyloxycarbonyl)-2-{2-(4-nitrobenzyloxycarbonylamino)ethyloxymethyl}pyrrolidin-4-yl]thio-7-oxo-1-azabicyclo[3.2.0]hept-2-ene-2-carboxylate (0.45 g).

IR (CHCl₃): 1765, 1705 cm⁻¹

EXAMPLE 41

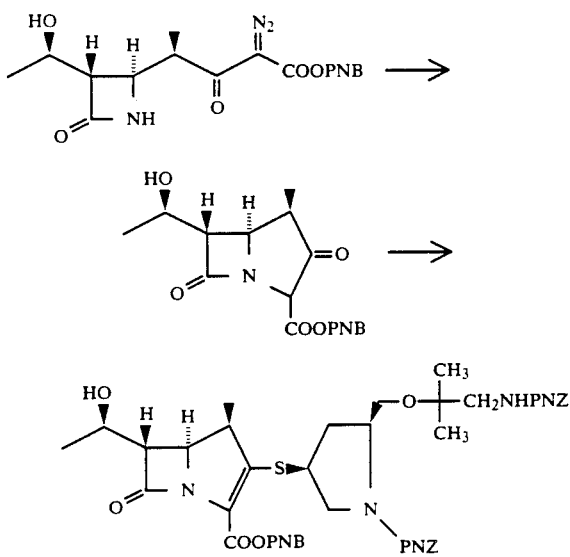

4-Nitrobenzyl (4R,5S,6S)-3-[(2S,4S)-2-[{1,1-dimethyl-2-(4-nitrobenzyloxycarbonylamino)ethyl}oxymethyl]-1-(4-nitrobenzyloxycarbonyl)pyrrolidin-4-yl]thio-6-(1R)-1-hydroxyethyl]-4-methyl-7-oxo-1-azabicyclo[3.2.0]hept-2-ene-2-carboxylate (0.79 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.55 g) with (2S,4S)-2-[{1,1-dimethyl-2-(4-nitrobenzyloxycarbonylamino)ethyl}oxymethyl]-4-mercapto-1-(4-nitrobenzyloxycarbonyl)pyrrolidine (0.70 g) in substantially the same manner as that of Example 40.

IR (CHCl₃): 1765, 1705, 1605 cm⁻¹

NMR (CDCl₃, δ): 1.10 (6H, s), 1.28 (3H, d, J=7 Hz), 1.38 (3H, d, J=7 Hz)

EXAMPLE 42

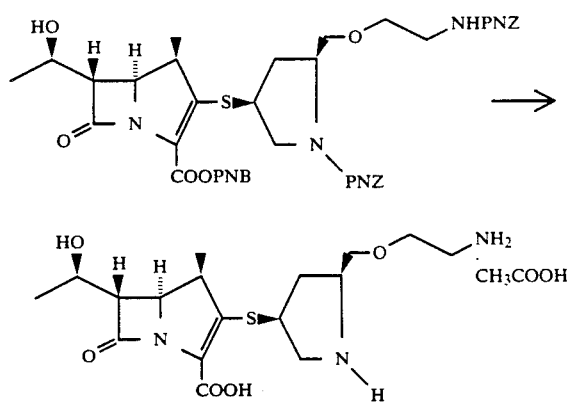

A solution of 4-nitrobenzyl (4R,5S,6S)-6-[(1R)-1-hydroxyethyl]-4-methyl-3-[(2S,4S)-1-(4-nitrobenzyloxycarbonyl)-2-{2-(4-nitrobenzyloxycarbonylamino)ethyloxymethyl}pyrrolidin-4-yl]thio-7-oxo-1-azabicyclo[3.2.0]hept-2-ene 2-carboxylate (0.45 g) in a mixture of tetrahydrofuran (25 ml) and 0.2M acetate buffer (pH 5.8) (25 ml) was stirred in the presence of 20% palladium hydroxide on carbon (0.1 g) under atmospheric pressure of hydrogen at ambient temperature for 8 hours. The catalyst was removed by filtration and the filtrate was concentrated under reduced pressure to remove tetrahydrofuran. The residual solution was washed with ethyl acetate (40 ml×2) and the organic solvent was removed by evaporation. The residual solution was subjected to a column chromatography on nonionic adsorption resin, "HP-20" (trademark, made by Mitsubishi Chemical Industries) (20 ml) and eluted with water. The fractions containing the desired compound were collected and lyophilized to give (4R,5S,6-S)-3-[(2S,4S)-2-(2-aminoethyloxymethyl)pyrrolidin-4-yl]thio-6-[(1R)-1-hydroxyethyl]-4-methyl-7-oxo-1-azabicyclo[3.2.0]hept-2-ene-2-carboxylic acid acetate (0.053 g).

mp: 90° C. (dec.)

IR (KBr): 1760–1735 cm⁻¹

NMR (D₂O, δ): 1.23 (3H, d, J=7 Hz), 1.19 (3H, d, J=7 Hz), 1.93 (3H, s)

FD MS: 386

EXAMPLE 43

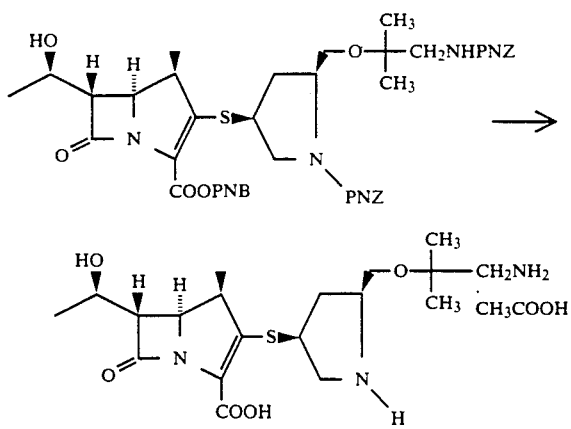

(4R,5S,6S)-3-[(2S,4S)-2-[(2-amino-1,1-dimethylethyl-)oxymethyl]pyrrolidin-4-yl]thio-6-[(1R)-1-hydroxyethyl]-4-methyl-7-oxo-1-azabicyclo[3.2.0]hept-2-ene-2-carboxylic acid acetate (0.16 g) was obtained by hydrogenating 4-nitrobenzyl (4R,5S,6S)-3-[(2S,4S)-2-{1,1-dimethyl-2-(4-nitrobenzyloxycarbonylamino)ethyl}oxymethyl]-1-(4-nitrobenzyloxycarbonyl)pyrrolidin yl]thio-6-[(1R)-1-hydroxyethyl]-4-methyl-7-oxo-1-azabicyclo[3.2.0]hept-2-ene-2-carboxylate (0.78 g) in substantially the same manner as that of Example 42.

mp: 180° C. (dec.)
IR (KBr): 1750–1730 cm$^{-1}$
NMR (D$_2$O, δ): 1.1–1.4 (12H, m), 1.78 (3H, s)
SI MS: 414, 343

EXAMPLE 44

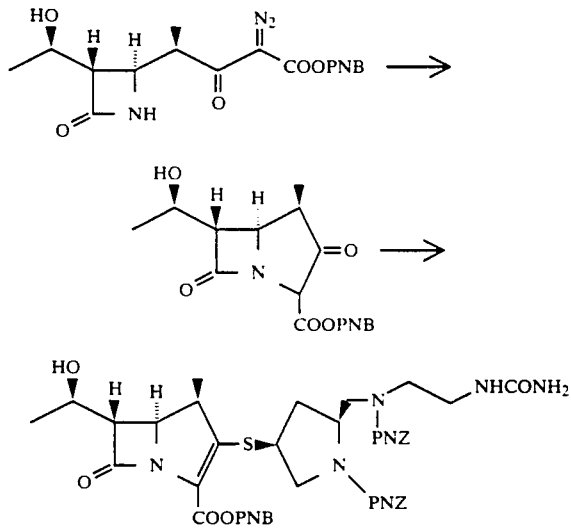

To a solution of 4-nitrobenzyl (4R)-2-diazo-4-[(2R,3S)-3-((1R)-1-hydroxyethyl)-4-oxoazetidin-2-yl]-3-oxopentanoate (0.6 g) in dichloroethane (12 ml) was added rhodium(II) acetate (1 mg) under reflux in a stream of nitrogen. After refluxing for 30 minutes, the mixture was concentrated under reduced pressure to give a syrup. The syrup was dissolved in acetonitrile (12 ml) and cooled to 0°~5° C. under an atmosphere of nitrogen. To the solution was added diphenyl phosphorochloridate (0.35 ml) and N,N-diisopropyl-N-ethylamine (0.30 ml) successively and the mixture was stirred at the same condition for 1 hour. To this mixture was added a solution of (2S, 4S)-4-mercapto-1-(4-nitrobenzyloxycarbonyl)-2-[N-(4-nitorbenzyloxycarbonyl)-N-(2-ureidoethyl)aminomethyl]pyrrolidine (0.75 g) in acetonitrile (2 ml) and N,N-diisopropyl-N-ethylamine (0.30 ml) successively at 0°~5° C. The mixture was stirred at 0°~5° C. for 3 hours. To the mixture was added ethyl acetate (100 ml). The solution was washed with water (100 ml×2) and brine (50 ml) successively, dried over magnesium sulfate and concentrated under reduced pressure to give a syrup. The syrup was subjected to a column chromatography on silica gel (15 g) and eluted with a mixture of acetone and dichloromethane (50:50 v/v) to give 4-nitrobenzyl (4R,5S,6S)-6-[(1R)-1-hydroxyethyl]-4-methyl-3-[(2S, 4S)-1-(4-nitrobenzyloxycarbonyl)-2-{N-(4-nitrobenzyloxycarbonyl)-N-(2-ureidoethyl)aminomethyl}pyrrolidin-4-yl]thio-7-oxo-1-azabicyclo[3.2.0]hept-2-ene-2-carboxylate (0.53 g).

IR (CHCl$_3$): 1765, 1710–1685 cm$^{-1}$

EXAMPLE 45

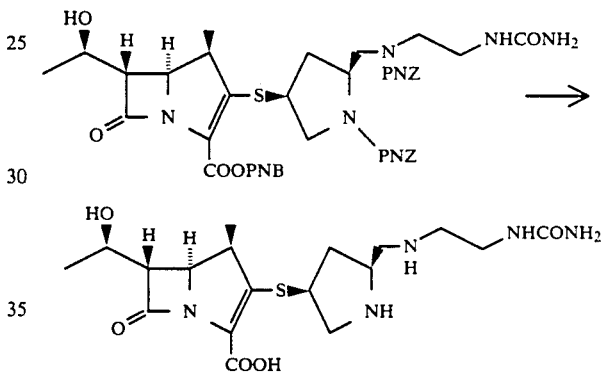

(4R, 5S, 6S)-6-[(1R)-1-Hydroxyethyl]-4-methyl-7-oxo-3-[(2S, 4S)-2-{(2-ureidoethyl)aminomethyl}pyrrolidin-4-yl]thio-1-azabicyclo[3.2.0]hept-2-ene-2-carboxylic acid (0.11 g) was obtained by hydrogenating 4-nitrobenzyl (4R, 5S,6S)-6-[(1R)-1-hydroxyethyl]-4-methyl-7-oxo-3-[(2S, 4S)-2-(2-ureidoethyl)aminomethyl-1-(4-nitrobenzyloxycarbonyl)pyrrolidin-4-yl]thio-1-azabicyclo[3.2.0]hept-2-ene-2-carboxylate (0.52 g) in substantially the same manner as that of Example 42.

mp: 200 ° C. (dec.)
IR (KBr): 1750–1730 cm$^{-1}$

What we claim is:

1. A compound of the formula which is selected from the group consisting of the formula:

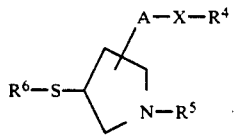

and the formula

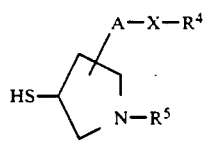

wherein
  R$^4$ is protected or unprotected hydroxy(lower)alkyl, protected or unprotected hydroxy(lower)alkyl having protected or unprotected amino; halo(lower)alkyl; protected or unprotected carbamoyl(lower)alkyl; protected or unprotected amino(lower)alkyl; protected or unprotected ureido(lower)alkyl; protected or unprotected ureidocarbonyl(lower)alkyl; triazolyl(lower)alkyl; saturated or unsaturated 3 to 8-membered heteromonocyclic group containing at least one heteroatom selected from oxygen, sulfur and nitrogen atom, wherein said heterocyclic group is unsubstituted or substituted by suitable substituent(s) selected from the group consisting of lower alkyl, amino, amino(lower)alkyl, mono(or di)(lower)alkylamino, mono(or di(lower)alkylamino(lower)alkyl and iminoprotective group; or lower alkylsulfonyl;
  R$^5$ is hydrogen, lower alkanimidoyl or imino-protective group,
  R$^6$ is mercapto-protective group,
  A is lower alkylene, and
  X is sulfur, oxygen, imino or protected imino, provided that when X is oxygen,
  then R$^4$ is not protected or unprotected ureido(lower)alkyl, and salts thereof.

2. A compound of claim 1, wherein
  R$^4$ is a hydroxy(lower)alkyl; acyloxy(lower)alkyl; triphenyl(lower)alkoxy(lower)alkyl; (tri(lower)alkkylsilyl)oxy(lower)alkyl; hydroxy(lower)alkyl having amino; hydroxy(lower)alkyl having acylamino; halo(lower)alkyl; carbamoyl(lower)alkyl; trihalo(lower)alkanoylcarbamoyl(lower)alkyl; N-bis((lower)alkoxy phenyl)(lower)alkyl)carbamoyl(lower)alkyl; amino(lower)alkyl; acylamino(lower)alkyl; ureido(lower)alkyl; phenyl(lower)alkyureido(lower)alkyl; ureidocarbonyl(lower)alkyl; phenyl(lower)alkylureidocarbonyl(lower)alkyl; triazolyl(lower)alkyl; saturated or unsaturated, 5 or 6-membered heteromonocyclic group containing 1 to 4 nitrogen atom(s) or containing 1 to 2 sulfur atom(s) and 1 to 3 nitrogen atom(s), wherein said heterocyclic group is unsubstituted or substituted by suitable substituent(s) selected from the group consisting of lower alkyl, amino, amino(lower)alkyl, mono(or di)(lower)alkylamino, mono(or di)(lower)alkylamino(lower)alkyl and acyl; or lower alkylsulfonyl;
  R$^5$ is hydrogen, lower alkanimidoyl or acyl,
  R$^6$ is acyl, or ar(lower)alkyl, and
  X is sulfur, oxygen, imino or acylimino.

3. A compound of claim 2, wherein
  R$^4$ is carbamoyloxy(lower)alkyl; (phenyl(or nitrophenyl)(lower)alkoxy)carbonyloxy(lower)alkyl; (triphenyl(lower)alkoxy)(lower)alkyl; (tri(lower)alkylsilyl)oxy(lower)alkyl; hydroxy(lower)alkyl; hydroxy(lower)alkyl having amino or phenyl(or nitrophenyl)(lower)alkoxycarbonylamino; halo(lower)alkyl; carbamoyl(lower)alkyl; trihalo(lower)alkanoylcarbamoyl(lower)alkyl; N-bis((lower)alkoxyphenyl)(lower)alkyl)carbamoyl(lower)alkyl; halosulfonylcarbamoyl(lower)alkyl; amino(lower)alkyl; N-(phenyl(or nitrophenyl)(lower)alkoxycarbonyl)amino(lower)alkyl; (lower)alkylsufonylamino(lower)alkyl; ureido(lower)alkyl; phenyl(lower)alkylureido(lower)alkyl; ureidocarbonyl(lower)alkyl; phenyl(lower)alkylureidocarbonyl (lower)alkyl; triazolyl(lower)alkyl; saturated or unsaturated 5 or 6-membered heteromonocyclic group containing 1 to 4 nitrogen atom(s) or containing 1 to 2 sulfur atom(s) and 1 to 3 nitrogen atom(s), which is unsubstituted or substituted by suitable substituent(s) selected from the group consisting of lower alkyl, amino, amino(lower)alkyl, mono(or di)(lower)alakylamino and mono(or di)(lower)alkylamino(lower)alkyl; or (lower)alkylsulfonyl;
  R$^5$ is hydrogen, lower alkanimidoyl, lower alkenyloxycarbonylimino or phenyl(or nitrophenyl(lower)alkoxycarbonylimino,
  R$^6$ is lower alkanoyl, benzoyl, triphenyl(lower)alkyl, and
  X is sulfur, oxygen, imino, lower alkenyloxycarbonylimino or phenyl(or nitrphenyl)(lower)alkoxycarbonylimino.

4. A compound of claim 3, wherein
  R$^4$ is carbamoyloxy(lower)alkyl; hydroxy(lower)alkyl; hydroxy(lower)alkyl having amino; dihalo(lower)alkyl; carbamoyl(lower)alkyl; amino(lower)alkyl; ureido(lower)alkyl; ureidocarbonyl(lower)alkyl; triazolyl(lower)alkyl; or pyridyl, pyrrolidinyl, thiadiazolyl or tetrazolyl, wherein said heterocyclic group is unsubstituted or substituted by substituent(s) selected from the consisting of lower alkyl, amino, amino(loweralkyl, mono(or di) (lower) alkylamino and mono(or di) (lower)alkylamino(lower)alkyl;
  R$^6$ is acetyl or benzoyl; and
  X is sulfur, oxygen or imino.

* * * * *

UNITED STATES PATENT AND TRADEMARK OFFICE
CERTIFICATE OF CORRECTION

PATENT NO. : 5,061,804
DATED : October 29, 1991
INVENTOR(S) : Masayoshi Murata et al.

It is certified that error appears in the above-identified patent and that said Letters Patent is hereby corrected as shown below:

Title page, item [54], fourth inventor, should be, --Kohji Hattori--.

Signed and Sealed this

First Day of June, 1993

Attest:

MICHAEL K. KIRK

Attesting Officer

Acting Commissioner of Patents and Trademarks